US007300780B2

(12) United States Patent
Leo et al.

(10) Patent No.: US 7,300,780 B2
(45) Date of Patent: Nov. 27, 2007

(54) GERMINAL CENTER KINASE PROTEINS, COMPOSITIONS, AND METHODS OF USE

(75) Inventors: Cindy Leo, San Francisco, CA (US); Ying Luo, Shanghai (CN); Xiang Xu, South San Francisco, CA (US); Simon Yu, Newark, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 124 days.

(21) Appl. No.: 10/493,164

(22) PCT Filed: Oct. 21, 2002

(86) PCT No.: PCT/US02/33845

§ 371 (c)(1),
(2), (4) Date: Sep. 20, 2004

(87) PCT Pub. No.: WO03/040409

PCT Pub. Date: May 15, 2003

(65) Prior Publication Data

US 2005/0019771 A1    Jan. 27, 2005

Related U.S. Application Data

(63) Continuation of application No. 10/029,115, filed on Oct. 19, 2001.

(51) Int. Cl.
  *C12N 9/12*  (2006.01)
  *C07K 1/00*  (2006.01)
(52) U.S. Cl. ...................... 435/194; 530/350
(58) Field of Classification Search ............... 530/350; 435/194, 252.3, 320.1
  See application file for complete search history.

(56) References Cited

U.S. PATENT DOCUMENTS

| 6,110,664 A | 8/2000 | Cowsert |
| 6,656,716 B1 | 12/2003 | Plowman et al. |
| 6,680,170 B2 | 1/2004 | Plowman |

FOREIGN PATENT DOCUMENTS

WO    WO 01/57190 A    8/2001

OTHER PUBLICATIONS

U.S. Appl. No. 10/029,115, filed Oct. 19, 2001, Ying Luo et al.
Dan, Ippeita, et al.; "Molecular cloning of MINK, a novel member of mammalian GCK family kinases, which is up-regulated during postnasal mouse cerebral development", *FEBS Letters*; 2000; pp. 19-23; vol. 469.

(Continued)

*Primary Examiner*—Maryam Monshipouri
(74) *Attorney, Agent, or Firm*—Townsend and Townsend and Crew, LLP

(57) ABSTRACT

The present invention provides compositions and methods for modulating cell proliferation, survival, morphology, and migration. Nucleic adds encoding proteins and proteins so encoded which are capable of modulating proliferation, survival, morphology and migration in mammalian cells are provided. Compositions and methods for the treatment of disorders related to cell proliferation, survival, morphology and migration are also provided. Prophylactics and methods for the prevention of such disorders are also provided. Also provided are compositions and methods for diagnostic and prognostic determination of such disorders. Further provided are assays for the identification of bioactive agents capable of modulating proliferation, survival, morphology and migration in mammalian cells.

2 Claims, 23 Drawing Sheets

Mink3a protein sequence
```
   1 MGDPAPARSLDDIDLSALRDPAGIFELVEVVGNGTYGQVYKGRHVKTGQLAAIKVMDVTE
  61 DEEEEIKQEINMLKKYSHHRNIATYYGAFIKKSPPGNDDQLWLVMEFCGAGSVTDLVKNT
 121 KGNALKEDCIAYICREILRGLAHLHAHKVIHRDIKGQNVLLTENAEVKLVDFGVSAQLDR
 181 TVGRRNTFIGTPYWMAPEVIACDENPDATYDYRSDIWSLGITAIEMAEGAPPLCDMHPMR
 241 ALFLIPRNPPPRLKSKKWSKKFIDFIDTCLIKTYLSRPPTEQLLKFPFIRDQPTERQVRI
 301 QLKDHIDRSRKKRGEKEETEYEYSGSEEEDDSHGEEGEPSSIMNVPGESTLRREFLRLQQ
 361 ENKSNSEALKQQQQLQQQQQRDPEAHIKHLLHQRQRRIEEQKEERRRVEEQQRREREQRK
 421 LQEKEQQRRLEDMQALRREEERRQAEREQEYKRKQLEEQRQSERLQRQLQQEHAYLKSLQ
 481 QQQQQQQLQKQQQQQLLPGDRKPLYHYGRGMNPADKPAWAREVEERTRMNKQQNSPLAKS
 541 KPGSTGPEPPIPQASPGPPGPLSQTPFMQRPVEPQEGPHKSLQDQPTRNLAAFPASHDPD
 601 PAIPAPTATPSARGAVIRQNSDPTSEGPGPSPNPPAWVRPDNEAPPKVPQRTSSIATALN
 661 TSGAGGSRPAQAVRARPRSNSAWQIYLQRRAERGTPKPPGPPAQPPGPPNASSNPDLRRS
 721 DPGWERSDSVLPASHGHLPQAGSLERNRVGASSKLDSSPVLSPGNKAKPDDHRSRPGRPA
 781 DFVLLKERTLDEAPRPPKKAMDYSSSSEEVESSEDDEEEGEGGPAEGSRDTPGGRSDGDT
 841 DSVSTMVVHDVEEITGTQPPYGGGTMVVQRTPEEERNLLHADSNGYTNLPDVVQPSHSPT
 901 ENSKGQSPPSKDGSGDYQSRGLVKAPGKSSFTMFVDLGIYQPGGSGDSIPITALVGGEGT
 961 RLDQLQYDVRKGSVVNVNPTNTRAHSETPEIRKYKKRFNSEILCAALWGVNLLVGTENGL
1021 MLLDRSGQGKVYGLIGRRRFQQMDVLEGLNLLITISGKRNKLRVYYLSWLRNKILHNDPE
1081 VEKKQGWTTVGDMEGCGHYRVVKYERIKFLVIALKSSVEVYAWAPKPYHKFMAFKSFADL
1141 PHRPLLVDLTVEEGQRLKVIYGSSAGFHAVDVDSGNSYDIYIPVHIQSQITPHAIIFLPN
1201 TDGMEMLLCYEDEGVYVNTYGRIIKDVVLQWGEMPTSVAYICSNQIMGWGEKAIEIRSVE
1261 TGHLDGVFMHKRAQRLKFLCERNDKVFFASVRSGGSSQVYFMTLNRNCIMNW
```

OTHER PUBLICATIONS

IP, Y. Tony and Roger J. Davis; "Signal transduction by the c-Jun N-terminal kinase (JNK)—from inflammation to development"; *Current Opinion in Cell Biology*; 1998; pp. 205-219; vol. 10.

Kyriakis, John M.; "Signaling by the Germinal Center Kinase Family of Protein Kinases"; *The Journal of Biological Chemistry*; Feb. 26, 1999; pp. 5259-5262; vol. 274, No. 9; USA.

Natoli, Gioacchino, et al.; "Activation of SAPK/JNK by TNF Receptor 1 Through a Noncytotoxic TRAF2-Dependent Pathway"; *Science*; Jan. 10, 1997; pp. 200-203; vol. 275.

Su, Yi-Chi et al.; "NIK is a new Ste20-related kinase that binds NCK and MEKK1 and activates the SAPK/JNK cascade via a conserved regulatory domain"; *The EMBO Journal*; 1997; pp. 1279-1290; vol. 16, No. 6; Oxford University Press.

Tang et al.: "Nucleic acids encoding polypeptides with cytokine-like activities, useful in diagnosis and gene therapy"; Abstract: Nov. 6, 2001; 3 pages.

Mink3a protein sequence

```
   1 MGDPAPARSLDDIDLSALRDPAGIFELVEVVGNGTYGQVYKGRHVKTGQLAAIKVMDVTE
  61 DEEEEIKQEINMLKKYSHHRNIATYYGAFIKKSPPGNDDQLWLVMEFCGAGSVTDLVKNT
 121 KGNALKEDCIAYICREILRGLAHLHAHKVIHRDIKGQNVLLTENAEVKLVDFGVSAQLDR
 181 TVGRRNTFIGTPYWMAPEVIACDENPDATYDYRSDIWSLGITAIEMAEGAPPLCDMHPMR
 241 ALFLIPRNPPPRLKSKKWSKKFIDFIDTCLIKTYLSRPPTEQLLKFPFIRDQPTERQVRI
 301 QLKDHIDRSRKKRGEKEETEYEYSGSEEEDDSHGEEGEPSSIMNVPGESTLRREFLRLQQ
 361 ENKSNSEALKQQQQLQQQQQRDPEAHIKHLLHQRQRRIEEQKEERRRVEEQQRREREQRK
 421 LQEKEQQRRLEDMQALRREEERRQAEREQEYKRKQLEEQRQSERLQRQLQQEHAYLKSLQ
 481 QQQQQQQLQKQQQQQLLPGDRKPLYHYGRGMNPADKPAWAREVEERTRMNKQQNSPLAKS
 541 KPGSTGPEPPIPQASPGPPGPLSQTPPMQRPVEPQEGPHKSLQDQPTRNLAAFPASHDPD
 601 PAIPAPTATPSARGAVIRQNSDPTSEGPGPSPNPPAWVRPDNEAPPKVPQRTSSIATALN
 661 TSGAGGSRPAQAVRARPRSNSAWQIYLQRRAERGTPKPPGPPAQPPGPPNASSNPDLRRS
 721 DPGWERSDSVLPASHGHLPQAGSLERNRVGASSKLDSSPVLSPGNKAKPDDHRSRPGRPA
 781 DFVLLKERTLDEAPRPPKKAMDYSSSSEEVESSEDDEEEGEGGPAEGSRDTPGGRSDGDT
 841 DSVSTMVVHDVEEITGTQPPYGGGTMVVQRTPEEERNLLHADSNGYTNLPDVVQPSHSPT
 901 ENSKGQSPPSKDGSGDYQSRGLVKAPGKSSFTMFVDLGIYQPGGSGDSIPITALVGGEGT
 961 RLDQLQYDVRKGSVVNVNPTNTRAHSETPEIRKYKKRFNSEILCAALWGVNLLVGTENGL
1021 MLLDRSGQGKVYGLIGRRRFQQMDVLEGLNLLITISGKRNKLRVYYLSWLRNKILHNDPE
1081 VEKKQGWTTVGDMEGCGHYRVVKYERIKFLVIALKSSVEVYAWAPKPYHKFMAFKSFADL
1141 PHRPLLVDLTVEEGQRLKVIYGSSAGFHAVDVDSGNSYDIYIPVHIQSQITPHAIIFLPN
1201 TDGMEMLLCYEDEGVYVNTYGRIIKDVVLQWGEMPTSVAYICSNQIMGWGEKAIEIRSVE
1261 TGHLDGVFMHKRAQRLKFLCERNDKVFFASVRSGGSSQVYFMTLNRNCIMNW
```

*FIG. 1*

Mink3a nucleotide sequence
GCCCTTATGGGCGACCCAGCCCCCGCCCGC
AGCCTGGACGACATCGACCTGTCCGCCCTGCGGGACCCTGCTGGGATCTTTGAGCTTGTG
GAGGTGGTCGGCAATGGAACCTACGGACAGGTGTACAAGGGTCGGCATGTCAAGACGGGG
CAGCTGGCTGCCATCAAGGTCATGGATGTCACGGAGGACGAGGAGGAAGAGATCAAACAG
GAGATCAACATGCTGAAAAAGTACTCTCACCACCGCAACATCGCCACCTACTACGGAGCC
TTCATCAAGAAGAGCCCCCCGGGAAACGATGACCAGCTCTGGCTGGTGATGGAGTTCTGT
GGTGCTGGTTCAGTGACTGACCTGGTAAAGAACACAAAAGGCAACGCCCTGAAGGAGGAC
TGTATCGCCTATATCTGCAGGGAGATCCTCAGGGGTCTGGCCCATCTCCATGCCCACAAG
GTGATCCATCGAGACATCAAGGGGCAGAATGTGCTGCTGACAGAGAATGCTGAGGTCAAG
CTAGTGGATTTTGGGGTGAGTGCTCAGCTGGACCGCACCGTGGGCAGACGGAACACTTTC
ATTGGGACTCCCTACTGGATGGCTCCAGAGGTCATCGCCTGTGATGAGAACCCTGATGCC
ACCTATGATTACAGGAGTGATATTTGGTCTCTAGGAATCACAGCCATCGAGATGGCAGAG
GGAGCCCCCCCTCTGTGTGACATGCACCCCATGCGAGCCCTCTTCCTCATTCCTCGGAAC
CCTCCGCCCAGGCTCAAGTCCAAGAAGTGGTCTAAGAAGTTCATTGACTTCATTGACACA
TGTCTCATCAAGACTTACCTGAGCCGCCCACCCACGGAGCAGCTACTGAAGTTTCCCTTC
ATCCGGGACCAGCCCACGGAGCGGCAGGTCCGCATCCAGCTTAAGGACCACATTGACCGA
TCCCGGAAGAAGCGGGGTGAGAAAGAGGAGACAGAATATGAGTACAGCGGCAGCGAGGAG
GAAGATGACAGCCATGGAGAGGAAGGAGAGCCAAGCTCCATCATGAACGTGCCTGGAGAG
TCGACTCTACGCCGGGAGTTTCTCCGGCTCCAGCAGGAAAATAAGAGCAACTCAGAGGCT
TTAAAACAGCAGCAGCAGCTGCAGCAGCAGCAGCAGCGAGACCCCGAGGCACACATCAAA
CACCTGCTGCACCAGCGGCAGCGGCGCATAGAGGAGCAGAAGGAGGAGCGGCGCCGCGTG
GAGGAGCAACAGCGGCGGGAGCGGGAGCAGCGGAAGCTGCAGGAGAAGGAGCAGCAGCGG
CGGCTGGAGGACATGCAGGCTCTGCGGCGGGAGGAGGAGCGGCGGCAGGCGGAGCGTGAG
CAGGAATACAAGCGGAAGCAGCTGGAGGAGCAGCGGCAGTCAGAACGTCTCCAGAGGCAG
CTGCAGCAGGAGCATGCCTACCTCAAGTCCCTGCAGCAGCAGCAACAGCAGCAGCAGCTT
CAGAAACAGCAGCAGCAGCAGCTCCTGCCTGGGGACAGGAAGCCCCTGTACCATTATGGT
CGGGGCATGAATCCCGCTGACAAACCAGCCTGGGCCCGAGAGGTAGAAGAGAGAACAAGG
ATGAACAAGCAGCAGAACTCTCCCTTGGCCAAGAGCAAGCCAGGCAGCACGGGGCCTGAG
CCCCCCATCCCCCAGGCCTCCCCAGGGCCCCAGGACCCCTTTCCAGACTCCTCCTATG
CAGAGGCCGGTGGAGCCCCAGGAGGGACCGCACAAGTCCCTGCAGGACCAGCCCACCCGA
AACCTGGCTGCCTTCCCAGCCTCCCATGACCCCGACCCTGCCATCCCCGCACCCACTGCC
ACGCCCAGTGCCCGAGGAGCTGTCATCCGCCAGAATTCAGACCCCACCTCTGAAGGACCT
GGCCCCAGCCCGAATCCCCCAGCCTGGGTCCGCCCAGATAACGAGGCCCCACCCAAGGTG
CCTCAGAGGACCTCATCTATCGCCACTGCCCTTAACACCAGTGGGGCCGGAGGGTCCCGG
CCAGCCCAGGCAGTCCGTGCCAGACCTCGCAGCAACTCCGCCTGGCAAATCTATCTGCAA
AGGCGGGCAGAGCGGGGCACCCCAAAGCCTCCAGGGCCCCCTGCTCAGCCCCCTGGCCCG
CCCAACGCCTCTAGTAACCCCGACCTCAGGAGGAGCGACCCTGGCTGGGAACGCTCGGAC
AGCGTCCTTCCAGCCTCTCACGGGCACCTCCCCAGGCTGGCTCACTGGAGCGGAACCGC
GTGGGAGCCTCCTCCAAACTGGACAGCTCCCCTGTGCTCTCCCCTGGGAATAAAGCCAAG

FIG. 1 (CONTINUED)

CCCGACGACCACCGCTCACGGCCAGGCCGGCCCGCAGACTTTGTGTTGCTGAAAGAGCGG
ACTCTGGACGAGGCCCCTCGGCCTCCCAAGAAGGCCATGGACTACTCGTCGTCCAGCGAG
GAGGTGGAAAGCAGTGAGGACGACGAGGAGGAAGGCGAAGGCGGGCCAGCAGAGGGGAGC
AGAGATACCCCTGGGGGCCGCAGCGATGGGGATACAGACAGCGTCAGCACCATGGTGGTC
CACGACGTCGAGGAGATCACCGGGACCCAGCCCCATACGGGGGCGGCACCATGGTGGTC
CAGCGCACCCCTGAAGAGGAGCGGAACCTGCTGCATGCTGACAGCAATGGGTACACAAAC
CTGCCTGACGTGGTCCAGCCCAGCCACTCACCCACCGAGAACAGCAAAGGCCAAAGCCCA
CCCTCGAAGGATGGGAGTGGTGACTACCAGTCTCGTGGGCTGGTAAAGGCCCCTGGCAAG
AGCTCGTTCACGATGTTTGTGGATCTAGGGATCTACCAGCCTGGAGGCAGTGGGGACAGC
ATCCCCATCACAGCCCTAGTGGGTGGAGAGGGCACTCGGCTCGACCAGCTGCAGTACGAC
GTGAGGAAGGGTTCTGTGGTCAACGTGAATCCCACCAACACCCGGGCCCACAGTGAGACC
CCTGAGATCCGGAAGTACAAGAAGCGATTCAACTCCGAGATCCTCTGTGCAGCCCTTTGG
GGGGTCAACCTGCTGGTGGGCACGGAGAACGGGCTGATGTTGCTGGACCGAAGTGGGCAG
GGCAAGGTGTATGGACTCATTGGCGGCGACGCTTCCAGCAGATGGATGTGCTGGAGGGG
CTCAACCTGCTCATCACCATCTCAGGGAAAAGGAACAAACTGCGGGTGTATTACCTGTCC
TGGCTCCGGAACAAGATTCTGCACAATGACCCAGAAGTGGAGAAGAAGCAGGGCTGGACC
ACCGTGGGGGACATGGAGGGCTGCGGGCACTACCGTGTTGTGAAATACGAGCGGATTAAG
TTCCTGGTCATCGCCCTCAAGAGCTCCGTGGAGGTGTATGCCTGGGCCCCCAAACCCTAC
CACAAATTCATGGCCTTCAAGTCCTTTGCCGACCTCCCCACCGCCCTCTGCTGGTCGAC
CTGACAGTAGAGGAGGGGCAGCGGCTCAAGGTCATCTATGGCTCCAGTGCTGGCTTCCAT
GCTGTGGATGTCGACTCGGGGAACAGCTATGACATCTACATCCCTGTGCACATCCAGAGC
CAGATCACGCCCCATGCCATCATCTTCCTCCCCAACACCGACGGCATGGAGATGCTGCTG
TGCTACGAGGACGAGGGTGTCTACGTCAACACGTACGGGCGCATCATTAAGGATGTGGTG
CTGCAGTGGGGGGAGATGCCTACTTCTGTGGCCTACATCTGCTCCAACCAGATAATGGGC
TGGGGTGAGAAAGCCATTGAGATCCGCTCTGTGGAGACGGGCCACCTCGACGGGGTCTTC
ATGCACAAACGAGCTCAGAGGCTCAAGTTCCTGTGTGAGCGGAATGACAAGGTGTTTTTT
GCCTCAGTCCGCTCTGGGGGCAGCAGCCAAGTTTACTTCATGACTCTGAACCGTAACTGC
ATCATGAACTGGTGAAAGGGC

Mink3b protein sequence
1   MDVTEDEEEEIKQEINMLKKYSHHRNIATYYGAFIKKSPPGNDDQLWLVMEFCGAGSVTD
61  LVKNTKGNALKEDCIAYICREILRGLAHLHAHKVIHRDIKGQNVLLTENAEVKLVDFGVS
121 AQLDRTVGRRNTFIGTPYWMAPEVIACDENPDATYDYRSDIWSLGITAIEMAEGAPPLCD
181 MHPMRALFLIPRNPPPRLKSKKWSKKFIDFIDTCLIKTYLSRPPTEQLLKFPFIRDQPTE
241 RQVRIQLKDHIDRSRKKRGEKEETEYEYSGSEEEDDSHGEEGEPSSIMNVPGESTLRREF
301 LRLQQENKSNSEALKQQQQLQQQQQRDPEAHIKHLLHQRQRRIEEQKEERRRVEEQQRRE
361 REQRKLQEKEQQRRLEDMQALRREEERRQAEREQEYKRKQLEEQRQSERLQRQLQQEHAY
421 LKSLQQQQQQQLQKQQQQLLPGDRKPLYHYGRGMNPADKPAWAREVEERTRMNKQQNS
481 PLAKSKPGSTGPEPPIPQASPGPPGPLSQTPPMQRPVEPQEGPHKSLVAHRVPLKPYAAP
541 VPRSQSLQDQPTRNLAAFPASHDPDPAIPAPTATPSARGAVIRQNSDPTSEGPGPSPNPP
601 AWVRPDNEAPPKVPQRTSSIATALNTSGAGGSRPAQAVRARPRSNSAWQIYLQRRAERGT
661 PKPPGPPAQPPGPPNASSNPDLRRSDPGWERSDSVLPASHGHLPQAGSLERNRVGASSKL
721 DSSPVLSPGNKAKPDDHRSRPGRPAVSHLVAGMACLILVWGLASGCWVSGVGSPLIYREG
781 LWGWRDWCFSWC

FIG. 1 (CONTINUED)

Mink3b nucleotide sequence
GCCCTT
ACCATTCTGGAAGCTCCCTAGAATCTCCTGGAATGCTTAATGGACCTTTCCAGCACCGAA
ATTCAAGAATTATGACTCATCGGTCAGCAGAAAAGACCCTGCTGGGATCTTTGAGCTTGT
GGAGGTGGTCGGCAATGGAACCTACGGACAGGTGTACAAGGGTCGGCATGTCAAGACGGG
GCAGCTGGCTGCCATCAAGGTCATGGATGTCACGGAGGACGAGGAGGAAGAGATCAAACA
GGAGATCAACATGCTGAAAAAGTACTCTCACCACCGCAACATCGCCACCTACTACGGAGC
CTTCATCAAGAAGAGCCCCCGGGAAACGATGACCAGCTCTGGCTGGTGATGGAGTTCTG
TGGTGCTGGTTCAGTGACTGACCTGGTAAAGAACACAAAAGGCAACGCCCTGAAGGAGGA
CTGTATCGCCTATATCTGCAGGGAGATCCTCAGGGGTCTGGCCCATCTCCATGCCCACAA
GGTGATCCATCGAGACATCAAGGGGCAGAATGTGCTGCTGACAGAGAATGCTGAGGTCAA
GCTAGTGGATTTTGGGGTGAGTGCTCAGCTGGACCGCACCGTGGGCAGACGGAACACTTT
CATTGGGACTCCCTACTGGATGGCTCCAGAGGTCATCGCCTGTGATGAGAACCCTGATGC
CACCTATGATTACAGGAGTGATATTTGGTCTCTAGGAATCACAGCCATCGAGATGGCAGA
GGGAGCCCCCCCTCTGTGTGACATGCACCCATGCGAGCCCTCTTCCTCATTCCTCGGAA
CCCTCCGCCCAGGCTCAAGTCCAAGAAGTGGTCTAAGAAGTTCATTGACTTCATTGACAC
ATGTCTCATCAAGACTTACCTGAGCCGCCCACCCACGGAGCAGCTACTGAAGTTTCCCTT
CATCCGGGACCAGCCCACGGAGCGGCAGGTCCGCATCCAGCTTAAGGACCACATTGACCG
ATCCCGGAAGAAGCGGGGTGAGAAAGAGGAGACAGAATATGAGTACAGCGGCAGCGAGGA
GGAAGATGACAGCCATGGAGAGGAAGGAGAGCCAAGCTCCATCATGAACGTGCCTGGAGA
GTCGACTCTACGCCGGGAGTTTCTCCGGCTCCAGCAGGAAAATAAGAGCAACTCAGAGGC
TTTAAAACAGCAGCAGCAGCTGCAGCAGCAGCAGCAGCAGACCCCGAGGCACACATCAA
ACACCTGCTGCACCAGCGGCAGCGGCGCATAGAGGAGCAGAAGGAGGAGCGGCGCCGCGT
GGAGGAGCAACAGCGGCGGGAGCGGGAGCAGCGGAAGCTGCAGGAGAAGGAGCAGCAGCG
GCGGCTGGAGGACATGCAGGCTCTGCGGCGGGAGGAGGAGCGGCGGCAGGCGGAGCGTGA
GCAGGAATACAAGCGGAAGCAGCTGGAGGAGCAGCGGCAGTCAGAACGTCTCCAGAGGCA
GCTGCAGCAGGAGCATGCCTACCTCAAGTCCCTGCAGCAGCAGCAACAGCAGCAGCAGCT
TCAGAAACAGCAGCAGCAGCAGCTCCTGCCTGGGGACAGGAAGCCCCTGTACCATTATGG
TCGGGGCATGAATCCCGCTGACAAACCAGCCTGGGCCCGAGAGGTAGAAGAGAGAACAAG
GATGAACAAGCAGCAGAACTCTCCCTTGGCCAAGAGCAAGCCAGGCAGCACGGGGCCTGA
GCCCCCATCCCCCAGGCCTCCCCAGGGCCCCAGGACCCCTTTCCCAGACTCCTCCTAT
GCAGAGGCCGGTGGAGCCCCAGGAGGGACCGCACAAGAGCCTGGTGGCACACCGGGTCCC
ACTGAAGCCATATGCAGCACCTGTACCCCGATCCCAGTCCCTGCAGGACCAGCCCACCCG
AAACCTGGCTGCCTTCCCAGCCTCCCATGACCCCGACCCTGCCATCCCCGCACCCACTGC
CACGCCCAGTGCCCGAGGAGCTGTCATCCGCCAGAATTCAGACCCCACCTCTGAAGGACC
TGGCCCCAGCCCGAATCCCCCAGCCTGGGTCCGCCCAGATAACGAGGCCCCACCCAAGGT
GCCTCAGAGGACCTCATCTATCGCCACTGCCCTTAACACCAGTGGGGCCGGAGGGTCCCG
GCCAGCCCAGGCAGTCCGTGCCAGACCTCGCAGCAACTCCGCCTGGCAAATCTATCTGCA

*FIG. 1* (CONTINUED)

```
AAGGCGGGCAGAGCGGGGCACCCCAAAGCCTCCAGGGCCCCCTGCTCAGCCCCCTGGCCC
GCCCAACGCCTCTAGTAACCCCGACCTCAGGAGGAGCGACCCTGGCTGGGAACGCTCGGA
CAGCGTCCTTCCAGCCTCTCACGGGCACCTCCCCCAGGCTGGCTCACTGGAGCGGAACCG
CGTGGGAGCCTCCTCCAAACTGGACAGCTCCCTGTGCTCTCCCTGGGAATAAAGCCAA
GCCCGACGACCACCGCTCACGGCCAGGCCGGCCCGCAGTGAGTCACCTGGTGGCAGGCAT
GGCCTGCCTCATCCTGGTTTGGGGCTTAGCCTCAGGGTGCTGGGTGTCAGGGGTGGGGTC
TCCGCTGATCTACCGAGAAGGGCTGTGGGGATGGAGGGACTGGTGCTTCTCATGGTGCTA
ACCTTTCCTAACCTCTCTCCTAACCTCTCTCCTAACCTCTCTTCTGGCTCTTTCTTCCCC
TGCGGCCCCTCCCAGAGCTATAAGCGAGCAATTGGTGAGGTTAGTGAGATGGGCCTGCTT
GTGGGAGCCCCTCCTGTCGCCCTGCTGGGGCGTCCCGGCACCCTTTGTCTACCTCCACCC
AGCCCAGCTTCTCCCTGCCCCTCACGTGGCTCCTCCCTGCAGGACTTTGTGTTGCTGAA
AGAGCGGACTCTGGACGAGGCCCCTCGGCCTCCCAAGAAGGCCATGGACTACTCGTCGTC
CAGCGAGGAGGTGGAAAGCAGTGAGGACGACGAGGAGGAAGGCGAAGGCGGGCCAGCAGA
GGGGAGCAGAGATACCCCTGGGGGCCGCAGCGATGGGGATACAGACAGCGTCAGCACCAT
GGTGGTCCACGACGTCGAGGAGATCACCGGGACCCAGCCCCATACGGGGGCGGCACCAT
GGTGGTCCAGCGCACCCCTGAAGAGGAGCGGAACCCGCTGCATGCTGACAGCAATGGGTA
CACAAACCTGCCTGACGTGGTCCAGCCCAGCCACTCACCCACCGAGAACAGCAAAGGCCA
AAGCCCACCCTCGAAGGATGGGAGTGGTGACTACCAGTCTCGTGGGCTGGTAAAGGCCCC
TGGCAAGAGCTCGTTCACGATGTTTGTGGATCTAGGGATCTACCAGCCTGGAGGCAGTGG
GGACAGCATCCCCATCACAGCCCTAGTGGGTGGAGAGGGCACTCGGCTCGACCAGCTGCA
GTACGACGTGAGGAAGGGTTCTGTGGTCAACGTGAATCCCACCAACACCCGGGCCCACAG
TGAGACCCCTGAGATCCGGAAGTACAAGAAGCGATTCAACTCCGAGATCCTCTGTGCAGC
CCTTTGGGGGGTCAACCTGCTGGTGGGCACGGAGAACGGGCTGATGTTGCTGGACCGAAG
TGGGCAGGACAAGGTGTATGGACTCATTGGGCGACGACGCTTCCAGCAGATGGATGTGCT
GGAGGGGCTCAACCTGCTCATCACCATCTCAGGGAAAAGGAACAAACTGCGGGTGTATTA
CCTGTCCTGGCTCCGGAACAAGATTCTGCACAATGACCCAGAAGTGGAGAAGAAGCAGGG
CTGGACCACCGTGGGGGACATGGAGGGCTGCGGGCACTACCGTGTTGTGAAATACGAGCG
GATTAAGTTCCTGGTCATCGCCCTCAAGAGCTCCGTGGAGGTGTATGCCTGGGCCCCCAA
ACCCTACCACAAATTCATGGCCTTCAAGTCCTTTGCCGACCTCCCCCACCGCCCTCTGCT
GGTCGACCTGACAGTAGAGGAGGGGCAGCGGCTCAAGGTCATCTATGGCTCCAGTGCTGG
CTTCCATGCTGTGGATGTCGACTCGGGGAACAGCTATGACATCTACATCCCTGTGCACAT
CCAGAGCCAGATCACGCCCCATGCCATCATCTTCCTCCCCAACACCGACGGCATGGAGAT
GCTGCTGTGCTACGAGGACGAGGGTGTCTACGTCAACACGTACGGGCGCATCATTAAGGA
TGTGGTGCTGCAGTGGGGGGAGATGCCTACTTCTGTGGCCTACATCTGCTCCAACCAGAT
AATGGGCTGGGGTGAGAAAGCCATTGAGATCCGCTCTGTGGAGACGGGCCACCTCGACGG
GGTCTTCATGCACAAACGAGCTCAGAGGCTCAAGTTCCTGTGTGAGCGGAATGACAAGGT
GTTTTTTGCCTCAGTCCGCTCTGGGGGCAGCAGCCAAGTTTACTTCATGACTCTGAACCG
TAACTGCATCATGAACTGGTGAAAGGGC
```

FIG. 1 (CONTINUED)

Mink3c protein sequence

```
1    MDVTEDEEEEIKQEINMLKKYSHHRNIATYYGAFIKKSPPGNDDQLWLVMEFCGAGSVTD
61   LVKNTKGNALKEDCIAYICREILRGLAHLHAHKVIHRDIKGQNVLLTENAEVKLVDFGVS
121  AQLDRTVGRRNTFIGTPYWMAPEVIACDENPDATYDYRSDIWSLGITAIEMAEGAPPLCD
181  MHPMRALFLIPRNPPPRLKSKKWSKKFIDFIDTCLIKTYLSRPPTEQLLKFPFIRDQPTE
241  RQVRIQLKDHIDRSRKKRGEKEETEYEYSGSEEEDDSHGEEGEPSSIMNVPGESTLRREF
301  LRLQQENKSNSEALKQQQQLQQQQQRDPEAHIKHLLHQRQRRIEEQKEERRRVEEQQRRG
361  REQRKLQEKEQQRRLEDMQALRREEERRQAEREQEYKRKQLEEQRQSERLQRQLQQEHAY
421  LKSLQQQQQQQQLQKQQQQQLLPGDRKPLYHYGRGMNPADKPAWAREVEERTRMNKQQNS
481  PLAKSKPGSTGPEPPIPQASPGPPGPLSQTPPMQRPVEPQEGPHKSLVAHRVPLKPYAAP
541  VPRSQSLQDQPTRNLAAFPASHDPDPAIPAPTATPSARGAVIRQNSDPTSEGPGPSPNPP
601  AWVRPDNEAPPKVPQRTSSIATALNTSGAGGSRPAQAVRARPRSNSAWQIYLQRRAERGT
661  PKPPGPPAQPPGPPNASSNPDLRRSDPGWERSDSVLPASHGHLPQAGSLERNRVGASSKL
721  DSSPVLSPGNKAKPDDHRSRPGRPADFVLLKERTLDEAPRPPKKAMDYSSSSEEVESSED
781  DEEEGEGGPAEGSRDTPGGRDGDTDSVSTMVVHDVEEITGTQPPYGGGTMVVQRTPEEER
841  NLLHADSNGYTNLPDVVQPSHSPTENSKGQSPPSKDGSGDYQSRGLVKAPGKSSFTMFVD
901  LGIYQPGGSGDSIPITALVGGEGTRLDQLQYDVRKGSVVNVNPTNTRAHSETPEIRKYKK
961  RFNSEILCAALWGVNLLVGTENGLMLLDRSGQGKVYGLIGRRRFQQMDVLEGLNLLITIS
1021 GKRNKLRVYYLSWLRNKILHNDPEVEKKQGWTTVGDMEGCGHYRVVKYERIKFLVIALKS
1081 SVEVYAWAPKPYHKFMAFKSFADLPHRPLLVDLTVEEGQRLKVIYGSSAGFHAADVDSGN
1141 SYDIYIPVHIQSQITPHAIIFLPNTDGMEMLLCYEDEGVYVNTYGRIIKDVVLQWGEMPT
1201 SVAYICSNQIMGWGEKAIEIRSVETGHLDGVFMHKRAQRLKFLCERNDKVFFASVRSGGS
1261 SQVYFMTLNRNCIMNW
```

FIG. 1 (CONTINUED)

Mink3c nucleotide sequence

ACCATTCTGGAAGCTCCCTAGAATCTCCTGGAATGCT
TAATGGACCTTTCCAGCACCGAAATTCAAGAATTATGACTCATCGGTCAGCAGAAAAGAC
CCTGCTGGGATCTTTGAGCTTGTGGAGGTGGTCGGCAATGGAACCTACGGACAGGTGTAC
AAGGGTCGGCATGTCAAGACGGGGCAGCTGGCTGCCATCAAGGTCATGGATGTCACGGAG
GACGAGGAGGAAGAGATCAAACAGGAGATCAACATGCTGAAAAAGTACTCTCACCACCGC
AACATCGCCACCTACTACGGAGCCTTCATCAAGAAGAGCCCCCGGGAAACGATGACCAG
CTCTGGCTGGTGATGGAGTTCTGTGGTGCTGGTTCAGTGACTGACCTGGTAAAGAACACA
AAAGGCAACGCCCTGAAGGAGGACTGTATCGCCTATATCTGCAGGGAGATCCTCAGGGGT
CTGGCCCATCTCCATGCCCACAAGGTGATCCATCGAGACATCAAGGGGCAGAATGTGCTG
CTGACAGAGAATGCTGAGGTCAAGCTAGTGGATTTTGGGGTGAGTGCTCAGCTGGACCGC
ACCGTGGGCAGACGGAACACTTTCATTGGGACTCCCTACTGGATGGCTCCAGAGGTCATC
GCCTGTGATGAGAACCCTGATGCCACCTATGATTACAGGAGTGATATTTGGTCTCTAGGA
ATCACAGCCATCGAGATGGCAGAGGGAGCCCCCCCTCTGTGTGACATGCACCCCATGCGA
GCCCTCTTCCTCATTCCTCGGAACCCTCCGCCCAGGCTCAAGTCCAAGAAGTGGTCTAAG
AAGTTCATTGACTTCATTGACACATGTCTCATCAAGACTTACCTGAGCCGCCCACCCACG
GAGCAGCTACTGAAGTTTCCCTTCATCCGGGACCAGCCCACGGAGCGGCAGGTCCGCATC
CAGCTTAAGGACCACATTGACCGATCCCGGAAGAAGCGGGGTGAGAAAGAGGAGACAGAA
TATGAGTACAGCGGCAGCGAGGAGGAAGATGACAGCCATGGAGAGGAAGGAGAGCCAAGC
TCCATCATGAACGTGCCTGGAGAGTCGACTCTACGCCGGGAGTTTCTCCGGCTCCAGCAG
GAAAATAAGAGCAACTCAGAGGCTTTAAAACAGCAGCAGCAGCTGCAGCAGCAGCAGCAG
CGAGACCCCGAGGCACACATCAAACACCTGCTGCACCAGCGGCAGCGGCGCATAGAGGAG
CAGAAGGAGGAGCGGCGCCGCGTGGAGGAGCAACAGCGGCGGGGGCGGGAGCAGCGGAAG
CTGCAGGAGAAGGAGCAGCAGCGGCGGCTGGAGGACATGCAGGCTCTGCGGCGGGAGGAG
GAGCGGCGGCAGGCGGAGCGTGAGCAGGAATACAAGCGGAAGCAGCTGGAGGAGCAGCGG
CAGTCAGAACGTCTCCAGAGGCAGCTGCAGCAGGAGCATGCCTACCTCAAGTCCCTGCAG
CAGCAGCAACAGCAGCAGCAGCTTCAGAAACAGCAGCAGCAGCAGCTCCTGCCTGGGGAC
AGGAAGCCCCTGTACCATTATGGTCGGGGCATGAATCCCGCTGACAAACCAGCCTGGGCC
CGAGAGGTAGAAGAGAGAACAAGGATGAACAAGCAGCAGAACTCTCCCTTGGCCAAGAGC
AAGCCAGGCAGCACGGGGCCTGAGCCCCCCATCCCCCAGGCCTCCCAGGGCCCCAGGA
CCCCTTTCCCAGACTCCTCCTATGCAGAGGCCGGTGGAGCCCAGGAGGGACCGCACAAG
AGCCTGGTGGCACACCGGGTCCCACTGAAGCCATATGCAGCACCTGTACCCCGATCCAG
TCCCTGCAGGACCAGCCCACCCGAAACCTGGCTGCCTTCCCAGCCTCCCATGACCCCGAC
CCTGCCATCCCCGCACCCACTGCCACGCCCAGTGCCCGAGGAGCTGTCATCCGCCAGAAT

FIG. 1 (CONTINUED)

```
TCAGACCCCACCTCTGAAGGACCTGGCCCCAGCCCGAATCCCCCAGCCTGGGTCCGCCCA
GATAACGAGGCCCCACCCAAGGTGCCTCAGAGGACCTCATCTATCGCCACTGCCCTTAAC
ACCAGTGGGGCCGGAGGGTCCCGGCCAGCCCAGGCAGTCCGTGCCAGACCTCGCAGCAAC
TCCGCCTGGCAAATCTATCTGCAAAGGCGGGCAGAGCGGGGCACCCCAAAGCCTCCAGGG
CCCCCTGCTCAGCCCCCTGGCCCGCCCAACGCCTCTAGTAACCCCGACCTCAGGAGGAGC
GACCCTGGCTGGGAACGCTCGGACAGCGTCCTTCCAGCCTCTCACGGGCACCTCCCCAG
GCTGGCTCACTGGAGCGGAACCGCGTGGGAGCCTCCTCCAAACTGGACAGCTCCCTGTG
CTCTCCCCTGGGAATAAAGCCAAGCCCGACGACCACCGCTCACGGCCAGGCCGGCCCGCA
GACTTTGTGTTGCTGAAAGAGCGGACTCTGGACGAGGCCCCTCGGCCTCCCAAGAAGGCC
ATGGACTACTCGTCGTCCAGCGAGGAGGTGGAAAGCAGTGAGGACGACGAGGAGGAAGGC
GAAGGCGGGCCAGCAGAGGGGAGCAGAGATACCCCTGGGGGCCGCGATGGGGATACAGAC
AGCGTCAGCACCATGGTGGTCCACGACGTCGAGGAGATCACCGGGACCCAGCCCCCATAC
GGGGGCGGCACCATGGTGGTCCAGCGCACCCCTGAAGAGGAGCGGAACCTGCTGCATGCT
GACAGCAATGGGTACACAAACCTGCCTGACGTGGTCCAGCCCAGCCACTCACCCACCGAG
AACAGCAAAGGCCAAAGCCCACCCTCGAAGGATGGGAGTGGTGACTACCAGTCTCGTGGG
CTGGTAAAGGCCCCTGGCAAGAGCTCGTTCACGATGTTTGTGGATCTAGGGATCTACCAG
CCTGGAGGCAGTGGGGACAGCATCCCCATCACAGCCCTAGTGGGTGGAGAGGGCACTCGG
CTCGACCAGCTGCAGTACGACGTGAGGAAGGGTTCTGTGGTCAACGTGAATCCCACCAAC
ACCCGGGCCCACAGTGAGACCCCTGAGATCCGGAAGTACAAGAAGCGATTCAACTCCGAG
ATCCTCTGTGCAGCCCTTTGGGGGGTCAACCTGCTGGTGGGCACGGAGAACGGGCTGATG
TTGCTGGACCGAAGTGGGCAGGGCAAGGTGTATGGACTCATTGGGCGGCGACGCTTCCAG
CAGATGGATGTGCTGGAGGGGCTCAACCTGCTCATCACCATCTCAGGGAAAAGGAACAAA
CTGCGGGTGTATTACCTGTCCTGGCTCCGGAACAAGATTCTGCACAATGACCCAGAAGTG
GAGAAGAAGCAGGGCTGGACCACCGTGGGGGACATGGAGGGCTGCGGGCACTACCGTGTT
GTGAAATACGAGCGGATTAAGTTCCTGGTCATCGCCCTCAAGAGCTCCGTGGAGGTGTAT
GCCTGGGCCCCCAAACCCTACCACAAATTCATGGCCTTCAAGTCCTTTGCCGACCTCCCC
CACCGCCCTCTGCTGGTCGACCTGACAGTAGAGGAGGGGCAGCGGCTCAAGGTCATCTAT
GGCTCCAGTGCTGGCTTCCATGCTGCGGATGTCGACTCGGGGAACAGCTATGACATCTAC
ATCCCTGTGCACATCCAGAGCCAGATCACGCCCCATGCCATCATCTTCCTCCCCAACACC
GACGGCATGGAGATGCTGCTGTGCTACGAGGACGAGGGTGTCTACGTCAACACGTACGGG
CGCATCATTAAGGATGTGGTGCTGCAGTGGGGGGAGATGCCTACTTCTGTGGCCTACATC
TGCTCCAACCAGATAATGGGCTGGGGTGAGAAAGCCATTGAGATCCGCTCTGTGGAGACG
GGCCACCTCGACGGGGTCTTCATGCACAAACGAGCTCAGAGGCTCAAGTTCCTGTGTGAG
CGGAATGACAAGGTGTTTTTTGCCTCAGTCCGCTCTGGGGGCAGCAGCCAAGTTTACTTC
ATGACTCTGAACCGTAACTGCATCATGAACTGGTGA
```

FIG. 1 (CONTNUED)

FIG. 10 TR5 and Bcl2 block Taxol-induced cleavage of Rb protein

MEK inhibitor restore the morphology of Mink3a infected MDA-MB-231 cells
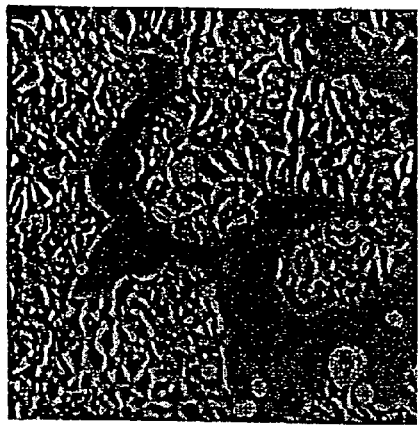
Mink3a +PD98059
Mink3a
MDA-MB-231
*FIG. 15*

SEQUENCE LISTING

```
<160> NUMBER OF SEQ ID NOS: 15

<210> SEQ ID NO 1
<211> LENGTH: 1312
<212> TYPE: PRT
<213> ORGANISM: Homo sapiens
<220> FEATURE:
<223> OTHER INFORMATION: Misshapen/NIK-related kinase isoform 3a

<400> SEQUENCE: 1

Met Gly Asp Pro Ala Pro Ala Arg Ser Leu Asp Asp Ile Asp Leu Ser
 1               5                  10                  15

Ala Leu Arg Asp Pro Ala Gly Ile Phe Glu Leu Val Glu Val Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Glu Asp Glu Glu Glu
        50                  55                  60

Glu Ile Lys Gln Glu Ile Asn Met Leu Lys Lys Tyr Ser His His Arg
    65                  70                  75                  80

Asn Ile Ala Thr Tyr Tyr Gly Ala Phe Ile Lys Lys Ser Pro Pro Gly
                85                  90                  95
```

```
Asn Asp Asp Gln Leu Trp Leu Val Met Glu Phe Cys Gly Ala Gly Ser
                100                 105                 110
Val Thr Asp Leu Val Lys Asn Thr Lys Gly Asn Ala Leu Lys Glu Asp
            115                 120                 125
Cys Ile Ala Tyr Ile Cys Arg Glu Ile Leu Arg Gly Leu Ala His Leu
        130                 135                 140
His Ala His Lys Val Ile His Arg Asp Ile Lys Gly Gln Asn Val Leu
145                 150                 155                 160
Leu Thr Glu Asn Ala Glu Val Lys Leu Val Asp Phe Gly Val Ser Ala
                165                 170                 175
Gln Leu Asp Arg Thr Val Gly Arg Arg Asn Thr Phe Ile Gly Thr Pro
            180                 185                 190
Tyr Trp Met Ala Pro Glu Val Ile Ala Cys Asp Glu Asn Pro Asp Ala
        195                 200                 205
Thr Tyr Asp Tyr Arg Ser Asp Ile Trp Ser Leu Gly Ile Thr Ala Ile
    210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Pro Pro Arg Leu Lys Ser Lys
                245                 250                 255
Lys Trp Ser Lys Lys Phe Ile Asp Phe Ile Asp Thr Cys Leu Ile Lys
            260                 265                 270
Thr Tyr Leu Ser Arg Pro Pro Thr Glu Gln Leu Leu Lys Phe Pro Phe
        275                 280                 285
Ile Arg Asp Gln Pro Thr Glu Arg Gln Val Arg Ile Gln Leu Lys Asp
    290                 295                 300
His Ile Asp Arg Ser Arg Lys Lys Arg Gly Glu Lys Glu Glu Thr Glu
305                 310                 315                 320
Tyr Glu Tyr Ser Gly Ser Glu Glu Asp Asp Ser His Gly Glu Glu
                325                 330                 335
Gly Glu Pro Ser Ser Ile Met Asn Val Pro Gly Glu Ser Thr Leu Arg
            340                 345                 350
Arg Glu Phe Leu Arg Leu Gln Gln Glu Asn Lys Ser Asn Ser Glu Ala
        355                 360                 365
Leu Lys Gln Gln Gln Gln Leu Gln Gln Gln Gln Arg Asp Pro Glu
    370                 375                 380
Ala His Ile Lys His Leu Leu His Gln Arg Gln Arg Ile Glu Glu
385                 390                 395                 400
Gln Lys Glu Glu Arg Arg Val Glu Glu Gln Arg Arg Glu Arg
                405                 410                 415
Glu Gln Arg Lys Leu Gln Glu Lys Glu Gln Gln Arg Arg Leu Glu Asp
            420                 425                 430
Met Gln Ala Leu Arg Arg Glu Glu Arg Arg Gln Ala Glu Arg Glu
        435                 440                 445
Gln Glu Tyr Lys Arg Lys Gln Leu Glu Glu Arg Gln Ser Glu Arg
    450                 455                 460
Leu Gln Arg Gln Leu Gln Gln Glu His Ala Tyr Leu Lys Ser Leu Gln
465                 470                 475                 480
Gln Gln Gln Gln Gln Gln Leu Gln Lys Gln Gln Gln Gln Leu
                485                 490                 495
Leu Pro Gly Asp Arg Lys Pro Leu Tyr His Tyr Gly Arg Gly Met Asn
            500                 505                 510
Pro Ala Asp Lys Pro Ala Trp Ala Arg Glu Val Glu Glu Arg Thr Arg
```

-continued

```
                515                 520                 525
Met Asn Lys Gln Gln Asn Ser Pro Leu Ala Lys Ser Lys Pro Gly Ser
    530                 535                 540

Thr Gly Pro Glu Pro Pro Ile Pro Gln Ala Ser Pro Gly Pro Pro Gly
545                 550                 555                 560

Pro Leu Ser Gln Thr Pro Pro Met Gln Arg Pro Val Glu Pro Gln Glu
                565                 570                 575

Gly Pro His Lys Ser Leu Gln Asp Gln Pro Thr Arg Asn Leu Ala Ala
            580                 585                 590

Phe Pro Ala Ser His Asp Pro Asp Pro Ala Ile Pro Ala Pro Thr Ala
        595                 600                 605

Thr Pro Ser Ala Arg Gly Ala Val Ile Arg Gln Asn Ser Asp Pro Thr
    610                 615                 620

Ser Glu Gly Pro Gly Pro Ser Pro Asn Pro Pro Ala Trp Val Arg Pro
625                 630                 635                 640

Asp Asn Glu Ala Pro Pro Lys Val Pro Gln Arg Thr Ser Ser Ile Ala
                645                 650                 655

Thr Ala Leu Asn Thr Ser Gly Ala Gly Gly Ser Arg Pro Ala Gln Ala
            660                 665                 670

Val Arg Ala Arg Pro Arg Ser Asn Ser Ala Trp Gln Ile Tyr Leu Gln
        675                 680                 685

Arg Arg Ala Glu Arg Gly Thr Pro Lys Pro Gly Pro Pro Ala Gln
    690                 695                 700

Pro Pro Gly Pro Pro Asn Ala Ser Ser Asn Pro Asp Leu Arg Arg Ser
705                 710                 715                 720

Asp Pro Gly Trp Glu Arg Ser Asp Ser Val Leu Pro Ala Ser His Gly
                725                 730                 735

His Leu Pro Gln Ala Gly Ser Leu Glu Arg Asn Arg Val Gly Ala Ser
            740                 745                 750

Ser Lys Leu Asp Ser Ser Pro Val Leu Ser Pro Gly Asn Lys Ala Lys
        755                 760                 765

Pro Asp Asp His Arg Ser Arg Pro Gly Arg Pro Ala Asp Phe Val Leu
    770                 775                 780

Leu Lys Glu Arg Thr Leu Asp Glu Ala Pro Arg Pro Lys Lys Ala
785                 790                 795                 800

Met Asp Tyr Ser Ser Ser Glu Glu Val Glu Ser Ser Glu Asp Asp
                805                 810                 815

Glu Glu Glu Gly Glu Gly Pro Ala Glu Gly Ser Arg Asp Thr Pro
            820                 825                 830

Gly Gly Arg Ser Asp Gly Asp Thr Asp Ser Val Ser Thr Met Val Val
        835                 840                 845

His Asp Val Glu Glu Ile Thr Gly Thr Gln Pro Pro Tyr Gly Gly Gly
    850                 855                 860

Thr Met Val Val Gln Arg Thr Pro Glu Glu Arg Asn Leu Leu His
865                 870                 875                 880

Ala Asp Ser Asn Gly Tyr Thr Asn Leu Pro Asp Val Val Gln Pro Ser
                885                 890                 895

His Ser Pro Thr Glu Asn Ser Lys Gly Gln Ser Pro Ser Lys Asp
            900                 905                 910

Gly Ser Gly Asp Tyr Gln Ser Arg Gly Leu Val Lys Ala Pro Gly Lys
        915                 920                 925

Ser Ser Phe Thr Met Phe Val Asp Leu Gly Ile Tyr Gln Pro Gly Gly
    930                 935                 940
```

Ser Gly Asp Ser Ile Pro Ile Thr Ala Leu Val Gly Glu Gly Thr
945                 950                 955                 960

Arg Leu Asp Gln Leu Gln Tyr Asp Val Arg Lys Gly Ser Val Asn
            965                 970                 975

Val Asn Pro Thr Asn Thr Arg Ala His Ser Glu Thr Pro Glu Ile Arg
            980                 985                 990

Lys Tyr Lys Lys Arg Phe Asn Ser Glu Ile Leu Cys Ala Ala Leu Trp
            995                 1000                1005

Gly Val Asn Leu Leu Val Gly Thr Glu Asn Gly Leu Met Leu Leu Asp
        1010                1015                1020

Arg Ser Gly Gln Gly Lys Val Tyr Gly Leu Ile Gly Arg Arg Arg Phe
1025                1030                1035                1040

Gln Gln Met Asp Val Leu Glu Gly Leu Asn Leu Leu Ile Thr Ile Ser
                1045                1050                1055

Gly Lys Arg Asn Lys Leu Arg Val Tyr Tyr Leu Ser Trp Leu Arg Asn
            1060                1065                1070

Lys Ile Leu His Asn Asp Pro Glu Val Glu Lys Lys Gln Gly Trp Thr
            1075                1080                1085

Thr Val Gly Asp Met Glu Gly Cys Gly His Tyr Arg Val Val Lys Tyr
        1090                1095                1100

Glu Arg Ile Lys Phe Leu Val Ile Ala Leu Lys Ser Ser Val Glu Val
1105                1110                1115                1120

Tyr Ala Trp Ala Pro Lys Pro Tyr His Lys Phe Met Ala Phe Lys Ser
                1125                1130                1135

Phe Ala Asp Leu Pro His Arg Pro Leu Leu Val Asp Leu Thr Val Glu
            1140                1145                1150

Glu Gly Gln Arg Leu Lys Val Ile Tyr Gly Ser Ser Ala Gly Phe His
            1155                1160                1165

Ala Val Asp Val Asp Ser Gly Asn Ser Tyr Asp Ile Tyr Ile Pro Val
        1170                1175                1180

His Ile Gln Ser Gln Ile Thr Pro His Ala Ile Ile Phe Leu Pro Asn
1185                1190                1195                1200

Thr Asp Gly Met Glu Met Leu Leu Cys Tyr Glu Asp Glu Gly Val Tyr
                1205                1210                1215

Val Asn Thr Tyr Gly Arg Ile Ile Lys Asp Val Val Leu Gln Trp Gly
            1220                1225                1230

Glu Met Pro Thr Ser Val Ala Tyr Ile Cys Ser Asn Gln Ile Met Gly
            1235                1240                1245

Trp Gly Glu Lys Ala Ile Glu Ile Arg Ser Val Glu Thr Gly His Leu
        1250                1255                1260

Asp Gly Val Phe Met His Lys Arg Ala Gln Arg Leu Lys Phe Leu Cys
1265                1270                1275                1280

Glu Arg Asn Asp Lys Val Phe Phe Ala Ser Val Arg Ser Gly Gly Ser
                1285                1290                1295

Ser Gln Val Tyr Phe Met Thr Leu Asn Arg Asn Cys Ile Met Asn Trp
            1300                1305                1310

<210> SEQ ID NO 2
<211> LENGTH: 3951
<212> TYPE: DNA
<213> ORGANISM: Homo sapiens
<220> FEATURE:
<223> OTHER INFORMATION: misshapen/NIK-related kinase isoform 3a

<400> SEQUENCE: 2

```
gcccttatgg gcgacccagc ccccgcccgc agcctggacg acatcgacct gtccgccctg      60
cgggaccctg ctgggatctt tgagcttgtg gaggtggtcg gcaatggaac ctacggacag     120
gtgtacaagg gtcggcatgt caagacgggg cagctggctg ccatcaaggt catggatgtc     180
acggaggacg aggaggaaga gatcaaacag gagatcaaca tgctgaaaaa gtactctcac     240
caccgcaaca tcgccaccta ctacggagcc ttcatcaaga gagcccccc gggaaacgat      300
gaccagctct ggctggtgat ggagttctgt ggtgctggtt cagtgactga cctggtaaag     360
aacacaaaag gcaacgccct gaaggaggac tgtatcgcct atatctgcag ggagatcctc     420
agggtctgg cccatctcca tgcccacaag gtgatccatc gagacatcaa ggggcagaat      480
gtgctgctga cagagaatgc tgaggtcaag ctagtggatt ttgggggtgag tgctcagctg     540
gaccgcaccg tgggcagacg gaacactttc attgggactc cctactggat ggctccagag     600
gtcatcgcct gtgatgagaa ccctgatgcc acctatgatt acaggagtga tatttggtct     660
ctaggaatca cagccatcga gatggcagag ggagccccc ctctgtgtga catgcacccc      720
atgcgagccc tcttcctcat tcctcggaac cctccgccca ggctcaagtc caagaagtgg     780
tctaagaagt tcattgactt cattgacaca tgtctcatca agacttacct gagccgccca     840
cccacggagc agctactgaa gtttcccttc atcccgggac cagcccacgg agcggcaggt     900
ccgcatccag cttaaggacc acattgaccg atcccggaag aagcggggtg agaaagagga     960
gacagaatat gagtacagcg gcagcgagga ggaagatgac agccatggag aggaaggaga    1020
gccaagctcc atcatgaacg tgcctggaga gtcgactcta cgccgggagt ttctccggct    1080
ccagcaggaa aataagagca actcagaggc tttaaaacag cagcagcagc tgcagcagca    1140
gcagcagcga gaccccgagg cacacatcaa acacctgctg caccagcggc agcggcgcat    1200
agaggagcag aaggaggagc ggcgccgcgt ggaggagcaa cagcggcggg agcgggagca    1260
gcggaagctg caggagaagg agcagcagcg gcggctggag gacatgcagg ctctgcggcg    1320
ggaggaggag cggcggcagg cggagcgtga gcaggaatac aagcggaagc agctggagga    1380
gcagcggcag tcagaacgtc tccagaggca gctgcagcag gagcatgcct acctcaagtc    1440
cctgcagcag cagcaacagc agcagcagct tcagaaacag cagcagcagc agctcctgcc    1500
tggggacagg aagcccctgt accattatgg tcggggcatg atcccgctga caaaccagcc    1560
tgggcccgag aggtagaaga gagaacaagg atgaacaagc agcagaactc tcccttggcc    1620
aagagcaagc caggcagcac ggggcctgag ccccccatcc cccaggcctc ccagggccc    1680
ccaggacccc tttcccagac tcctcctatg cagaggccgg tggagcccca ggagggaccg    1740
cacaagtccc tgcaggacca gcccacccga aacctggctg ccttcccagc ctcccatgac    1800
cccgaccctg ccatccccgc acccactgcc acgcccagtg cccgaggagc tgtcatccgc    1860
cagaattcag accccacctc tgaaggacct ggccccagcc cgaatccccc agcctgggtc    1920
cgcccagata cgaggccccc acccaaggtg cctcagagga cctcatctat cgccactgcc    1980
cttaacacca gtggggccgg agggtcccgg ccagcccagg cagtccgtgc agacctcgc     2040
agcaactccg cctggcaaat ctatctgcaa aggcgggcag agcggggcac cccaaagcct    2100
ccagggcccc ctgctcagcc ccctggcccg cccaacgcct ctagtaaccc cgatcaggag    2160
gagcgaccct ggctgggaac gctcggacag cgtccttcca gcctctcacg ggcacctccc    2220
ccaggctggc tcactggagc ggaaccgcgt gggagcctcc tccaaactgg acagctcccc    2280
tgtgctctcc cctgggaata aagccaagcc cgacgaccac cgctcacggc caggccggcc    2340
```

```
cgcagacttt gtgttgctga aagagcggac tctggacgag gcccctcggc ctcccaagaa    2400
ggccatggac tactcgtcgt ccagcgagga ggtggaaagc agtgaggacg acgaggagga    2460
aggcgaaggc gggccagcag aggggagcag agatacccct gggggccgca gcgatgggga    2520
tacagacagc gtcagcacca tggtggtcca cgacgtcgag gagatcaccg ggacccagcc    2580
cccatacggg ggcggcacca tggtggtcca gcgcaccccct gaagaggagc ggaacctgct    2640
gcatgctgac agcaatgggt acacaaacct gcctgacgtg gtccagccca gccactcacc    2700
caccgagaac agcaaaggcc aaagcccacc ctcgaaggat gggagtggtg actaccagtc    2760
tcgtgggctg gtaaaggccc ctggcaaaga gctcgttcac gatgtttgtg atctaggga    2820 tctaccagcc tggaggcagt ggggacagca tccccatcac agccctagtg ggtggagagg    2880
gcactcggct cgaccagctg cagtacgacg tgaggaaggg ttctgtggtc aacgtgaatc    2940
ccaccaacac ccgggcccac agtgagaccc tgagatccg aagtacaag aagcgattca    3000 actccgagat cctctgtgca gccctttggg ggtcaacct gctggtgggc acggagaacg    3060
ggctgatgtt gctggaccga agtgggcagg gcaaggtgta tggactcatt gggcggcgac    3120
gcttccagca gatggatgtg ctggaggggc tcaacctgct catcaccatc tcagggaaaa    3180
ggaacaaact gcgggtgtat tacctgtcct ggctccggaa caagattctg cacaatgacc    3240
cagaagtgga gaagaagcag ggctggacca ccgtgggggga catggagggc tgcgggcact    3300
accgtgttgt gaaatacgag cggattaagt tcctggtcat cgccctcaag agctccgtgg    3360
aggtgtatgc ctgggcccccc aaaccctacc acaaattcat ggccttcaag tcctttgccg    3420
acctccccca ccgccctctg ctggtcgacc tgacagtaga ggaggggcag cggctcaagg    3480
tcatctatgg ctccagtgct ggcttccatg ctgtggatgt cgactcgggg aacagctatg    3540
acatctacat ccctgtgcac atccagagcc agatcacgcc ccatgccatc atcttcctcc    3600
ccaacaccga cggcatggag atgctgctgt gctacgagga cgagggtgtc tacgtcaaac    3660
acgtacgggc gcatcattaa ggatgtggtg ctgcagtggg gggagatgcc tacttctgtg    3720
gcctacatct gctccaacca gataatgggc tggggtgaga aagccattga gatccgctct    3780
gtggagacgg gccacctcga cggggtcttc atgcacaaac gagctcagag gctcaagttc    3840
ctgtgtgagc ggaatgacaa ggtgtttttt gcctcagtcc gctctggggg cagcagccaa    3900
gtttacttca tgactctgaa ccgtaactgc atcatgaact ggtgaaaggg c    3951
```

<210> SEQ ID NO 3
<211> LENGTH: 792
<212> TYPE: PRT
<213> ORGANISM: Homo sapiens
<220> FEATURE:
<223> OTHER INFORMATION: misshapen/NIK-related kinase isoform 3b

<400> SEQUENCE: 3

```
Met Asp Val Thr Glu Asp Glu Glu Glu Ile Lys Gln Glu Ile Asn
 1               5                  10                  15
Met Leu Lys Lys Tyr Ser His His Arg Asn Ile Ala Thr Tyr Tyr Gly
                20                  25                  30
Ala Phe Ile Lys Lys Ser Pro Pro Gly Asn Asp Asp Gln Leu Trp Leu
            35                  40                  45
Val Met Glu Phe Cys Gly Ala Gly Ser Val Thr Asp Leu Val Lys Asn
        50                  55                  60
Thr Lys Gly Asn Ala Leu Lys Glu Asp Cys Ile Ala Tyr Ile Cys Arg
    65                  70                  75                  80
Glu Ile Leu Arg Gly Leu Ala His Leu His Lys Val His Lys Ile His
                    85                  90                  95
Arg Asp Ile Lys Gly Gln Asn Val Leu Leu Thr Glu Asn Ala Glu Val
                100                 105                 110
Lys Leu Val Asp Phe Gly Val Ser Ala Gln Leu Asp Arg Thr Val Gly
```

-continued

```
                115                 120                 125
    Arg Arg Asn Thr Phe Ile Gly Thr Pro Tyr Trp Met Ala Pro Glu Val
        130                 135                 140
    Ile Ala Cys Asp Glu Asn Pro Asp Ala Thr Tyr Asp Tyr Arg Ser Asp
145                 150                 155                 160
    Ile Trp Ser Leu Gly Ile Thr Ala Ile Glu Met Ala Glu Gly Ala Pro
                165                 170                 175
    Pro Leu Cys Asp Met His Pro Met Arg Ala Leu Phe Leu Ile Pro Arg
                180                 185                 190
    Asn Pro Pro Arg Leu Lys Ser Lys Lys Trp Ser Lys Lys Phe Ile
                195                 200                 205
    Asp Phe Ile Asp Thr Cys Leu Ile Lys Thr Tyr Leu Ser Arg Pro Pro
        210                 215                 220
    Thr Glu Gln Leu Leu Lys Phe Pro Phe Ile Arg Asp Gln Pro Thr Glu
225                 230                 235                 240
    Arg Gln Val Arg Ile Gln Leu Lys Asp His Ile Asp Arg Ser Arg Lys
                245                 250                 255
    Lys Arg Gly Glu Lys Glu Glu Thr Glu Tyr Glu Tyr Ser Gly Ser Glu
                260                 265                 270
    Glu Glu Asp Asp Ser His Gly Glu Glu Gly Pro Ser Ser Ile Met
                275                 280                 285
    Asn Val Pro Gly Glu Ser Thr Leu Arg Arg Glu Phe Leu Arg Leu Gln
        290                 295                 300
    Gln Glu Asn Lys Ser Asn Ser Glu Ala Leu Lys Gln Gln Gln Leu
305                 310                 315                 320
    Gln Gln Gln Gln Gln Arg Asp Pro Glu Ala His Ile Lys His Leu Leu
                325                 330                 335
    His Gln Arg Gln Arg Ile Glu Glu Gln Lys Glu Glu Arg Arg Arg
                340                 345                 350
    Val Glu Glu Gln Gln Arg Arg Glu Arg Glu Gln Arg Lys Leu Gln Glu
                355                 360                 365
    Lys Glu Gln Gln Arg Arg Leu Glu Asp Met Gln Ala Leu Arg Arg Glu
                370                 375                 380
    Glu Glu Arg Arg Gln Ala Glu Arg Gln Glu Glu Tyr Lys Arg Lys Gln
385                 390                 395                 400
    Leu Glu Glu Gln Arg Gln Ser Glu Arg Leu Arg Gln Leu Gln Gln
                405                 410                 415
    Glu His Ala Tyr Leu Lys Ser Leu Gln Gln Gln Gln Gln Gln Gln
                420                 425                 430
    Leu Gln Lys Gln Gln Gln Gln Leu Leu Pro Gly Asp Arg Lys Pro
                435                 440                 445
    Leu Tyr His Tyr Gly Arg Gly Met Asn Pro Ala Asp Lys Pro Ala Trp
        450                 455                 460
    Ala Arg Glu Val Glu Glu Arg Thr Arg Met Asn Lys Gln Gln Asn Ser
465                 470                 475                 480
    Pro Leu Ala Lys Ser Lys Pro Gly Ser Thr Gly Pro Glu Pro Pro Ile
                485                 490                 495
    Pro Gln Ala Ser Pro Gly Pro Pro Gly Pro Leu Ser Gln Thr Pro Pro
                500                 505                 510
    Met Gln Arg Pro Val Glu Pro Gln Glu Gly Pro His Lys Ser Leu Val
                515                 520                 525
    Ala His Arg Val Pro Leu Lys Pro Tyr Ala Ala Pro Val Pro Arg Ser
        530                 535                 540
    Gln Ser Leu Gln Asp Gln Pro Thr Arg Asn Leu Ala Ala Phe Pro Ala
545                 550                 555                 560
    Ser His Asp Pro Asp Pro Ala Ile Pro Ala Pro Thr Ala Thr Pro Ser
                565                 570                 575
    Ala Arg Gly Ala Val Ile Arg Gln Asn Ser Asp Pro Thr Ser Glu Gly
                580                 585                 590
    Pro Gly Pro Ser Pro Asn Pro Pro Ala Trp Val Arg Pro Asp Asn Glu
                595                 600                 605
    Ala Pro Pro Lys Val Pro Gln Arg Thr Ser Ser Ile Ala Thr Ala Leu
        610                 615                 620
    Asn Thr Ser Gly Ala Gly Gly Ser Arg Pro Ala Gln Ala Val Arg Ala
625                 630                 635                 640
    Arg Pro Arg Ser Asn Ser Ala Trp Gln Ile Tyr Leu Gln Arg Arg Ala
                645                 650                 655
    Glu Arg Gly Thr Pro Lys Pro Pro Gly Pro Pro Ala Gln Pro Pro Gly
                660                 665                 670
    Pro Pro Asn Ala Ser Ser Asn Pro Asp Leu Arg Arg Ser Asp Pro Gly
                675                 680                 685
    Trp Glu Arg Ser Asp Ser Val Leu Pro Ala Ser His Gly His Leu Pro
        690                 695                 700
    Gln Ala Gly Ser Leu Glu Arg Asn Arg Val Gly Ala Ser Ser Lys Leu
705                 710                 715                 720
    Asp Ser Ser Pro Val Leu Ser Pro Gly Asn Lys Ala Lys Pro Asp Asp
                725                 730                 735
    His Arg Ser Arg Pro Gly Arg Pro Ala Val Ser His Leu Val Ala Gly
                740                 745                 750
```

```
Met Ala Cys Leu Ile Leu Val Trp Gly Leu Ala Ser Gly Cys Trp Val
            755                 760                 765
Ser Gly Val Gly Ser Pro Leu Ile Tyr Arg Glu Gly Leu Trp Gly Trp
        770                 775                 780
Arg Asp Trp Cys Phe Ser Trp Cys
785                 790

<210> SEQ ID NO 4
<211> LENGTH: 4411
<212> TYPE: DNA
<213> ORGANISM: Homo sapiens
<220> FEATURE:
<223> OTHER INFORMATION: misshapen/NIK-related kinase isoform 3b

<400> SEQUENCE: 4
gcccttacca ttctggaagc tccctagaat ctcctggaat gcttaatgga cctttccagc    60
accgaaattc aagaattatg actcatcggt cagcagaaaa gaccctgctg ggatctttga   120
gcttgtggag gtggtcggca atggaaccta cggacaggtg tacaagggtc ggcatgtcaa   180
gacggggcag ctggctgcca tcaaggtcat ggatgtcacg gaggacgagg aggaagagat   240
caaacaggag atcaacatgc tgaaaaagta ctctccaccac cgcaacatcg ccacctacta   300
cggagccttg atcaagaaga ccccccgggg aaacgatgac cagctctggc tggtgatgga   360
gttctgtggt gctggttcag tgactgacct ggtaaagaaa cacaaaaggc aacgccctga   420
aggaggactg tatcgctata tctgcaggga gatcctgcag ggtctggccc atctccatgc   480
ccacaaggtg atccatcgag acatcaaggg gcagaatgtg ctgctgacag agaatgctga   540
ggtcaagcta gtggatttg gggtgagtgc tcagctggac cgcaccgtgg gcaacggaac   600
actttcattg ggactcccta ctggatggct ccagaggtca tcgcctgtga tgagaaccct   660
gatgccacct atgattacag gagtgatatt tggtctctag gaatcacagc catcgagatg   720
gcagagggag ccccccctct gtgtgacatg caccccatgc gagccctctt cctcattcct   780
cggaaccctc cgcccaggct caagtccaag aagtggtcta agaagttcat tgacttcatt   840
gacacatgtc tcatcaagac ttacctgagc cgcccaccca cggagcagct actgaagttt   900
cccttcatcc gggaccagcc cacggagcgg caggtccgca tccagcttaa ggaccacatt   960
gaccgatccc ggaagaagcg gggtgagaaa gaggagacag aatatgagta cagcggcagc  1020
gaggaggaag atgacagcca tggagaggaa ggagagccaa gctccatcat gaacgtgcct  1080
ggagagtcga ctctacgccg ggagttttctc cggctccagc aggaaaataa gagcaactca  1140
gaggctttaa aacagcagca gctgcagcag cagcagcagc gagaccccga ggcacacatc  1200
aaacacctgc tgcaccagcg gcagcggcgc atagaggagc agaaggagga gcggcgccgc  1260
gtggaggagc aacagcggcg ggagcgggag cagcggaagc tgcaggagaa ggagcagcag  1320
cggcggctgg aggacatgca ggctctgcgg cgggaggagg agcggcggca ggcggagcgt  1380
gagcaggaat acaagcggaa gcagctggag gagcagcgca gtcagaacgt ctccagaggc  1440
agctgcagca ggagcatgcc tacctccagt ccctgcaagc agcagcaaca gcagcagcag  1500
cttcagaaac agcagcagca gcagctcctg cctggggaca ggaagcccct gtaccattat  1560
ggtcgggca tgaacccgct gacaaaccag cctgggcccg agaggtagaa gagagaacaa  1620
ggatgaacaa gcagcagaac tctcccttgg ccaagagcag gccaggcagc acgggccctg  1680
agccccccat cccccaggcc tccccaggc ccccaggacc ctttccaga ctcctcctat  1740
gcagaggccg gtggagcccc aggagggacc gcacaagagc ctggtggcac accgggtccc  1800
actgaagcca tatgcagcac ctgtaccccg atcccagtcc ctgcaggacc agcccacccg  1860
aaacctggct gccttcccag cctcccatga ccccgacct gccatcccg caacccactg  1920
ccacgcccag tgcccgagga gctgtcatcc gccagaattc agaccccacc tctgaaggac  1980
ctggccccag cccgaatccc ccagcctggg tccgcccaga taacgaggcc ccacccaagg  2040
tgcctcagag gacctctcta tcgccactgc ccttaacacc agtgggggccg gaggtccccg  2100
gccagcccag gcagtccgtg ccagaccctcg cagcaactcc gcctggcaaa tctatctgca  2160
aaggcggggca gagcggggca ccccaaaagcc tccagggccc cctctcagcc ccctggcccg  2220
cccaacgcct ctagtaaccc cgacctcagg aggagcgaac cctggctggg aacgctcgga  2280
cagcgtcctt ccagcctctc acgggcacct ccccaggct ggctcactgg agcggaaccg  2340
cgtgggagcc tccccaaact ggacagctcc cctgtgctct cccctgggaa taaagccaag  2400
cccgacgacc accgctcacg gccaggccgg cccgcagtga gtcacctggt gcaggcatg  2460
gcctgcctca tcctggtttg gggcttagcc tcagggtgct gggtgtcagg ggtgggtct  2520
ccgctgatct accgagaagg gctgtgggga tgagggact ggtgcttctc atggtgctac  2580
cttcctaac ctctcctcca acctctctcc tacctctct tctggctctt tcttcccctg  2640
cggcccctcc cagagctata agcgagcaat tggtgaggtt agtgagatgg gcctgcttgt  2700
gggagcccct cctgtcgccc tgcggggcgt cccggcaccc tttgtctacc tccacccagg  2760
cccagcttct ccctgcccct cacgtggctc ctccctgcag gactttgtgt tgctgaaaga  2820
gcggactctg gacgaggccc ctcggcctcc aagaaggcc atggactact cgtcgtccag  2880
cgaggaggtg aaaagcagtg aggacgacga ggaggaaggc gaaggcggcc cagcagaggg  2940
agcagagat acccctgggg gccgcagcga tgggatcca gacagcgtca gcaccatggt  3000
ggtccacgac tcgaggagat caccgggacc cagccccat acgggggcgg caccatggtg  3060
gtccagcgca cccctgaaga ggagcggaac ccgctgcatg ctgacagcaa tgggtacaca  3120
aacctgcctg acgtggtcca gcccagccac tcacccaccg agaacagcaa aggccaaagc  3180
ccaccctcga aggatgggac tggtgactac cagtctccgt ggtggtgaaa gcccctggga  3240
aagagctcgt tcacgatgtt tgtgcatca gggatctacc agcctggagg cagtggggac  3300
agcatcccca tcacagccct agtgggtgga gagcactc ggctcgacca gctgcagtac  3360
gacgtgagga agggttctgt ggtcaacgtg aatcccacca caccccggggc ccacagtgag  3420
accccctgaga tccgaagta caagagcga ttcaactccg agatcctctg gcagccctt  3480
tgggggtca acctgctggt gggcacggag aacgggctga gtgctggga ccgaagtggg  3540
caggacaagg tgtatggact cattgggcga cgacgcttcc agcagatgga tgtgctggaa  3600
gggctcaacc tgctcatcac catctcaggg aaaaggaaca aactggcggg tgtattacct  3660
gtcctggctc cggaacaaga ttctgcacaa tgacccgaaa gtggagaaga agcagggctg  3720
```

-continued

```
gaccaccgtg ggggacatgg agggctgcgg gcactaccgt gttgtgaaat acgagcggat 3780
taagttcctg gtcatcgccc tcaagagctc cgtggaggtg taatgcctgg gcccccaaac 3840
cctaccacaa attcatggcc ttcaagtcct ttgccgacct cccccaccgc cctctgctgg 3900
tcgacctgac agtagaggag gggcagcggc tcaaggtcat ctatggctcc agtgctggct 3960
tccaatgctg tggatgtcga ctcggggaac agctatgaca tctacatccc tgtgcacatc 4020
cagagagcca gatcacgccc catgccatca tcttcctccc caacaccgac ggcatggaga 4080
tgctgctgtg ctacgaggac gagggtgtct acgtcaacac gtacgggcgc atcattaagg 4140
atgtggtgct gcagtggggg gagatgccta cttctgtgcc ctacactgtc tccaaccaga 4200
taatgggctg gggtgagaaa gccattgaga tccggctctg tggagacggg ccacctcgac 4260
ggggtcttca tgcacaaacg agcttcagag gctcaagttc ctgtgtgagc ggaatgacaa 4320
ggtgtttttt gcctcagtcc gctctggggg cagcagccaa gtttacttca tgactctgaa 4380
ccgtaactgc atcatgaact ggtgaaaggg c                            4411
```

<210> SEQ ID NO 5
<211> LENGTH: 1276
<212> TYPE: PRT
<213> ORGANISM: Homo sapiens
<220> FEATURE:
<223> OTHER INFORMATION: misshapen/NIK-related kinase isoform 3c
<220> FEATURE:
<223> OTHER INFORMATION: misshapen/NIK-related kinase isoform 3c

<400> SEQUENCE: 5

```
Met Asp Val Thr Glu Asp Glu Glu Glu Ile Lys Gln Glu Ile Asn
 1               5                  10                  15

Met Leu Lys Lys Tyr Ser His His Arg Asn Ile Ala Thr Tyr Tyr Gly
            20                  25                  30

Ala Phe Ile Lys Lys Ser Pro Pro Gly Asn Asp Asp Gln Leu Trp Leu
        35                  40                  45

Val Met Glu Phe Cys Gly Ala Gly Ser Val Thr Asp Leu Val Lys Asn
    50                  55                  60

Thr Lys Gly Asn Ala Leu Lys Glu Asp Cys Ile Ala Tyr Ile Cys Arg
65                  70                  75                  80

Glu Ile Leu Arg Gly Leu Ala His Leu His Ala His Lys Val Ile His
                85                  90                  95

Arg Asp Ile Lys Gly Gln Asn Val Leu Leu Thr Glu Asn Ala Glu Val
            100                 105                 110

Lys Leu Val Asp Phe Gly Val Ser Ala Gln Leu Asp Arg Thr Val Gly
        115                 120                 125

Arg Arg Asn Thr Phe Ile Gly Thr Pro Tyr Trp Met Ala Pro Glu Val
    130                 135                 140

Ile Ala Cys Asp Glu Asn Pro Asp Ala Thr Tyr Asp Tyr Arg Ser Asp
145                 150                 155                 160

Ile Trp Ser Leu Gly Ile Thr Ala Ile Glu Met Ala Glu Gly Ala Pro
                165                 170                 175

Pro Leu Cys Asp Met His Pro Met Arg Ala Leu Phe Leu Ile Pro Arg
            180                 185                 190

Asn Pro Pro Pro Arg Leu Lys Ser Lys Lys Trp Ser Lys Lys Phe Ile
        195                 200                 205

Asp Phe Ile Asp Thr Cys Leu Ile Lys Thr Tyr Leu Ser Arg Pro Pro
    210                 215                 220

Thr Glu Gln Leu Leu Lys Phe Pro Phe Ile Arg Asp Gln Pro Thr Glu
225                 230                 235                 240

Arg Gln Val Arg Ile Gln Leu Lys Asp His Ile Asp Arg Ser Arg Lys
                245                 250                 255

Lys Arg Gly Glu Lys Glu Glu Thr Glu Tyr Glu Tyr Ser Gly Ser Glu
            260                 265                 270

Glu Glu Asp Asp Ser His Gly Glu Gly Glu Pro Ser Ser Ile Met
        275                 280                 285
```

-continued

```
Asn Val Pro Gly Glu Ser Thr Leu Arg Arg Glu Phe Leu Arg Leu Gln
    290                 295                 300

Gln Glu Asn Lys Ser Asn Ser Glu Ala Leu Lys Gln Gln Gln Gln Leu
305                 310                 315                 320

Gln Gln Gln Gln Gln Arg Asp Pro Glu Ala His Ile Lys His Leu Leu
                325                 330                 335

His Gln Arg Gln Arg Arg Ile Glu Glu Gln Lys Glu Glu Arg Arg Arg
            340                 345                 350

Val Glu Glu Gln Gln Arg Arg Gly Arg Glu Gln Arg Lys Leu Gln Glu
        355                 360                 365

Lys Glu Gln Gln Arg Arg Leu Glu Asp Met Gln Ala Leu Arg Arg Glu
370                 375                 380

Glu Glu Arg Arg Gln Ala Glu Arg Glu Gln Glu Tyr Lys Arg Lys Gln
385                 390                 395                 400

Leu Glu Glu Gln Arg Gln Ser Glu Arg Leu Gln Arg Gln Leu Gln Gln
                405                 410                 415

Glu His Ala Tyr Leu Lys Ser Leu Gln Gln Gln Gln Gln Gln Gln Gln
            420                 425                 430

Leu Gln Lys Gln Gln Gln Gln Leu Leu Pro Gly Asp Arg Lys Pro
        435                 440                 445

Leu Tyr His Tyr Gly Arg Gly Met Asn Pro Ala Asp Lys Pro Ala Trp
    450                 455                 460

Ala Arg Glu Val Glu Glu Arg Thr Arg Met Asn Lys Gln Gln Asn Ser
465                 470                 475                 480

Pro Leu Ala Lys Ser Lys Pro Gly Ser Thr Gly Pro Glu Pro Pro Ile
                485                 490                 495

Pro Gln Ala Ser Pro Gly Pro Gly Pro Leu Ser Gln Thr Pro Pro
            500                 505                 510

Met Gln Arg Pro Val Glu Pro Gln Gly Pro His Lys Ser Leu Val
        515                 520                 525

Ala His Arg Val Pro Leu Lys Pro Tyr Ala Ala Pro Val Pro Arg Ser
    530                 535                 540

Gln Ser Leu Gln Asp Pro Thr Arg Asn Leu Ala Ala Phe Pro Ala
545                 550                 555                 560

Ser His Asp Pro Asp Pro Ala Ile Pro Ala Pro Thr Ala Thr Pro Ser
                565                 570                 575

Ala Arg Gly Ala Val Ile Arg Gln Asn Ser Asp Pro Thr Ser Glu Gly
            580                 585                 590

Pro Gly Pro Ser Pro Asn Pro Ala Trp Val Arg Pro Asp Asn Glu
        595                 600                 605

Ala Pro Pro Lys Val Pro Gln Arg Thr Ser Ser Ile Ala Thr Ala Leu
    610                 615                 620

Asn Thr Ser Gly Ala Gly Gly Ser Arg Pro Ala Gln Ala Val Arg Ala
625                 630                 635                 640

Arg Pro Arg Ser Asn Ser Ala Trp Gln Ile Tyr Leu Gln Arg Arg Ala
                645                 650                 655

Glu Arg Gly Thr Pro Lys Pro Pro Gly Pro Pro Ala Gln Pro Pro Gly
            660                 665                 670

Pro Pro Asn Ala Ser Ser Asn Pro Asp Leu Arg Arg Ser Asp Pro Gly
        675                 680                 685

Trp Glu Arg Ser Asp Ser Val Leu Pro Ala Ser His Gly His Leu Pro
    690                 695                 700

Gln Ala Gly Ser Leu Glu Arg Asn Arg Val Gly Ala Ser Ser Lys Leu
```

```
                705                 710                 715                 720
Asp Ser Ser Pro Val Leu Ser Pro Gly Asn Lys Ala Lys Pro Asp Asp
                    725                 730                 735

His Arg Ser Arg Pro Gly Arg Pro Ala Asp Phe Val Leu Leu Lys Glu
                740                 745                 750

Arg Thr Leu Asp Glu Ala Pro Arg Pro Pro Lys Lys Ala Met Asp Tyr
            755                 760                 765

Ser Ser Ser Glu Glu Val Glu Ser Ser Glu Asp Asp Glu Glu Glu
        770                 775                 780

Gly Glu Gly Gly Pro Ala Glu Gly Ser Arg Asp Thr Pro Gly Gly Arg
785                 790                 795                 800

Asp Gly Asp Thr Asp Ser Val Ser Thr Met Val Val His Asp Val Glu
                805                 810                 815

Glu Ile Thr Gly Thr Gln Pro Pro Tyr Gly Gly Thr Met Val Val
                820                 825                 830

Gln Arg Thr Pro Glu Glu Arg Asn Leu Leu His Ala Asp Ser Asn
            835                 840                 845

Gly Tyr Thr Asn Leu Pro Asp Val Val Gln Pro Ser His Ser Pro Thr
    850                 855                 860

Glu Asn Ser Lys Gly Gln Ser Pro Pro Ser Lys Asp Gly Ser Gly Asp
865                 870                 875                 880

Tyr Gln Ser Arg Gly Leu Val Lys Ala Pro Gly Lys Ser Ser Phe Thr
                885                 890                 895

Met Phe Val Asp Leu Gly Ile Tyr Gln Pro Gly Ser Gly Asp Ser
                900                 905                 910

Ile Pro Ile Thr Ala Leu Val Gly Gly Glu Gly Thr Arg Leu Asp Gln
            915                 920                 925

Leu Gln Tyr Asp Val Arg Lys Gly Ser Val Val Asn Val Asn Pro Thr
        930                 935                 940

Asn Thr Arg Ala His Ser Glu Thr Pro Glu Ile Arg Lys Tyr Lys Lys
945                 950                 955                 960

Arg Phe Asn Ser Glu Ile Leu Cys Ala Ala Leu Trp Gly Val Asn Leu
                965                 970                 975

Leu Val Gly Thr Glu Asn Gly Leu Met Leu Leu Asp Arg Ser Gly Gln
            980                 985                 990

Gly Lys Val Tyr Gly Leu Ile Gly Arg Arg Arg Phe Gln Gln Met Asp
        995                 1000                1005

Val Leu Glu Gly Leu Asn Leu Leu Ile Thr Ile Ser Gly Lys Arg Asn
    1010                1015                1020

Lys Leu Arg Val Tyr Tyr Leu Ser Trp Leu Arg Asn Lys Ile Leu His
1025                1030                1035                1040

Asn Asp Pro Glu Val Glu Lys Lys Gln Gly Trp Thr Thr Val Gly Asp
                1045                1050                1055

Met Glu Gly Cys Gly His Tyr Arg Val Val Lys Tyr Glu Arg Ile Lys
            1060                1065                1070

Phe Leu Val Ile Ala Leu Lys Ser Ser Val Glu Val Tyr Ala Trp Ala
        1075                1080                1085

Pro Lys Pro Tyr His Lys Phe Met Ala Phe Lys Ser Phe Ala Asp Leu
    1090                1095                1100

Pro His Arg Pro Leu Leu Val Asp Leu Thr Val Glu Glu Gly Gln Arg
1105                1110                1115                1120

Leu Lys Val Ile Tyr Gly Ser Ser Ala Gly Phe His Ala Ala Asp Val
                1125                1130                1135
```

```
Asp Ser Gly Asn Ser Tyr Asp Ile Tyr Ile Pro Val His Ile Gln Ser
         1140                1145                1150
Gln Ile Thr Pro His Ala Ile Ile Phe Leu Pro Asn Thr Asp Gly Met
     1155                1160                1165
Glu Met Leu Leu Cys Tyr Glu Asp Glu Gly Val Tyr Val Asn Thr Tyr
     1170                1175                1180
Gly Arg Ile Ile Lys Asp Val Val Leu Gln Trp Gly Glu Met Pro Thr
1185                1190                1195                1200
Ser Val Ala Tyr Ile Cys Ser Asn Gln Ile Met Gly Trp Gly Glu Lys
             1205                1210                1215
Ala Ile Glu Ile Arg Ser Val Glu Thr Gly His Leu Asp Gly Val Phe
         1220                1225                1230
Met His Lys Arg Ala Gln Arg Leu Lys Phe Leu Cys Glu Arg Asn Asp
     1235                1240                1245
Lys Val Phe Phe Ala Ser Val Arg Ser Gly Gly Ser Ser Gln Val Tyr
 1250                1255                1260
Phe Met Thr Leu Asn Arg Asn Cys Ile Met Asn Trp
1265                1270                1275

<210> SEQ ID NO 6
<211> LENGTH: 4032
<212> TYPE: DNA
<213> ORGANISM: Homo sapiens
<220> FEATURE:
<223> OTHER INFORMATION: misshapen/NIK-related Kinase isoform c

<400> SEQUENCE: 6
accattctgg aagctcccta gaatctcctg gaatgcttaa tggacctttc cagcaccgaa      60
attcaagaat tatgactcat cggtcagcag aaaagaccct gctgggatct tgagcttgt     120
ggaggtggtc ggcaatggaa cctacggaca gtgtacaag ggtcggcatg tcaagacggg     180
gcagctggct gccatcaagg tcatggatgt cacggaggac gaggaggaag agatcaaaca     240
ggagatcaac atgctgaaaa agtactctca ccaccgcaac atcgccacct actacgagc     300
cttcatcaag aagagccccc cggaaaacga tgaccagctc tggctggtga tggagttctg     360
tggtgctggt tcagtgactg acctggtaaa gaacacaaaa ggcaacgccc tgaaggagga     420
ctgtatcgcc tatatctgca gggagatcct caggggtctg gcccatctcc atgcccacaa     480
ggtgatccat cgagacatca gggggcagaa tgtgctgctg acagagaatg ctgaggtcaa     540
gctagtggat tttggggtga gtgctcagct ggaccgcacc gtgggcagac ggaacacttt     600
cattgggact ccctactgga tggctccaga ggtcatcgcc tgtgatgaga accctgatgc     660
cacctatgat tacaggagtg atatttggtc tctaggaatc acagccatcg agatggcaga     720
gggagccccc cctctgtgtg acatgcaccc catgcgagcc ctcttcctca ttcctcggaa     780
cccctccgcc aggctcaagt ccaagaagtg gtctaagaag ttcattgact tcattgacac     840
atgtctcatc aagacttacc tgagccgccc acccacggag cagctactga gtttcccctt     900
catccgggac cagcccacgg agcggcaggt ccgcatccag cttaaggacc acattgaccg     960
atccccggaag aagcggggtg agaaagagga gacagaatat gagtacagcg gcagcgagga    1020
ggaagatgac agccatggag aggaaggaga gccaagctcc atcatgaacg tgcctggaga    1080
gtcgactcta cgccgggagt ttctccggct ccagcaggaa aataagagca actcagaggc    1140
tttaaaacag cagcagcagc tgcagcagca gcagcagcga cccccgagg cacacatcaa    1200
acacctgctg caccagcggc agcggcgcat agaggagcag aaggaggagc ggcgccgcgt    1260
```

-continued

```
ggaggagcaa cagcggcggg ggcgggagca gcggaagctg caggagaagg agcagcagcg      1320
gcggctggag gacatgcagg ctctgcggcg ggaggaggag cggcggcagg cggagcgtga      1380
gcaggaatac aagcggaagc agctggagga gcagcggcag tcagaacgtc tccagaggca      1440
gctgcagcag gagcatgcct acctcaagtc cctgcagcag cagcaacagc agcagcagct      1500
tcagaaacag cagcagcagc agctcctgcc tggggacagg aagcccctgt accattatgg      1560
tcggggcatg aatcccgctg acaaaccagc ctgggcccga gaggtagaag agagaacaag      1620
gatgaacaag cagcagaact ctcccttggc caagagcaag ccaggcagca cggggcctga      1680 gcccccatc ccccaggcct ccccagggcc cccaggaccc ctttcccaga ctcctcctat       1740
gcagaggccg gtggaggccc aggagggacc gcacaagagc ctggtggcac accgggtccc      1800
actgaagcca tatgcagcac ctgtaccccg atcccagtcc ctgcaggacc agcccacccg      1860
aaacctggct gccttcccag cctcccatga ccccgaccct gccatccccg cacccactgc      1920
cacgcccagt gcccgaggag ctgtcatccg ccagaattca gaccccacct ctgaaggacc      1980
tggccccagc ccgaatcccc cagcctgggt tccgccagat aacgaggccc cacccaaggt      2040
gcctcagagg acctcatcta tcgccactgc ccttaacacc agtggggccg gagggtcccg      2100
gccagcccag gcagtccgtg ccagacctcg cagcaactcc gcctggcaaa tctatctgca      2160
aaggcgggca gagcggggca ccccaaagcc tccagggccc cctgctcagc cccctggccc      2220
gcccaacgcc tctagtaacc ccgacctcag gaggagcgac cctggctggg aacgctcgga      2280
cagcgtcctt ccagcctctc acgggcacct ccccccaggct ggctcactgg agcggaaccg     2340
cgtgggagcc tcctccaaac tggacagctc ccctgtgctc tcccctggga ataaagccaa      2400
gcccgacgac caccgctcac ggccaggccg gcccgcagac tttgtgttgc tgaaagagcg      2460
gactctggac gaggcccctc ggcctcccaa gaaggccatg gactactcgt cgtccagcga      2520
ggaggtggaa agcagtgagg acgacgagga ggaaggcgaa ggcgggccag cagaggggag      2580
cagagatacc cctgggggcc gcgatgggga tacagacagc gtcagcacca tggtggtcca      2640
cgacgtcgag gagatcaccg ggacccagcc cccatacggg ggcggcacca tggtggtcca      2700
gcgcacccct gaagaggagc ggaacctgct gcatgctgac agcaatgggt acacaaacct      2760
gcctgacgtg gtccagccca gccactcacc caccgagaac agcaaaggcc aaagcccacc      2820
ctcgaaggat gggagtggtg actaccagtc tcgtgggctg gtaaaggccc ctggcaagag      2880
ctcgttcacg atgtttgtgg atctagggat ctaccagcct ggaggcagtg gggacagcat      2940
ccccatcaca gccctagtgg gtggagaggg cactcggctc gaccagctgc agtacgacgt      3000
gaggaagggt tctgtggtca acgtgaatcc caccaacacc cgggcccaca gtgagacccc      3060
tgagatccgg aagtacaaga agcgattcaa ctccgagatc ctctgtgcag ccctttgggg      3120
ggtcaacctg ctggtgggca cggagaacgg gctgatgttg ctggaccgaa gtgggcaggg      3180
caaggtgtat ggactcattg gcggcgacg cttccagcag atggatgtgc tggaggggct       3240
caacctgctc atcaccatct cagggaaaag gaacaaactg cgggtgtatt acctgtcctg      3300
gctccggaac aagattctgc acaatgaccc agaagtggag aagaagcagg gctggaccac      3360
cgtgggggac atggagggct gcgggcacta ccgtgttgtg aaatacgagc ggattaagtt      3420
cctggtcatc gccctcaaga gctccgtgga ggtgtatgcc tgggccccca aaccctacca      3480
caaattcatg gccttcaagt cctttgccga cctcccccac cgccctctgc tggtcgacct      3540
gacagtagag gaggggcagc ggctcaaggt catctatggc tccagtgctg gcttccatgc      3600
```

| | |
|---|---|
| tgcggatgtc gactcgggga acagctatga catctacatc cctgtgcaca tccagagcca | 3660 |
| gatcacgccc catgccatca tcttcctccc caacaccgac ggcatggaga tgctgctgtg | 3720 |
| ctacgaggac gagggtgtct acgtcaacac gtacgggcgc atcattaagg atgtggtgct | 3780 |
| gcagtggggg gagatgccta cttctgtggc ctacatctgc tccaaccaga taatgggctg | 3840 |
| gggtgagaaa gccattgaga tccgctctgt ggagacgggc cacctcgacg gggtcttcat | 3900 |
| gcacaaacga gctcagaggc tcaagttcct gtgtgagcgg aatgacaagg tgttttttgc | 3960 |
| ctcagtccgc tctgggggca gcagccaagt ttattcatga ctctgaaccg taactgcatc | 4020 |
| atgaactggt ga | 4032 |

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: HA epitope
      tag
<220> FEATURE:

<400> SEQUENCE: 7

Ala Tyr Pro Tyr Asp Val Pro Asp Tyr Ala
 1               5                  10

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide for mutation
<220> FEATURE:

<400> SEQUENCE: 8
agcttgcagc catcagggtt atggatgtca c                             31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide for mutation

<400> SEQUENCE: 9
gtgacatcca taaccttgat ggctgcaagc t                             31

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Myc epitope
      tag
<220> FEATURE:

<400> SEQUENCE: 10

Ala Ser Met Glu Gln Lys Leu Ile Ser Glu Glu Asp Leu Asn
 1               5                  10

<210> SEQ ID NO 11
<211> LENGTH: 6
<212> TYPE: PRT
<213> ORGANISM: Artificial Sequence
<220> FEATURE:

```
<223> OTHER INFORMATION: Description of Artificial Sequence: NIK
      intermediate domain (aa574-579)

<400> SEQUENCE: 11

Pro Cys Pro Pro Ser Arg
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: NIK
      intermediate domain (aa 611-616)

<400> SEQUENCE: 12

Pro Arg Val Pro Val Arg
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: NIK
      intermediate domain (aa 562-567)

<400> SEQUENCE: 13

Pro Asn Leu Pro Pro Arg
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: NIK
      intermediate domain (aa 647-652)

<400> SEQUENCE: 14

Pro Pro Leu Pro Thr Arg
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: NIK
      intermediate domain (aa 670-675)

<400> SEQUENCE: 15

Pro Lys Val Pro Gln Arg
 1               5
```

GERMINAL CENTER KINASE PROTEINS, COMPOSITIONS, AND METHODS OF USE

CROSS-REFERENCES TO RELATED APPLICATIONS

This application is a National Stage of International Application No. PCT/US2003/033845, filed Oct. 21, 2002, which is a continuation of U.S. application Ser. No. 10/029,115, filed Oct. 19, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention provides compositions and methods for modulating cell proliferation, survival, morphology, and migration. Nucleic acids encoding proteins and proteins so encoded which are capable of modulating proliferation, survival, morphology and migration in mammalian cells are provided. Compositions and methods for the treatment of disorders related to cell proliferation, survival, morphology and migration are also provided. Prophylactics and methods for the prevention of such disorders are also provided. Also provided are compositions and methods for diagnostic and prognostic determination of such disorders. Further provided are assays for the identification of bioactive agents capable of modulating proliferation, survival, morphology and migration in mammalian cells.

BACKGROUND OF THE INVENTION

Cells cycle through various stages of growth, starting with the M phase, where mitosis and cytoplasmic division (cytokinesis) occurs. The M phase is followed by the G1 phase, in which the cells resume a high rate of biosynthesis and growth. The S phase begins with DNA synthesis, and ends when the DNA content of the nucleus has doubled. The cell then enters G2 phase, which ends when mitosis starts, signaled by the appearance of condensed chromosomes. Terminally differentiated cells are arrested in the G1 phase, and no longer undergo cell division.

The hallmark of a malignant cell is uncontrolled proliferation. This phenotype is acquired through the accumulation of gene mutations, the majority of which promote passage through the cell cycle. Cancer cells ignore growth regulatory signals and remain committed to cell division. Classic oncogenes, such as ras, lead to inappropriate transition from G1 to S phase of the cell cycle, mimicking proliferative extracellular signals. Cell cycle checkpoint controls ensure faithful replication and segregation of the genome. The loss of cell cycle checkpoint control results in genomic instability, greatly accelerating the accumulation of mutations which drive malignant transformation. Thus, modulating cell cycle checkpoint pathways and other such pathways with therapeutic agents could exploit the differences between normal and tumor cells, both improving the selectivity of radio- and chemotherapy, and leading to novel cancer treatments, including treatment for metastatic cancers. As another example, it would be useful to control entry into apoptosis.

On the other hand, it is also sometimes desirable to enhance proliferation of cells in a controlled manner. For example, proliferation of cells is useful in wound healing and where growth of tissue is desirable. Thus, identifying modulators which promote, enhance or deter the inhibition of proliferation is desirable.

Proteins of general interest that have been reported on include kinases. The Ste20 family of kinases can be divided into two structurally distinct subfamilies. The first subfamily contains a C-terminal catalytic domain and an N-terminal binding site for the small G proteins Rac1 and Cdc42 (Herskowitz, *Cell*, 80:187-197 (1995)). The yeast serine/threonine kinase Ste20 and its mammalian homologue, p21 Activated Kinase 1 (PAK1), belong to this subfamily. Ste20 initiates a mitogen-activated protein kinase (MAPK) cascade that includes Ste11 (MAPKKK), Ste7 (MAPKK), and FUS3/KSS1 (MAPK) in response to activation of the small G protein Cdc42, as well as signals from the hetero-trimeric G proteins coupled to pheromone receptors (Herskowitz, *Cell*, 80:187-197 (1995)). Similar to Ste20, PAK1 has been reported to be a Cdc42 and Rac1 effector molecule and specifically regulates the c-Jun N-terminal kinase (JNK) pathway, one of the mammalian MAPK pathways (Bagrodia, et. al., *J. Biol. Chem.*, 270:27995-27998 (1995); Kyriakis, et al., *J. Biol. Chem.*, 271:24313-24316 (1996)). The JNK pathway is activated by a variety of stress inducing agents, including osmotic and heat shock, UV irradiation, protein inhibitors and pro-inflammatory cytokines such as tumor necrosis factor (TNF) (Ip, et al., *Curr. Opin. Cell Biol.*, 10:205-219 (1998)). JNKs are activated through threonine and tyrosine phosphorylation by MEK4 and MEK7 (MAPKK), which are in turn phosphorylated and activated by MAPKKKs including MEK kinase 1 (MEKK1), and mixed lineage kinases MLK2 and MLK3 (Ip, et al., *Curr. Opin. Cell Biol.*, 10:205-219 (1998)). In addition to the activation of the JNK pathway, PAK1 has also been reported to be a regulator of the actin cytoskeleton (Sells, et al., *Curr. Biol.*, 7:202-210 (1997)).

The second subgroup of Ste20 family of kinases is represented by the family of germinal center kinases (GCK) (Kyriakis, *J. Biol. Chem.*, 274:5259-5262 (1999)). In contrast to Ste20 and PAK1, GCK family members have an N-terminal kinase domain and a C-terminal regulatory region. Many GCK family members, including GCK, germinal center kinase related protein (GCKR), meatopoietic protein kinase (HPK) 1, GCK-like kinase (GLK), HPK/GCK-like kinase (HGK) and NCK interacting kinase (NIK), have also been reported to activate the JNK pathway when overexpressed in 293 cells (Pombo, et al., *Nature*, 377:750-754 (1995); Shi, et al., *J. Biol. Chem.*, 272:32102-32107 (1997); Kiefer, et al., *EMBO J.*, 15:7013-7025 (1996); Diener, et al., *Proc. Natl. Acad. Sci. USA*, 94:9687-9692 (1997); Yao, et al., *J. Biol. Chem.*, 274:2118-2125 (1999); Su, et al., *EMBO J.*, 16:1279-1290 (1997)). Among those, GCK and GCKR have been implicated in mediating TNF-induced JNK activation through TNF receptor associated factor 2 (Traf2) (Pombo, et al., *Nature*, 377:750-754 (1995); Diener, et al., *Proc. Natl. Acad. Sci. USA*, 94:9687-9692 (1997); Yuasa, et al., *J. Biol. Chem.*, 273:22681-22692 (1998)). NCK interacting kinase (NIK) interacts with the SH2-SH3 domain containing adapter protein NCK and has been proposed to link protein tyrosine kinase signals to JNK activation (Su, et al., *EMBO J.*, 16:1279-1290 (1997)).

A kinase related to TNIK has been reported on. MINK (misshapen/NIKs-related kinase) protein and nucleic acid have been previously described (Ippeita et. al., FEBS Letters, 469:19-23, 2000). MINK1 is a gck kinase family member which is upregulated during brain development (Ippeita et. al., FEBS Letters, 469:19-23, 2000).

One study reports on a GCK family kinase from *Dictyostelium* that can phosphorylate Severin in vitro. (Eichinger, et al., *J. Biol. Chem.*, 273:12952-12959 (1998)). Severin is an F-actin fragmenting and capping enzyme that regulates *Dictyostelium* motility. TNIK, a mammalian GCK, has been shown to regulate the cytoskeleton, particularly to destabilize F-actin (Fu et al., JBC 274:30729-30737, 1999).

The Rho, rac and cdc42 small GTPases have been shown to regulate actin polymerization and the formation of multimolecular focal complexes (for example, see Nobes et al., Cell 81:53-62, 1995, and references therein; incorporated herein by reference). Further, PAK1 has been shown to regulate actin cytoskeleton organization, possibly through the phosphorylation and inhibition of the myosin light chain kinase Sanders et al., Science 283:2083-2085, 1999).

In addition, intracellular signaling mechanisms affecting cytoskeletal organization and underlying cell migration in response to extracellular cues have been studied in some detail (for review, see Maghazachi et al., Int. J. Biochem. Cell Biol. 32:931-943, 2000).

Several kinases and other intracellular signaling molecules have also been implicated in the control of apoptosis and cell survival in mammalian cells. For example, the JNK family of kinases has been implicated in both apoptosis and cell survival, the particular effect being dependent on the cellular context (for review, see Ip et al., Curr. Opin. Cell Biol. 10:205-219, 1998).

The role of GCKs in the immune system is of particular interest. Although GCKs are expressed widely, in B lymphocytic follicular tissue, GCK expression is largely restricted to the germinal center (Katz et al., JBC 269: 16802-16809, 1994). In germinal centers, B lymphocytes undergo differentiation and selection, which is induced in part by ligands including members of the TNF family. These ligands activate GCKs which in turn activate other protein kinases that induce lymphocyte development (reviewed in Kyriakis, JBC 274:5259-5262, 1999).

The integrity of intracellular signal transduction pathways and their appropriate regulation is essential for B cell and T cell development and function. An understanding of these signaling pathways is therefore desirable to provide means for therapeutically modulating lymphocyte function in a variety of disorders characterized by hyper immune responses (e.g. auto-immune disorders) or hypo immune responses (e.g. immunodeficiency disorders). Such understanding is also desirable to provide for the modulation of normal but undesirable immune responses, for example following transplant immunosuppressive agents are desirable.

The modulation of signal transduction, proliferation, apoptosis, morphological change, metastasis, and migration in mammalian cells is desirable, for example for the treatment of cancer, such as immune dysfunction, and for immunosuppression. Accordingly, compositions and methods for modulating these processes in mammalian cells are desirable.

SUMMARY OF THE INVENTION

The present invention provides compositions and methods for modulating proliferation, survival, migration, metastasis, morphology, cytoskeletal organization and intracellular signal transduction in mammalian cells. Nucleic acids encoding proteins and proteins so encoded which are capable of modulating proliferation, survival, metastasis, migration, morphology, cytoskeletal organization and intracellular signal transduction in mammalian cells are provided. Compositions and methods for the treatment of disorders related to cell proliferation, survival, morphology, metastasis, and migration are also provided. Prophylactics and methods for the prevention of such disorders are also provided. Also provided are compositions and methods for diagnostic and prognostic determination of such disorders. Further provided are assays for the identification of bioactive agents capable of modulating signal transduction, proliferation, survival, metastasis, morphology and migration in mammalian cells.

Accordingly, the present invention provides MINK3 nucleic acids, including nucleic acids encoding MINK3 protein, which are capable of modulating proliferation, survival, migration, morphology, metastasis, cytoskeletal organization and intracellular signal transduction in mammalian cells. Also provided herein are MINK3 antisense nucleic acids which are capable of modulating proliferation, survival, migration, morphology, metastasis, cytoskeletal organization and intracellular signal transduction in mammalian cells. Also provided herein are MINK3 proteins, including dominant negative MINK3 proteins, which are capable of modulating proliferation, survival, migration, metastasis, morphology, cytoskeletal organization and intracellular signal transduction in mammalian cells.

MINK (misshapen/NIKs-related kinase) proteins and nucleic acids having homology to the MINK3 proteins and nucleic acids described herein have been previously described (Ippeita et. al., FEBS Letters, 469:19-23, 2000). For example, MINK1 is a gck kinase family member which is upregulated during brain development (Ippeita et. al., FEBS Letters, 469:19-23, 2000).

In one aspect, the invention is directed to MINK3 proteins. In another aspect, the invention is directed to recombinant MINK3 nucleic acids, including nucleic acids encoding MINK3 proteins. In a further aspect, the invention is directed to recombinant MINK3 antisense nucleic acids comprising nucleic acid sequences complementary to the nucleic acid sequences of MINK3 nucleic acids or fragments thereof.

In a preferred embodiment of the invention, the MINK3 nucleic acid comprises a nucleic acid sequence selected from the group consisting of the nucleic acid sequences set forth in SEQ ID NOs:2, 4, and 6, or complements thereof.

In another preferred embodiment, the MINK3 nucleic acid comprises a nucleic acid sequence having at least about 90% identity, more preferably at least about 95% identity to a nucleic acid sequence selected from the group consisting of the nucleic acid sequences set forth in SEQ ID NOs:2, 4, and 6, or complements thereof.

In another preferred embodiment, the MINK3 nucleic acid will hybridize under high stringency conditions to a nucleic acid comprising a nucleic acid sequence selected from the group consisting of the nucleic acid sequences set forth in SEQ ID NOs:2, 4, and 6, or complements thereof.

In a preferred embodiment, the MINK3 antisense nucleic acid comprises a nucleic acid sequence complementary to the nucleic acid sequence set forth in SEQ ID NO: 2, more preferably to the nucleic acid sequence set forth by a fragment of SEQ ID NO:2, more preferably to the nucleic acid sequence set forth by nucleotides 2804-3187 in SEQ ID NO:2.

In a preferred embodiment, the MINK3 antisense nucleic acid has a nucleic acid sequence that consists essentially of the complement of the nucleic acid sequence set forth by nucleotides 2804-3187 in SEQ ID NO:2.

In a preferred embodiment, the MINK3 antisense nucleic acid hybridizes to MINK3a and MINK1 nucleic acids.

In a preferred embodiment, the MINK3 nucleic acid comprises a nucleic acid sequence encoding MINK3 protein. Preferably MINK3 protein so encoded will bind Nck.

In a preferred embodiment, the MINK3 nucleic acid comprises a nucleic acid sequence encoding a MINK3 protein comprising an amino acid sequence selected from the group consisting of the amino acid sequences set forth in SEQ ID NOs:1, 3, and 5.

In a preferred embodiment, the MINK3 nucleic acid comprises a nucleic acid sequence encoding a MINK3 protein comprising an amino acid sequence having at least about 90% identity, more preferably at least about 95% identity, to an amino acid sequence selected from the group consisting of the amino acid sequences set forth in SEQ ID NOs:1, 3, AND 5.

In one aspect, the present invention provides MINK3 proteins encoded by MINK3 nucleic acids described herein.

In one aspect, the invention provides three isoforms of MINK3 protein and nucleic acid, namely MINK3a, MINK3b and MINK3c, comprising amino acid and nucleic acid sequences as described herein. MINK3b and MINK3c nucleic acids have a frameshift relative to MINK3a. As a consequence, MINK3b and MINK3c proteins are kinase dead proteins.

In one aspect, the invention provides MINK3 antisense nucleic acids. In a preferred embodiment, the MINK3 antisense nucleic acid will inhibit growth factor-induced activation of an extracellular signal response kinase (ERK), preferably EGF-induced ERK activation.

In a preferred embodiment, the MINK3 antisense nucleic acid will inhibit proliferation in a mammalian cell, preferably a cancer cell.

In a preferred embodiment, the MINK3 antisense nucleic acid will inhibit aberrant cell proliferation, for example as occurs in cancer. Preferably such aberrant cell proliferation involves aberrant ERK and/or JNK pathway activation.

In a preferred embodiment, the MINK3 antisense nucleic acid will inhibit growth factor-dependent proliferation in a mammalian cell. Preferably such growth factor-dependent proliferation is EGF-dependent.

In a preferred embodiment, the MINK3 antisense nucleic acid will inhibit phosphorylation of c-JUN N-terminal kinase (JNK) and/or ERK.

In a preferred embodiment, the MINK3 antisense nucleic acid will inhibit activation of JNK and/or ERK.

In a preferred embodiment, the MINK3 antisense nucleic acid will inhibit the JNK signal transduction pathway and/or the ERK signal transduction pathway in a mammalian cell. Preferably the mammalian cell is a cancer cell and/or a lymphocyte.

In a preferred embodiment, the MINK3 antisense nucleic acid will inhibit taxol-induced cleavage of the retinoblastoma protein (Rb) and apoptosis in a mammalian cell. In a preferred embodiment, the MINK3 antisense nucleic acid will promote survival in a mammalian cell following exposure to taxol.

In a preferred embodiment, the MINK3 antisense nucleic acid will inhibit the transcription promoting activity of AP-1 in a mammalian cell. In a preferred embodiment, the MINK3 antisense nucleic acid will inhibit transcriptional activation by one or more AP-1 response elements.

In a preferred embodiment, a MINK3 inhibitor will inhibit cellular migration and or metastasis, preferably in a transformed, malignant, cancerous, or tumor cell.

In one embodiment, a MINK3 nucleic acid has an activity opposite to that of a MINK3 antisense nucleic acid.

In another aspect of the invention, expression vectors are provided. The expression vectors comprise one or more MINK3 nucleic acids described herein operably linked to regulatory sequences recognized by a host cell transformed with the nucleic acid. Further provided herein are host cells comprising the vectors and MINK3 nucleic acids provided herein. Moreover, provided herein are processes for producing MINK3 protein comprising culturing a host cell under conditions suitable for expression of the MINK3 protein. In one embodiment, the process includes recovering the MINK3 protein.

In one aspect, the invention is directed to MINK3 proteins.

In a preferred embodiment of the invention, the MINK3 protein comprises an amino acid sequence selected from the group consisting of the amino acid sequences set forth in SEQ ID NOs:1, 3, and 5.

In another preferred embodiment, the MINK3 protein comprises an amino acid sequence having at least about 90% identity, more preferably at least about 95% identity to an amino acid sequence selected from the group consisting of the amino acid sequences set forth in SEQ ID NOs:1, 3, and 5.

In a preferred embodiment, the MINK3 protein will bind to NCK protein, such as Nck protein comprising the amino acid sequence set forth at Genbank accession number AAD13752.

In another preferred embodiment, the MINK3 protein will effect a change in morphology in a mammalian cell, preferably a cancer cell. In a preferred embodiment, the morphology affecting activity of MINK3 protein is MEK-dependent.

In a preferred embodiment, the MINK3 protein will disrupt actin filaments in a mammalian cell, preferably a cancer cell.

In a preferred embodiment, the MINK3 protein will phosphorylate JNK and/or ERK.

In a preferred embodiment, the MINK3 protein will activate JNK and/or ERK.

In a preferred embodiment, the MINK3 protein will activate the JNK signal transduction pathway and/or the ERK signal transduction pathway in a mammalian cell.

In another preferred embodiment, the MINK3 protein will induce cell cycle progression and proliferation in a mammalian cell.

In a preferred embodiment, the MINK3 protein comprises a germinal center kinase domain (GCK) (sometimes referred to herein, and in the literature, as a "CNH" domain) as that set forth by amino acids 994-1292 or 994-1290 in SEQ ID NO:1.

In a preferred embodiment, the MINK3 protein comprises a catalytic serine/threonine kinase domain, as that set forth by amino acids 25-289 in SEQ ID NO:1.

In a preferred embodiment, the MINK3 protein comprises a catalytic tyrosine kinase domain, as that set forth by amino acids 26-286 in SEQ ID NO:1.

In a preferred embodiment, the MINK3 protein provided herein comprises an ATP-binding domain, such as that set forth by amino acids 32-54 in SEQ ID NO:1.

In one aspect, the invention is directed to dominant negative MINK3 proteins. A dominant negative MINK3 protein will antagonize at least one MINK3 protein activity.

In a preferred embodiment, the dominant negative MINK3 protein will inhibit the JNK signal transduction pathway and/or the ERK signal transduction pathway in a mammalian cell. Preferably the mammalian cell is a cancer cell.

In a preferred embodiment, the dominant negative MINK3 protein will inhibit growth factor-induced ERK activation in a mammalian cell, preferably a cancer cell.

In a preferred embodiment, the dominant negative MINK3 protein will inhibit growth factor-dependent proliferation in a mammalian cell.

In another preferred embodiment, the dominant negative MINK3 protein will inhibit cell cycle progression and proliferation in a mammalian cell. Preferably the mammalian cell is a cancer cell and/or a lymphocyte.

In a preferred embodiment, the dominant negative MINK3 protein is a kinase dead MINK3 protein variant as described herein.

In a preferred embodiment, the dominant negative kinase dead MINK3 protein variant has a mutation in an ATP-binding domain. Preferably the non-mutant ATP-binding domain of the non-variant MINK3 protein (non-variant with respect to ATP-binding domain) comprises the amino acid sequence set forth by amino acids 32-54 in SEQ ID NO:1. In a preferred embodiment, the dominant negative kinase dead MINK3 protein variant has a substitution mutation in the ATP binding domain at a position corresponding to K54 in SEQ ID NO:1. In a preferred embodiment, expression of kinase dead MINK3 reduces invasion potential of a cell.

In one aspect, the invention is directed to methods for screening candidate bioactive agents for an ability to bind to MINK3 proteins. In a preferred embodiment, the methods comprise combining a MINK3 protein and a candidate bioactive agent and determining the binding of candidate bioactive agent to MINK3 protein.

In another aspect, the invention is directed to methods for screening a candidate bioactive agent for an ability to interfere with the binding of a MINK3 protein. In one embodiment, the interference is between the binding of anti-MINK3 antibody and MINK3 protein. In a preferred embodiment, the interference is between the binding of a MINK3 protein and an Nck protein such as an Nck protein comprising the amino acid sequence set forth at Genbank accession number AAD13752. In one embodiment, such a method comprises combining a MINK3 protein, a candidate bioactive agent and an Nck protein, and determining the binding of the MINK3 protein to Nck protein in the presence of candidate bioactive agent. Preferably, the binding of MINK3 to Nck is determined in the presence and absence of candidate bioactive agent. If desired, the MINK3 protein and the Nck protein can be combined first.

In another aspect, the invention is directed to methods for screening candidate bioactive agents for an ability to modulate MINK3 protein activity. In one embodiment, candidate bioactive agents identified in these assays include small organic molecules, peptides, cyclic peptides, nucleic acids, antibodies, antisense nucleic acids, RNAi, and ribozymes. In a preferred embodiment, the methods comprise combining a MINK3 protein and a candidate bioactive agent and determining the effect of the candidate agent on the activity of MINK3 protein. In a preferred embodiment, a library of candidate bioactive agents is added to a plurality of cells comprising a recombinant nucleic acid encoding a MINK3 protein and MINK3 protein activity is determined. Preferably, MINK3 protein activity is determined in the presence and absence of candidate bioactive agent.

In one aspect, the invention is directed to methods for screening for a bioactive agent capable of modulating JNK phosphorylation and/or activation. In one aspect, the invention is directed to methods for screening for a bioactive agent capable of modulating the JNK signal transduction pathway. In a preferred embodiment, the methods comprise contacting a candidate bioactive agent to a mammalian cell comprising a recombinant MINK3 nucleic acid encoding a MINK3 protein and a JNK protein and determining JNK activity in the presence of candidate agent. In a preferred embodiment, JNK activity is determined in the presence and absence of candidate agent. The recombinant MINK3 nucleic acid is expressed in said mammalian cell and will activate JNK protein in the absence of candidate bioactive agent. In a preferred embodiment, the encoded MINK3 protein comprises an amino acid sequence having at least about 90% identity to an amino acid sequence selected from the group consisting of the amino acid sequences set forth in SEQ ID NOs:1, 3, and 5. A decrease in the activity of JNK protein in the presence of candidate bioactive agent indicates that the candidate bioactive agent is capable of modulating JNK activity.

In one aspect, the invention is directed to methods for screening for a bioactive agent capable of modulating ERK phosphorylation and/or activation. In one aspect, the invention is directed to methods for screening for a bioactive agent capable of modulating the ERK signal transduction pathway. In a preferred embodiment, the methods comprise contacting a candidate bioactive agent to a mammalian cell comprising a recombinant MINK3 nucleic acid encoding a MINK3 protein and a ERK protein and determining ERK activity in the presence of candidate agent. In a preferred embodiment, ERK activity is determined in the presence and absence of candidate agent. The recombinant MINK3 nucleic acid is expressed in said mammalian cell and will activate ERK protein in the absence of candidate bioactive agent. In a preferred embodiment, the encoded MINK3 protein comprises an amino acid sequence having at least about 90% identity to an amino acid sequence selected from the group consisting of the amino acid sequences set forth in SEQ ID NOs:1, 3, and 5. A decrease in the activity of ERK protein in the presence of candidate bioactive agent indicates that the candidate bioactive agent is capable of modulating ERK activity.

In a preferred embodiment, the methods comprise contacting a mammalian cell with a growth factor which will activate JNK and/or ERK. In a preferred embodiment, the growth factor used in epidermal growth factor (EGF).

In one aspect, the invention is directed to methods for screening candidate bioactive agents for an ability to modulate proliferation, survival, migration, metastasis, morphology, cytoskeletal organization and intracellular signal transduction in mammalian cells. Such cells are preferably cancer cells and/or lymphocytes. In a preferred embodiment, the method involves screening for a bioactive agent capable of binding to MINK3 protein using assays provided herein. In another preferred embodiment, the method involves screening for a bioactive agent capable of modulating MINK3 binding using assays provided herein. In another preferred embodiment, the method involves screening for a bioactive agent capable of modulating MINK3 activity using assays provided herein.

In a preferred embodiment the methods comprise combining a MINK3 protein, a candidate bioactive agent and a cell or a population of cells and determining the effect on the cell in the presence and absence of candidate agent.

In a preferred embodiment, the methods comprise introducing a recombinant MINK3 nucleic acid into a host cell capable of expressing the nucleic acid, contacting the cell with a candidate bioactive agent, and determining the effect on the cell in the presence and absence of candidate bioactive agent. In another preferred embodiment, a library of candidate bioactive agents is added to a plurality of cells comprising a recombinant nucleic acid encoding a MINK3 protein.

A MINK3 protein used in screening methods provided herein may be recombinant, isolated or cell-free as in a cell lysate.

Preferred candidate bioactive agents for use in screening methods provided herein include small molecule chemical compounds, peptides, cyclic peptides, nucleic acids, antibodies, antisense nucleic acids, RNAi, and ribozymes.

In another aspect, the invention provides compositions and methods for diagnostic and prognostic determination of disorders involving MINK3 dysfunction and/or dysregulation. Without being bound by theory, such disorders involve the dysregulation of MINK3 gene expression, aberrant MINK3 gene structure and/or modification, the dysregulation and/or dysfunction of MINK3 protein, and aberrant MINK3 protein structure and/or modification.

Further provided herein are compositions and methods for prophylaxis and therapeutic treatment of disorders related to and/or involving MINK3 dysfunction or dysregulation. In a preferred embodiment, such disorders include cancer, e.g., melanoma, breast, ovarian, lung, gastrointestinal and colon, prostate, and leukemia and lymphomas, e.g., multiple myeloma. In addition, such compositions are useful for treating noncancerous disease states caused by pathologically proliferating cells such as thyroid hyperplasia (Grave's disease), psoriasis, benign prostatic hypertrophy, neurofibromas, atherosclerosis, restenosis, and other vasoproliferative disease. In a preferred embodiment, such disorders involve dysfunction or dysregulation of leukocyte function, preferably lymphocyte function.

In one aspect, the present invention provides isolated polypeptides which specifically bind to a MINK3 protein as described herein. In a preferred embodiment, the isolated peptide is an anti-MINK3 antibody. In a further preferred embodiment, the isolated peptide is an anti-MINK3 monoclonal antibody. In a preferred embodiment, the anti-MINK3 antibody will reduce or eliminate the biological function of MINK3 protein.

In a preferred embodiment, the present invention provides MINK3 proteins and nucleic acids, as well as agents that bind to them and/or modulate their activity, including and preferably small molecule chemical compositions as discussed herein, which are useful in the treatment of acute and chronic inflammatory diseases and autoimmune diseases, as well as in the treatment of a host receiving a transplant, as well as diseases characterized by immunodeficiency.

The dysregulation of mechanisms of programmed cell death can lead to cancer, particularly in lymphocytes (Chao et al., Ann. Rev. Immunol. 16:395-419, 1998). For example, overexpression of Bcl-2, which is involved in normal cell survival through the inhibition of apoptosis, is thought to be responsible for the survival of excessive numbers of lymphocytes in a form of lymphoma.

Without being bound by theory, the present invention provides MINK3 proteins and nucleic acids, as well as agents that bind to them and/or modulate their activity, including and preferably small molecule chemical compositions as discussed herein, which are useful in the modulation of T cell and B cell survival and apoptosis.

Other aspects of the invention will become apparent to the skilled artisan by the following description of the invention.

BRIEF DESCRIPTION OF THE DRAWINGS

FIG. 1 shows the nucleic acid sequence and amino acid sequence of MINK3a, MINK3b, and MINK3c. SEQ ID NOs:2 and 1 depict the nucleic acid and amino acid sequences of MINK3a, respectively. SEQ ID NOs:4 and 3 depict the nucleic acid and amino acid sequences of MINK3b, respectively. SEQ ID NOs:6 and 5 depict the nucleic acid and amino acid sequences of MINK3c, respectively.

MINK3 antisense nucleic acid is herein equivalently referred to as antisense MINK3 nucleic acid, antisense MINK nucleic acid, MINK antisense, MINK antisense nucleic acid, and grammatical equivalents thereof.

Figure 2:
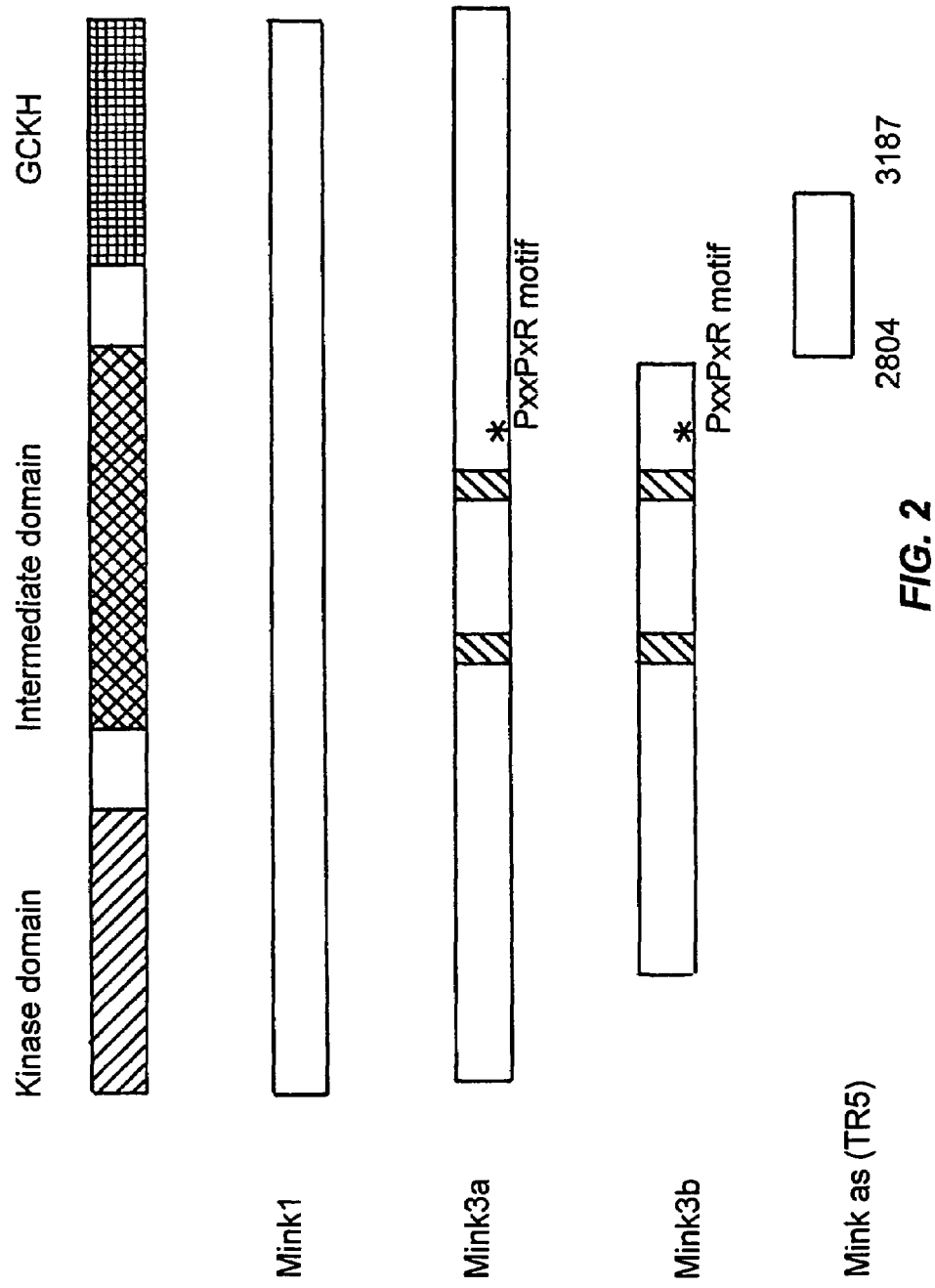
FIG. 2 schematically describes the structure of MINK1 and MINK3 isoforms a and b. The kinase domain, intermediate region, and GCK (GCKH) domain are identified, as is the PxxPxR motif which interacts with the SH3 domain of Nck. The relative position of a MINK3 antisense nucleic acid ("MINK3 as (TR5)") is also shown. It is recognized that the MINK3 antisense nucleic acid described is directed to MINK1 as well. It is also recognized that MINK3b and MINK3c have a frameshift relative to MINK3a; consequently MINK3b and MINK3c proteins comprising MINK3b and MINK3c amino acid sequence are kinase dead MINK3 proteins.
Figure 3:
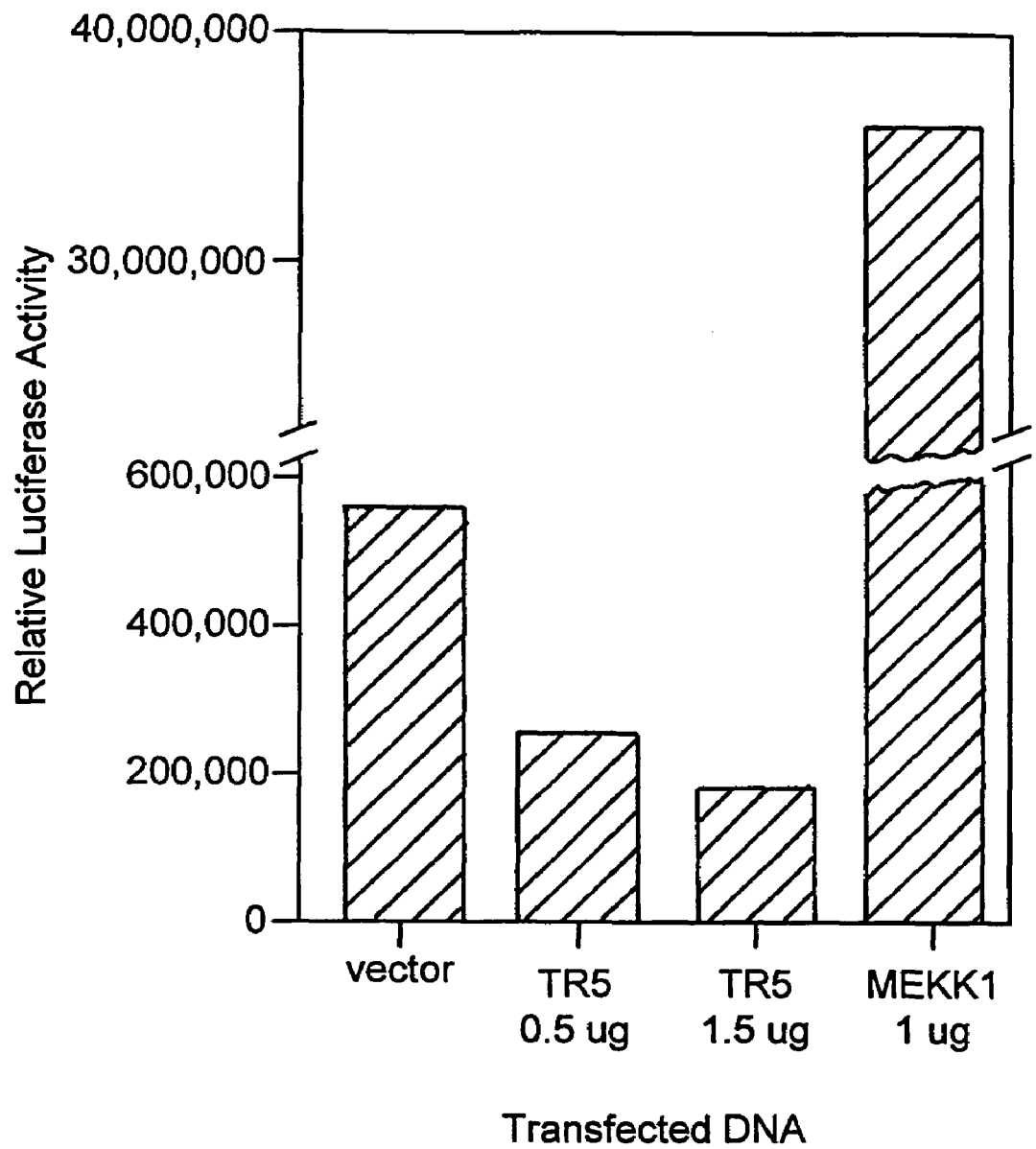

FIG. 3 graphically depicts the effects of MINK3a antisense nucleic acid on AP-1 modulated transcriptional activity in 293 cells. MEKK1 means MEK kinase-1.

Figure 4:
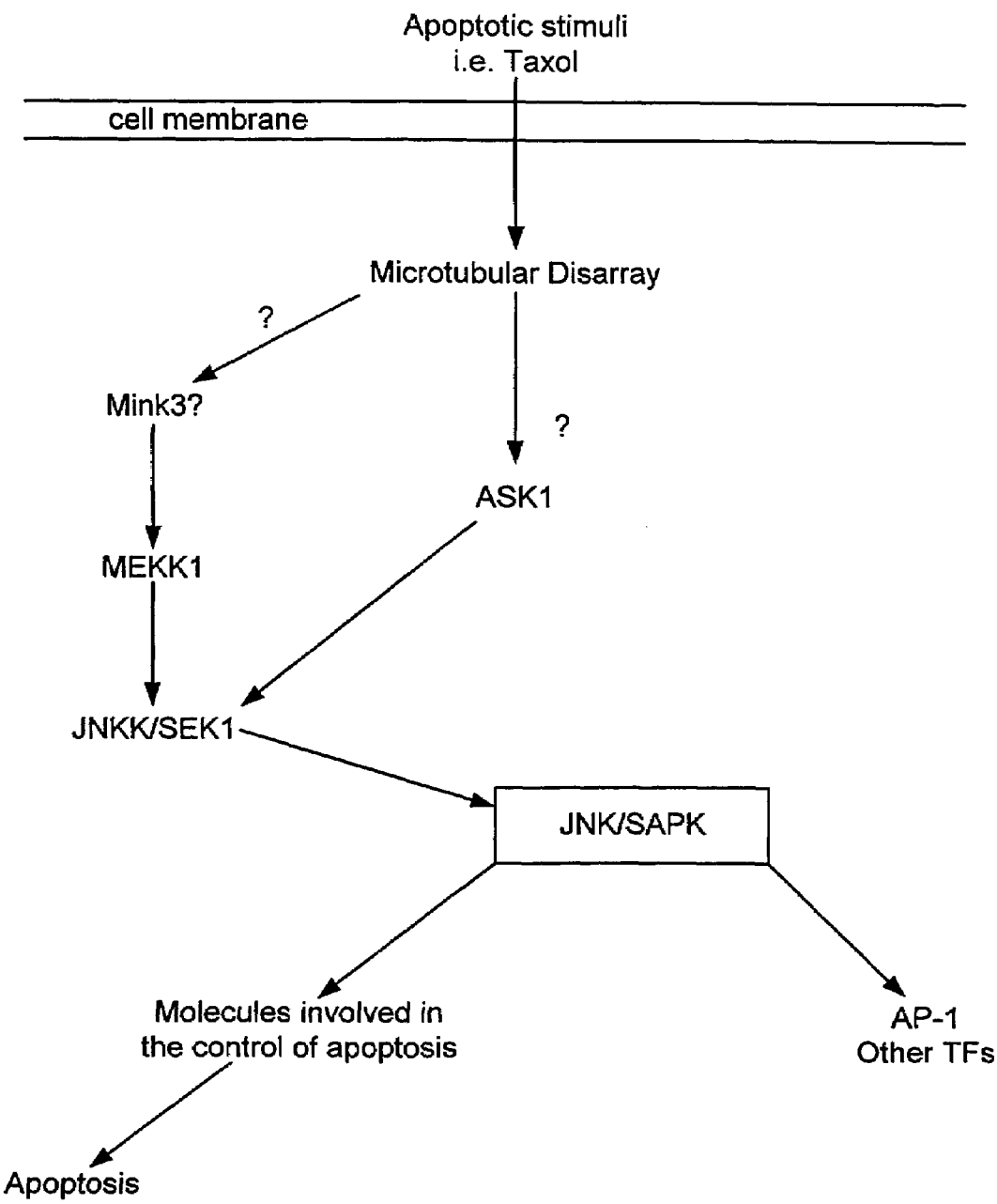

FIG. 4 schematically describes signal transduction pathways mediating the response of mammalian cells to taxol.

Figure 5:
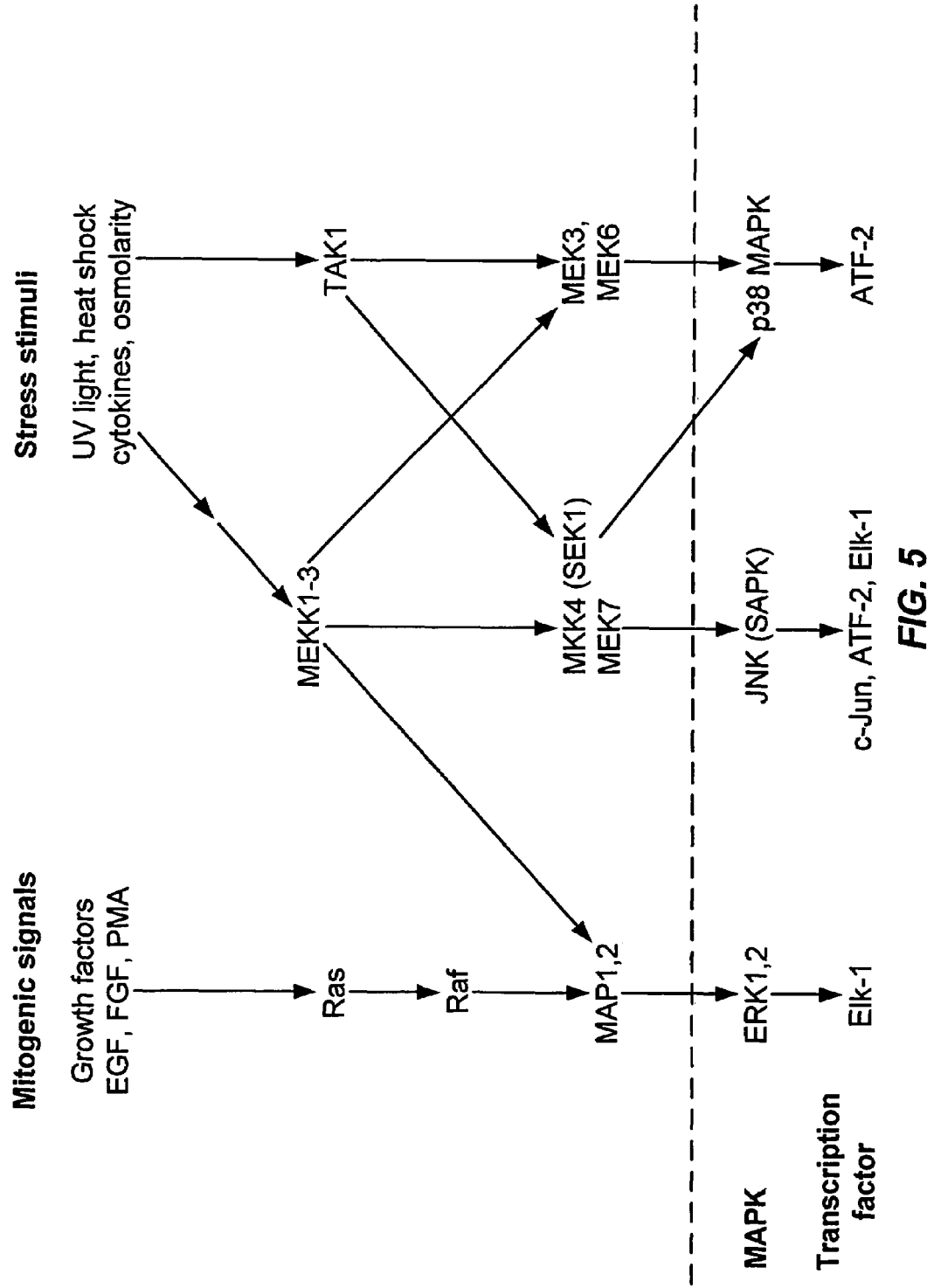
Figure 6:
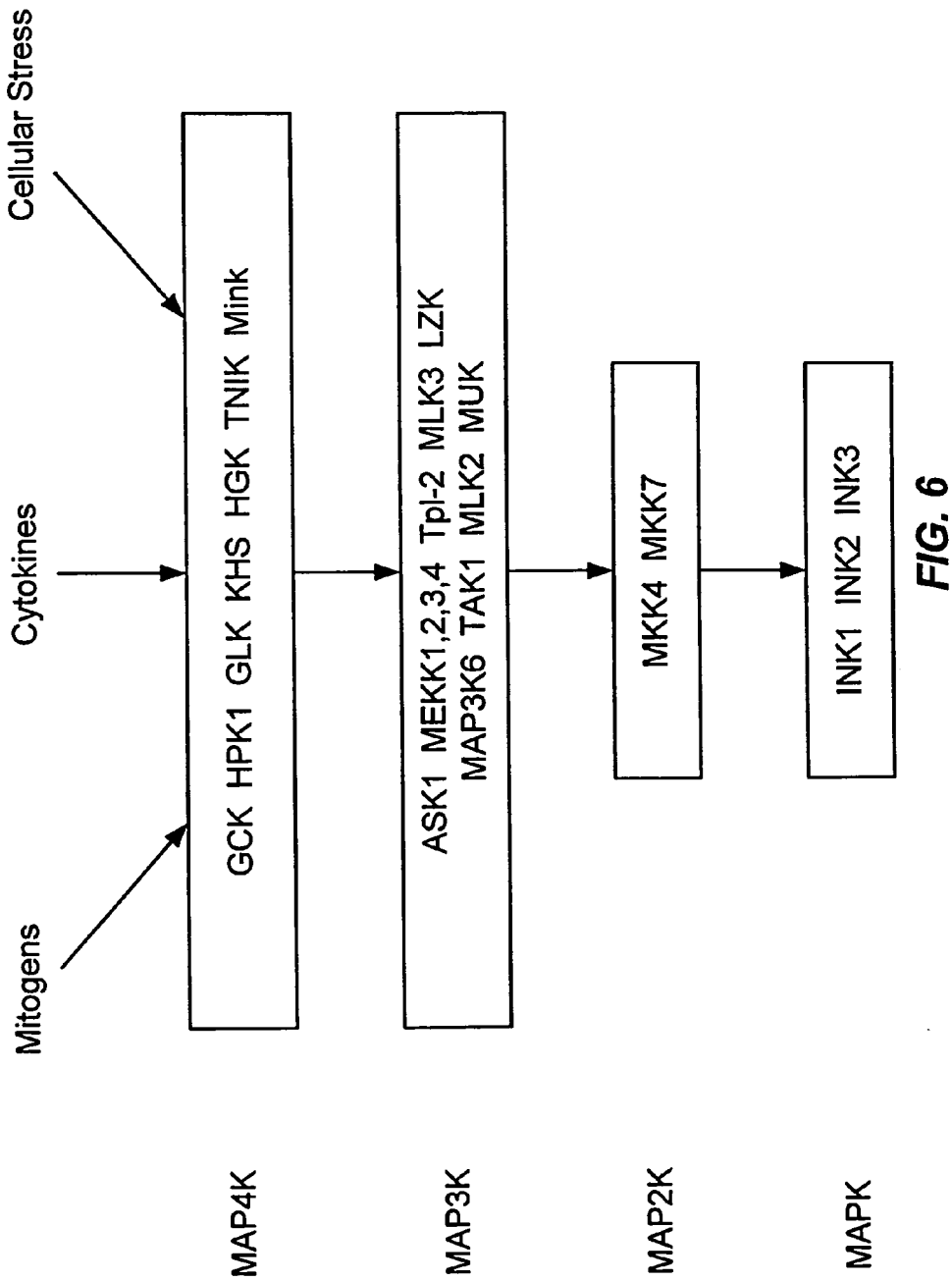

FIGS. 5 and 6 schematically describes the signal transduction pathways that propagate signals initiated by cytokines, mutagens, and cellular stress.

Figure 7:
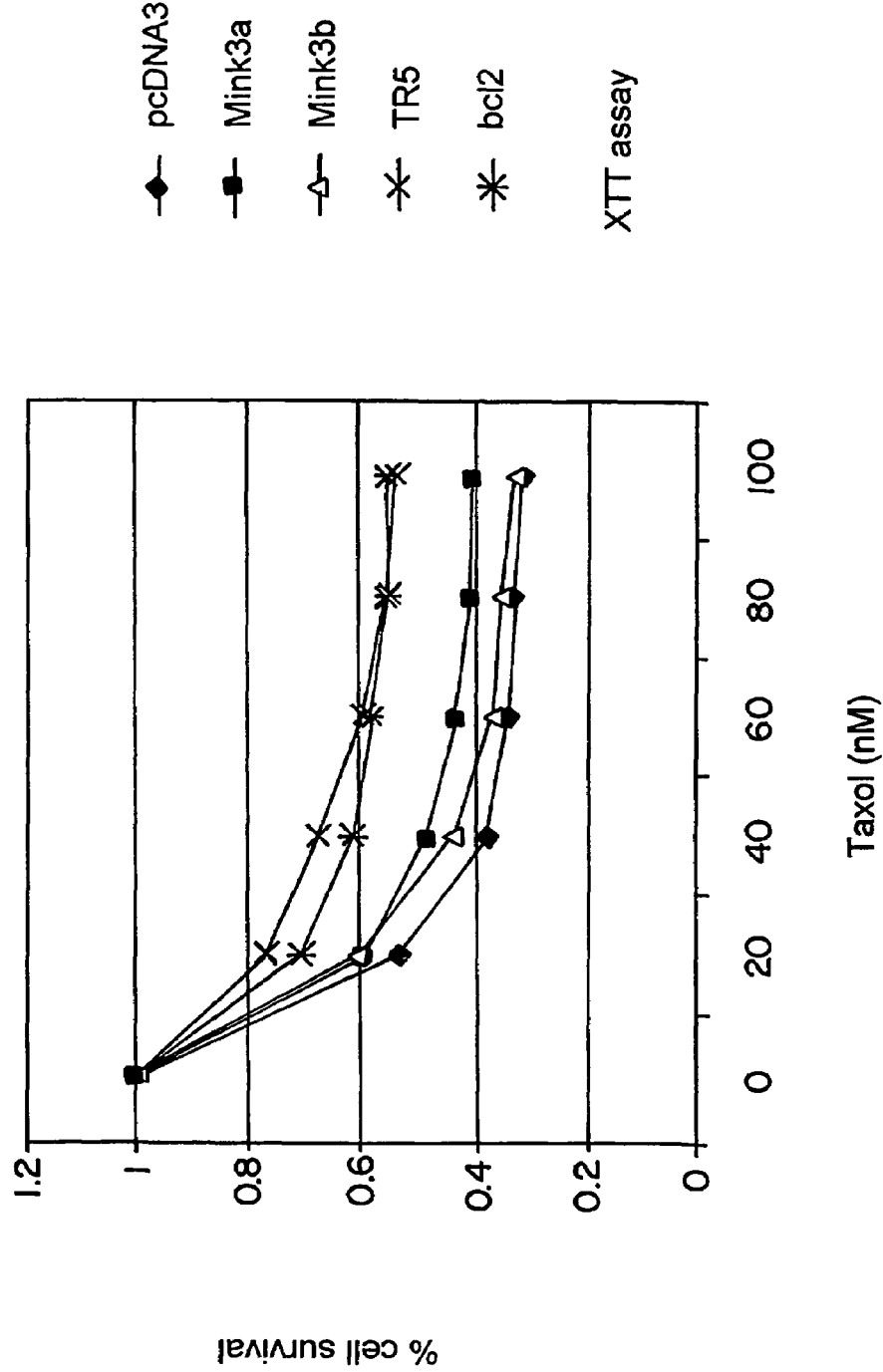

FIG. 7 graphically demonstrates the ability of MINK3 antisense nucleic acid to inhibit taxol-induced cell death in Hela cells.

Figure 8:
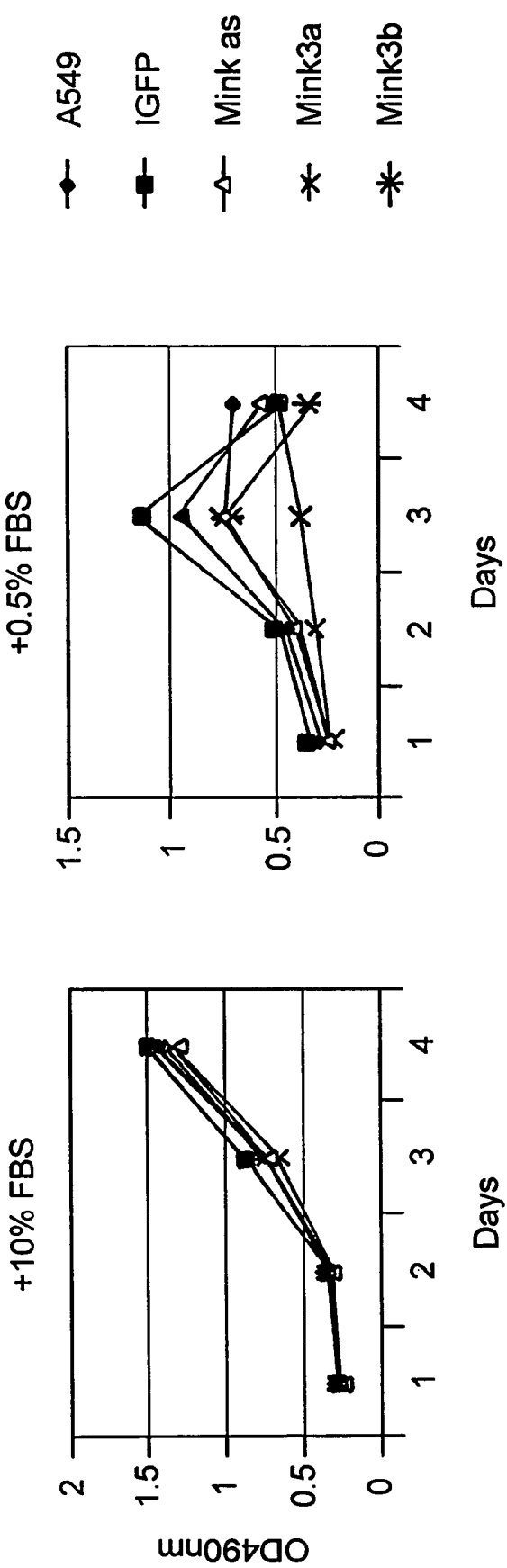

FIG. 8 graphically demonstrates the ability of MINK3a to inhibit proliferation of the human tumor cell line A549 in low serum.

Figure 9:
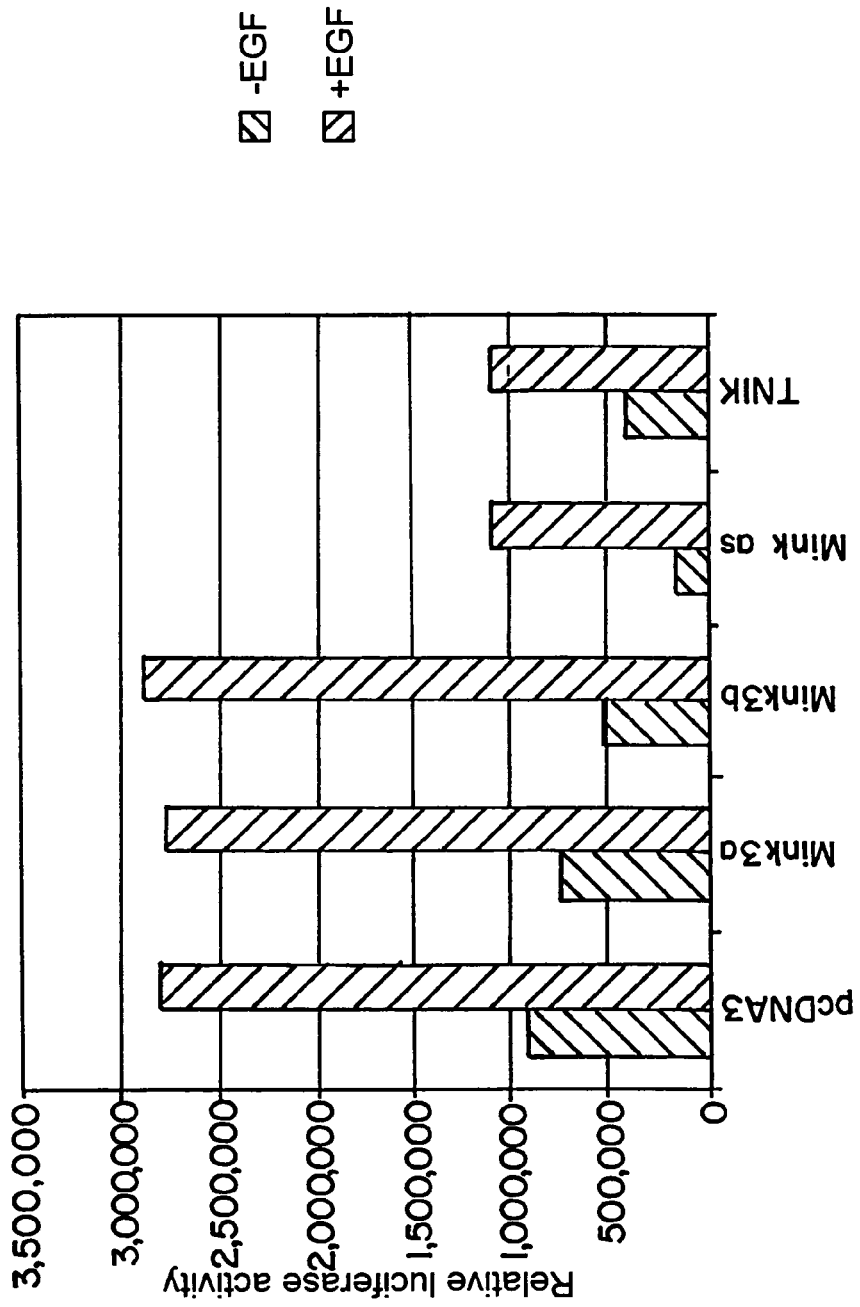

FIG. 9 graphically demonstrates the ability of MINK3 antisense nucleic acid to inhibit EGF-induced ERK-mediated transcriptional activation.

Figure 10:
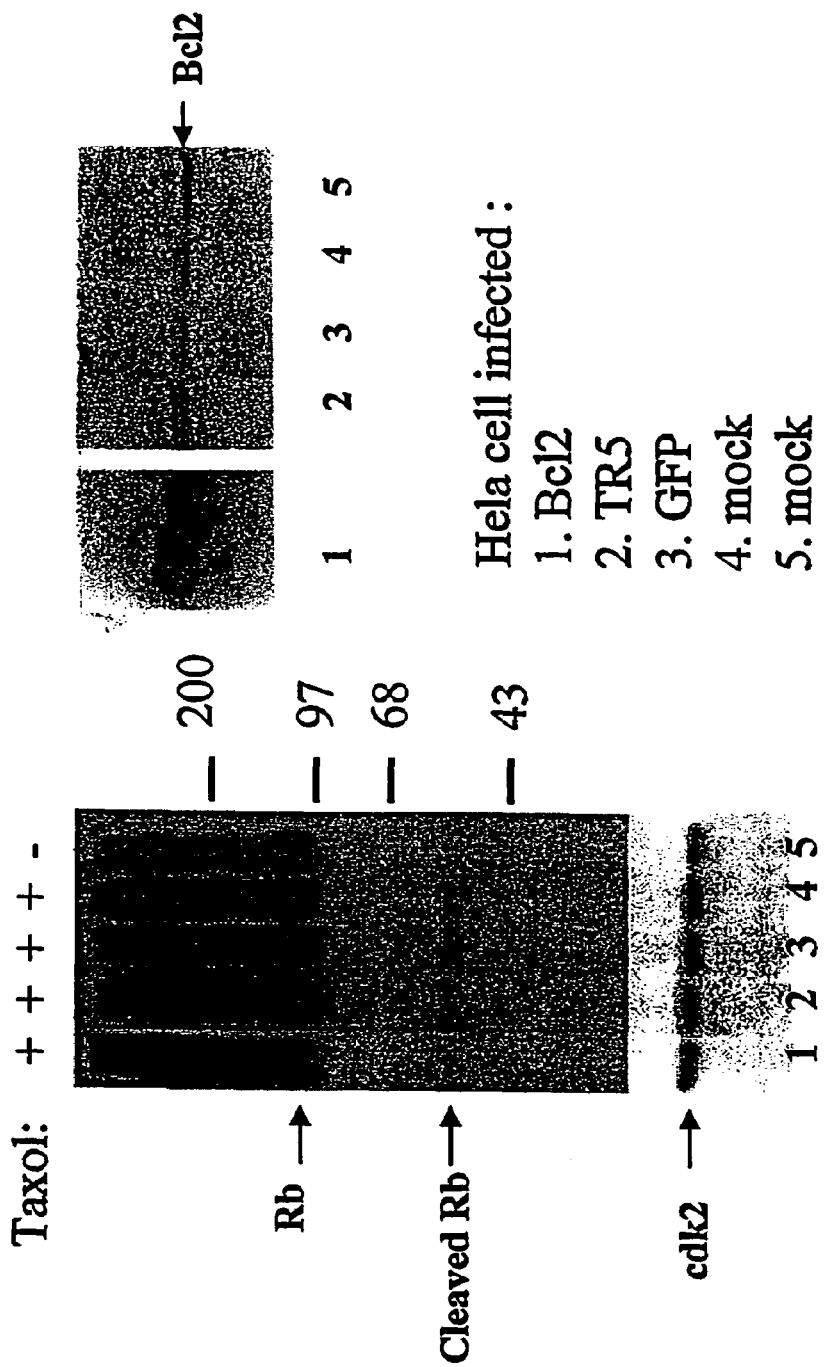

FIG. 10 shows Western blots for retinoblastoma "Rb" and cleaved Rb and Bcl-2 protein from cells expressing (1) Bcl2; (2) MINK3 antisense nucleic acid "TR5"; (3) GFP; and (4), (5) cells transfected with empty vector; in the presence and absence of taxol.

Figure 11:
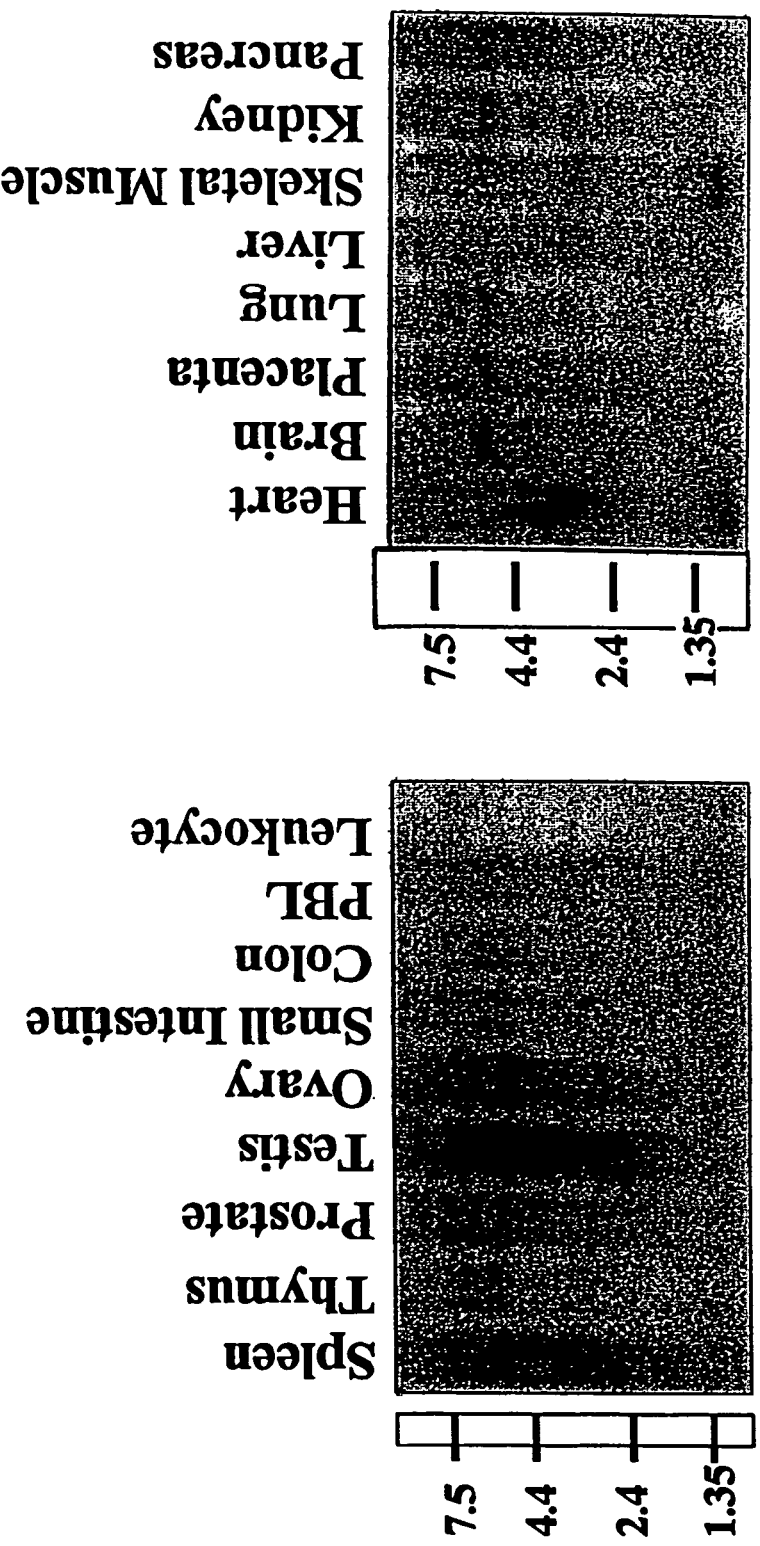

FIG. 11 shows Northern blot of MINK3 mRNA in human tissue samples.

Figure 12:
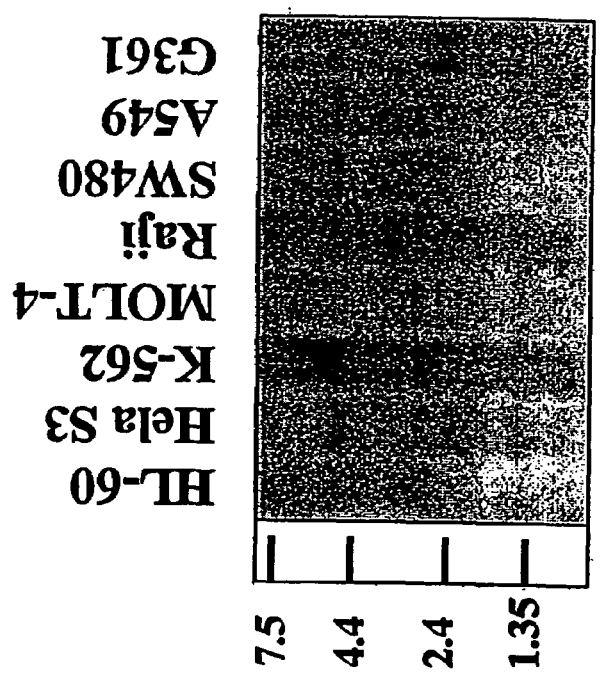

FIG. 12 shows Northern blot of MINK3 mRNA in tumor cell lines.

Figure 13:
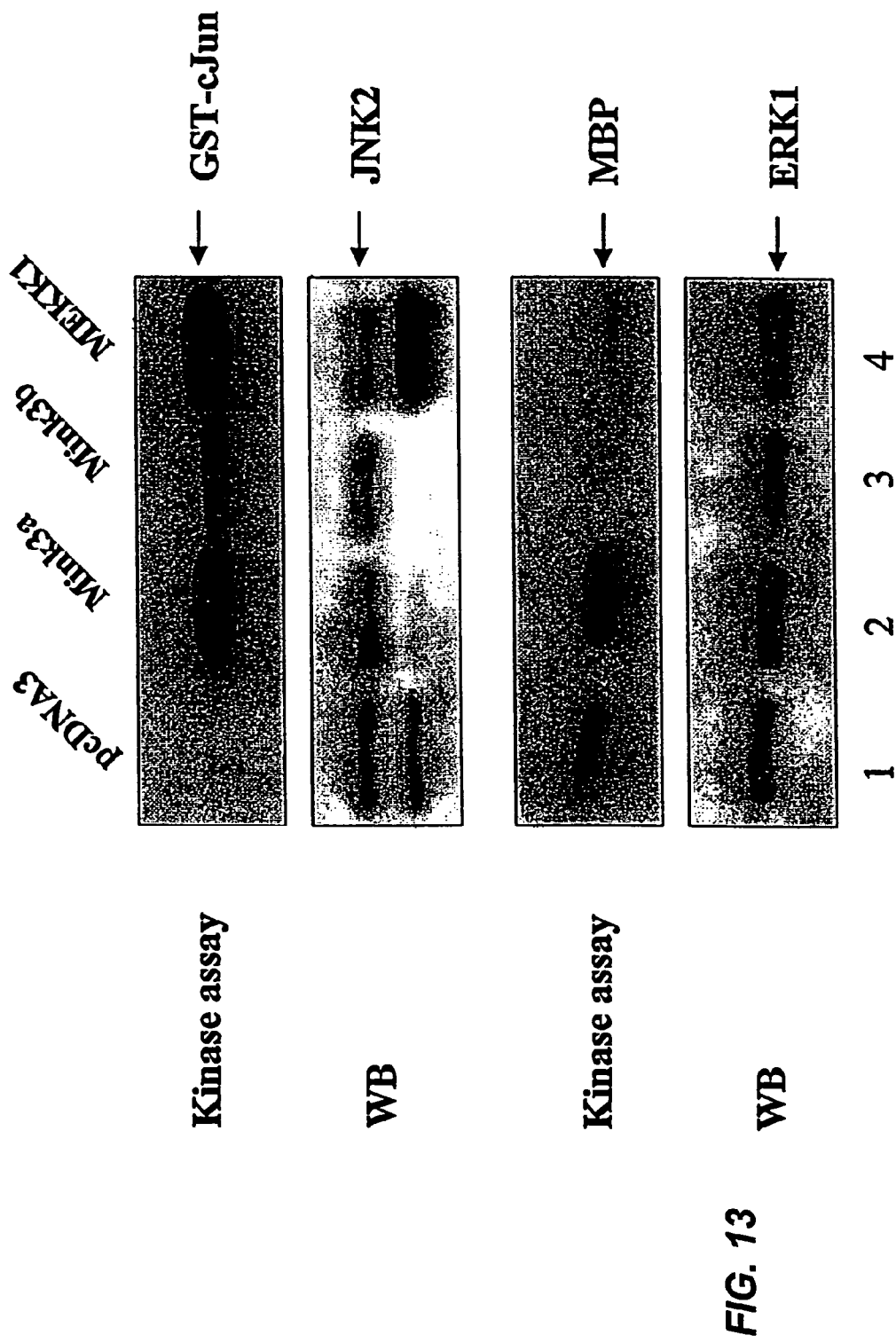

FIG. 13 shows JNK kinase assay using GST-cJUN as substrate, and ERK kinase assay using MBP as substrate, done on extracts from cells transfected with empty vector "pCDNA"; MINK3a, MINK3b or MEKK1. Western blots "WB" are also done for JNK and ERK proteins.

Figure 14:
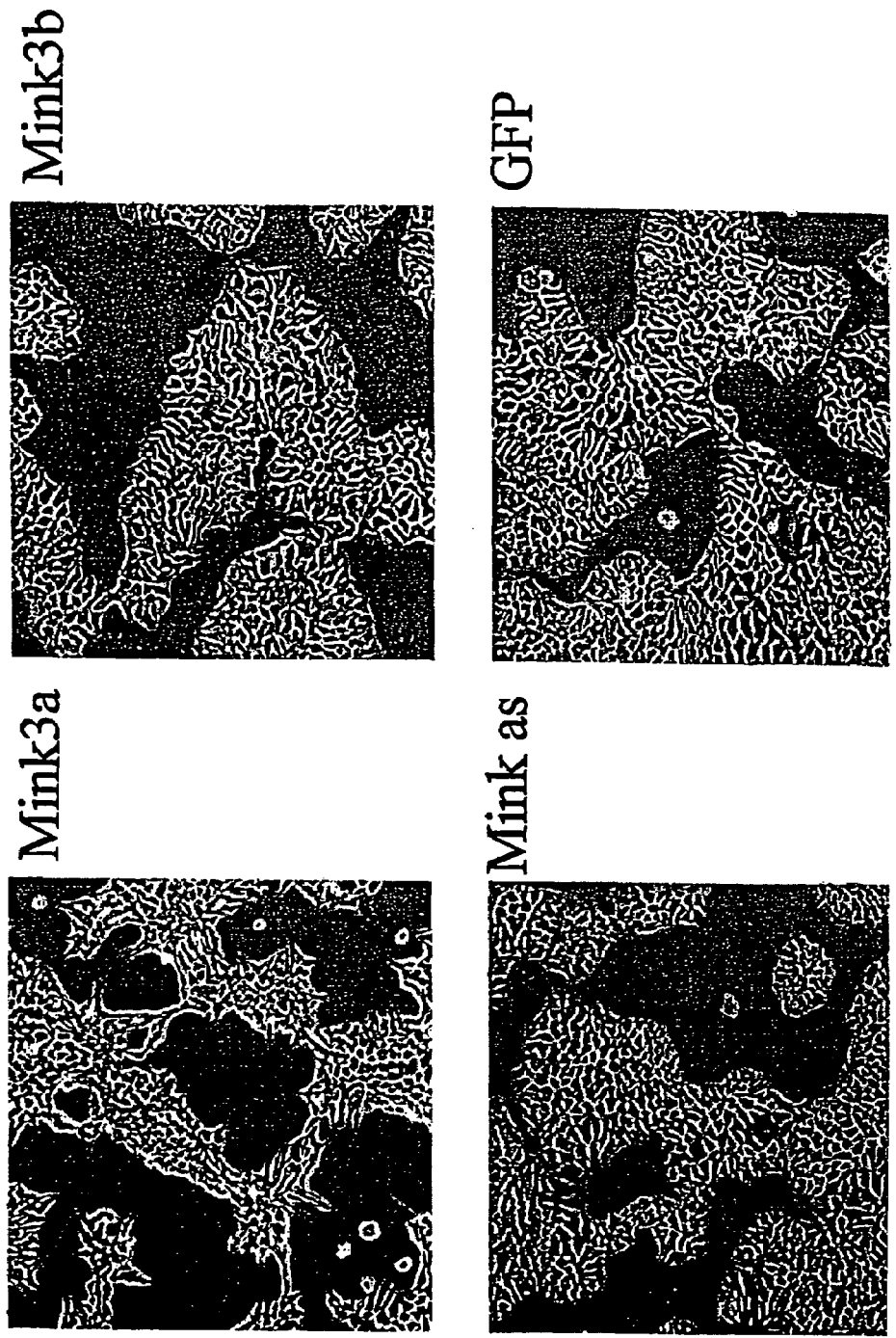

FIG. 14 shows MDA-MB-231 human tumor cells expressing recombinant MINK3a, MINK3b, antisense MINK nucleic acid, or GFP.

FIG. 15 shows stably transfected MDA-MB-231 cells expressing recombinant MINK3a "MINK3a", and MDA-MB-231 cells alone "MDA-MB-231", and stably transfected MDA-MB-231 cells expressing recombinant MINK3a treated with the MEK inhibitor PD98059.

Figure 16:
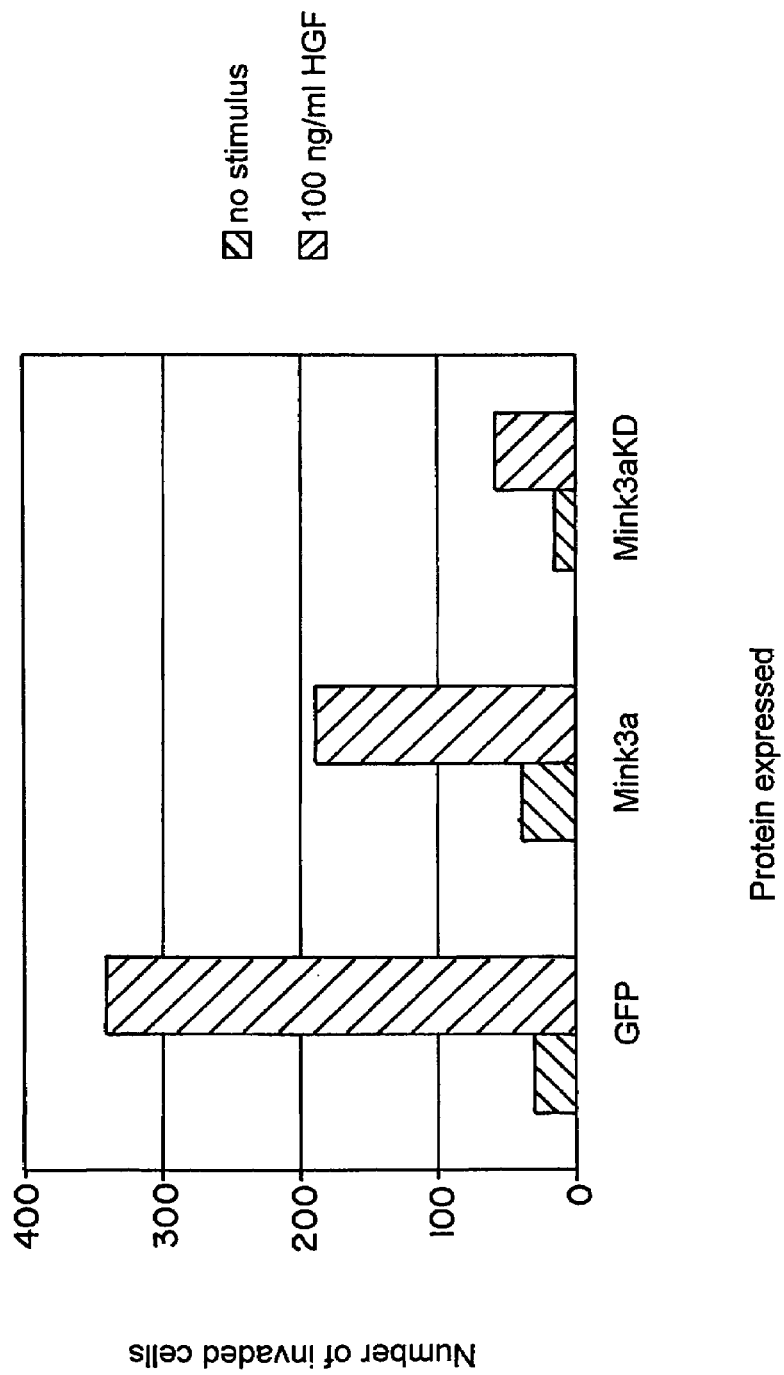

FIG. 16 shows that expression of kinase dead mutant of Mink3a in HT1080 cell (human fibrosarcoma cell line)

greatly reduced its invasion potential comparing with GFP control and wild-type Mink3.

DETAILED DESCRIPTION OF THE INVENTION

The present invention provides compositions and methods for modulating proliferation, survival, migration, morphology, metastasis, cytoskeletal organization and intracellular signal transduction in mammalian cells. Nucleic acids encoding proteins and proteins so encoded which are capable of modulating proliferation, survival, migration, morphology, cytoskeletal organization and intracellular signal transduction in mammalian cells are provided. Compositions and methods for the treatment of disorders related to cell proliferation, survival, morphology and migration are also provided. Prophylactics and methods for the prevention of such disorders are also provided. Also provided are compositions and methods for diagnostic and prognostic determination of such disorders. Further provided are assays for the identification of bioactive agents capable of modulating signal transduction, proliferation, survival, morphology and migration in mammalian cells.

The present invention provides MINK3 nucleic acids, including nucleic acids encoding MINK3 protein, which are capable of modulating proliferation, survival, migration, metastasis, morphology, cytoskeletal organization and intracellular signal transduction in mammalian cells. Also provided herein are MINK3 antisense nucleic acids which are capable of modulating proliferation, survival, migration, morphology, cytoskeletal organization and intracellular signal transduction in mammalian cells. Also provided herein are MINK3 proteins, including dominant negative MINK3 proteins, which are capable of modulating proliferation, survival, migration, morphology, cytoskeletal organization and intracellular signal transduction in mammalian cells.

MINK3 proteins of the present invention include proteins, polypeptides, and peptides. Among the MINK3 proteins included herein are dominant negative isoforms of MINK3 proteins which will inhibit the activity of non-mutant MINK3 proteins in the presence thereof.

In one embodiment, a MINK3 protein has one or more of the following characteristics (MINK3 bioactivities): binding to Nck (for example, an Nck protein comprising the amino acid sequence set forth at Genbank accession no. AAD13752); kinase activity directed at JNK, preferably JNK2; kinase activity directed at ERK, preferably ERK1; an ability to activate JNK and/or ERK, preferably JNK2 and ERK1; an ability to activate JNK and/or ERK signal transduction pathways in mammalian cells; an ability to effect a change in cell morphology in mammalian cells, preferably cancer cells; an ability to disrupt F-actin in mammalian cells, preferably cancer cells.

In a preferred embodiment, MINK3 protein binds to Nck protein via the PxxPxR amino acid motif in MINK3 protein. In a preferred embodiment, MINK3 protein binds to Nck in mammalian cells. IN one embodiment, MINK3 binds to Nck in tumor cells, for example 293 cells.

Also provided herein are MINK3 dominant negative proteins which inhibit at least one MINK3 protein activity. In a preferred embodiment, the MINK3 dominant negative protein has one or more of the following characteristics (MINK3 dominant negative activities): an ability to bind Nck protein; an inability to bind Nck protein; an ability to inhibit growth factor-induced ERK activation, preferably EGF-induced ERK activation; an ability to inhibit proliferation in a mammalian cell, preferably a cancer cell; an ability to inhibit growth factor-induced proliferation in a mammalian cell, preferably EGF-induced proliferation; an ability to inhibit growth factor-dependent proliferation in a mammalian cell, preferably EGF-dependent proliferation; an ability to inhibit aberrant cell proliferation, preferably involving aberrant JNK and/or ERK activation, preferably in cancer cells; an ability to inhibit phosphorylation of c-JUN N-terminal kinase (JNK) and/or ERK, preferably JNK2 and/or ERK1; an ability to inhibit activation of JNK and/ir ERK, preferably JNK2 and/or ERK1; an ability to inhibit the JNK signal transduction pathway and/or the ERK signal transduction pathway in a mammalian cell, preferably a cancer cell, preferably a lymphocyte; an ability to inhibit taxol-induced cleavage of Rb and apoptosis in a mammalian cell; an ability to promote survival in a mammalian cell following exposure to taxol; an ability to inhibit the transcription promoting activity of AP-1 in a mammalian cell; an ability to inhibit transcriptional activation by one or more AP-1 response elements.

In a preferred embodiment, the MINK3 protein has one or more of the MINK3 bioactivities described herein. In other embodiments where particular bioactivities are not required, a MINK3 protein does not include all bioactivities described herein for MINK3 proteins.

It has been reported that the adaptor protein Nck links receptor tyrosine kinases with the serine-threonine kinase Pak1. Nck is an adaptor protein composed of a single SH2 domain and three SH3 domains. Upon growth factor stimulation, Nck is recruited to receptor tyrosine kinases via its SH2 domain, probably initiating one or more signaling cascades. Galisteo, et al., *J Biol Chem,* 271(35):20997-1000 (1996). Also see, Chen, et al., *J Biol Chem.,* 273(39): 25171-8 (1998) which reports on Nck family genes, chromosomal localization and expression.

In one embodiment, MINK3 nucleic acids or MINK3 proteins are initially identified by substantial nucleic acid and/or amino acid sequence identity or similarity to sequences provided herein. In a preferred embodiment, MINK3 nucleic acids or MINK3 proteins have sequence identity or similarity to the sequences provided herein as described below and one or more of the MINK3 protein bioactivities (or MINK3 dominant negative activities or MINK3 antisense nucleic acid activities) as described herein. Such sequence identity or similarity can be based upon the overall nucleic acid or amino acid sequence.

In a preferred embodiment, a protein is a "MINK3 protein" as defined herein if it comprises an amino acid sequence having at least about 80%, more preferably at least about 85%, more preferably at least about 90%, more preferably at least about 95%, more preferably at least about 98% identity to an amino acid sequence selected from the group consisting of the amino acid sequences set forth in SEQ ID NOs:1, 3, and 5.

In a preferred embodiment, the MINK3 protein comprises an amino acid sequence selected from the group consisting of the amino acid sequences set forth in SEQ ID NOs:1, 3, and 5.

In another preferred embodiment, a MINK3 protein has an overall sequence similarity to an amino acid sequence selected from the group consisting of the amino acid sequences set forth in SEQ ID NOs:1, 3, and 5 of greater than at least about 80%, more preferably at least about 85%, more preferably at least about 90%, more preferably at least about 95%, more preferably at least about 98%, more preferably 100%.

In another preferred embodiment, a MINK 3 protein provided herein comprises a GCK domain comprising an amino acid sequence having at least about 80%, more preferably at least about 85%, more preferably at least about 90%, more preferably at least about 95%, more preferably at least about 98%, more preferably about 99%, more preferably 100% identity to the amino acid sequence set forth by amino acids 994-1292 or 994-1290 in SEQ ID NO:1.

In another preferred embodiment, a MINK 3 protein provided herein comprises a catalytic serine/threonine kinase domain comprising an amino acid sequence having at least about 80%, more preferably at least about 85%, more preferably at least about 90%, more preferably at least about 95%, more preferably at least about 98%, more preferably about 99%, more preferably 100% identity to the amino acid sequence set forth by amino acids 25-289 in SEQ ID NO:1.

In another preferred embodiment, a MINK 3 protein provided herein comprises a catalytic tyrosine kinase domain comprising an amino acid sequence having at least about 80%, more preferably at least about 85%, more preferably at least about 90%, more preferably at least about 95%, more preferably at least about 98%, more preferably about 99%, more preferably 100% identity to the amino acid sequence set forth by amino acids 26-286 in SEQ ID NO:1.

In another preferred embodiment, a MINK 3 protein provided herein comprises an ATP binding domain comprising an amino acid sequence having at least about 80%, more preferably at least about 85%, more preferably at least about 90%, more preferably at least about 95%, more preferably at least about 98%, more preferably about 99%, more preferably 100% identity to the amino acid sequence set forth by amino acids 32-54 in SEQ ID NO:1.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith, et al., Adv. Appl. Math. 2:482 (1981), by the sequence identity alignment algorithm of Needleman, et al., J. Mol. Biol., 48:443 (1970), by the search for similarity method of Pearson, et al., PNAS USA, 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng, et al., J. Mol. Evol., 35:351-360 (1987); the method is similar to that described by Higgins, et al., CABIOS, 5:151-153 (1989). Useful PILEUP parameters including a default gap weight of 3.00, a default gap length weight of 0.10, and weighted end gaps.

Another example of a useful algorithm is the BLAST algorithm, described in Altschul, et al., J. Mol. Biol. 215: 403-410, (1990) and Karlin, et al., PNAS USA, 90:5873-5787 (1993). A particularly useful BLAST program is the WU-BLAST-2 program which was obtained from Altschul, et al., Methods in Enzymology, 266:460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul, et al., Nucleic Acids Res., 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the MINK3 protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than a protein comprising an amino acid sequence selected from the group consisting of the amino acid sequences set forth in SEQ ID NOs:1, 3, and 5, it is understood that in one embodiment, the percentage of sequence identity will be determined based on the number of identical amino acids in relation to the total number of amino acids. Thus, for example, sequence identity of sequences shorter than that shown in SEQ ID NO:1, 3, and 5, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

MINK3 proteins of the present invention may be shorter or longer than the amino acid sequences encoded by the nucleic acid sequences set forth in SEQ ID NOs:2, 4, and 6. Thus, in a preferred embodiment, included within the definition of MINK3 proteins are portions or fragments of the amino acid sequences encoded by the nucleic acid sequences provided herein. In one embodiment herein, fragments of MINK3 proteins are considered MINK3 proteins if a) they share at least one antigenic epitope; b) have at least the indicated sequence identity; c) and preferably have MINK3 biological activity as further defined herein. In some cases, where the sequence is used diagnostically, that is, when the presence or absence of MINK3 nucleic acid is determined, only the indicated sequence identity is required. The nucleic acids of the present invention may also be shorter or longer than the sequences set forth in SEQ ID NOs:2, 4, and 6. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, MINK3 proteins can be made that are longer than those consisting essentially of an amino acid sequence selected from the group consisting of the amino acid sequences set forth in SEQ ID NOs:1, 3, and 5; for example, by the addition of epitope or purification tags, the addition of other fusion sequences, or the elucidation of additional coding and non-coding sequences. As described below, the fusion of a MINK3 peptide to a fluorescent peptide, such as Green Fluorescent Peptide (GFP), is particularly preferred.

MINK3 proteins may also be identified as encoded by MINK3 nucleic acids which hybridize to a nucleic acid comprising a nucleic acid sequence selected from the group consisting of the nucleic acid sequences set forth in SEQ ID NOs:2, 4, and 6. Hybridization conditions are further described below.

In a preferred embodiment, when a MINK3 protein is to be used to generate antibodies, a MINK3 protein must share at least one epitope or determinant with the full length protein. By "epitope" or "determinant" herein is meant a portion of a protein which will generate and/or bind an antibody. Thus, in most instances, antibodies made to a smaller MINK3 protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibodies to a MINK3 protein are capable of reducing or eliminating the biological function of the MINK3 proteins described herein, as is described below. That is, the addition of anti-MINK3 protein antibodies (either polyclonal or preferably monoclonal) to MINK3 proteins (or cells containing MINK3 proteins) may reduce or eliminate one or more MINK3 bioactivities as described herein. Generally, at least a 25% decrease in activity is preferred, with at least about 50% being particularly preferred and about a 95-100% decrease being especially preferred.

The MINK3 antibodies of the invention specifically bind to MINK3 proteins. By "specifically bind" herein is meant that the antibodies bind to the protein with a binding constant in the range of at least $10^{-4}$-$10^{-6}$ M$^{-1}$, with a preferred range being $10^{-7}$-$10^{-9}$ M$^{-1}$. Antibodies are further described below.

In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. Thus the sequence identity of the nucleic acid sequence as compared to a nucleic acid sequence selected from the group of nucleic acid sequences set forth in SEQ ID NOs:2, 4, and 6 is preferably greater than about 80%, more preferably greater than about 85%, more preferably greater than about 90%, more preferably greater than about 95%, more preferably greater than about 98%, more preferably about 99%, more preferably 100%.

In a preferred embodiment, a MINK3 nucleic acid encodes a MINK3 protein. As will be appreciated by those in the art, due to the degeneracy of the genetic code, an extremely large number of nucleic acids may be made, all of which encode the MINK3 proteins of the present invention. Thus, having identified a particular amino acid sequence, those skilled in the art could make any number of different nucleic acids, by simply modifying the sequence of one or more codons in a way which does not change the amino acid sequence of the MINK3 protein.

In one embodiment, the nucleic acid is determined through hybridization studies. Thus, for example, nucleic acids which hybridize under high stringency conditions to a nucleic acid comprising a nucleic acid sequence selected from the group consisting of the nucleic acid sequences set forth in SEQ ID NOs:2, 4, and 6, or complements thereof, are considered MINK3 nucleic acids. High stringency conditions, including washing conditions, are known in the art; see for example Maniatis, et al., *Molecular Cloning: A Laboratory Manual*, 2d Edition, 1989, and *Current Protocols in Molecular Biology*, eds. F. Ausubel et al., New York, Greene Pub. Associates & Wiley Interscience, 1988; both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Wash conditions for stringent hybridization typically involve a lower sodium (or other salt) concentration, and a lower temperature, than that used in the hybridization step, as discussed in Maniatis (supra), Ausubel (supra) and Tijssen (supra).

Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Those of ordinary skill will readily recognize that alternative hybridization and wash conditions can be utilized to provide conditions of similar stringency.

In another embodiment, less stringent hybridization conditions are used; for example, moderate or low stringency conditions may be used, as are known in the art; see Maniatis and Ausubel, (supra), and Tijssen (supra).

Exemplary moderately stringent hybridization conditions include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65 □C, depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

By "disorder associated with cellular proliferation" or "disease associated with cellular proliferation" herein is meant a disease state which is marked by either an excess or a deficit of cellular proliferation or apoptosis. Such disorders associated with increased cellular proliferation include, but are not limited to, cancer and non-cancerous pathological proliferation.

The MINK3 proteins and nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in SEQ ID NOs:2, 4, and 6 also include complements thereof. By the term "recombinant nucleic acid" herein is meant nucleic acid, originally formed in vitro, in general, by the manipulation of nucleic acid by endonucleases, in a form not normally found in nature. Thus an isolated MINK3 nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a MINK3 protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides MINK3 protein variants. These variants fall into one or more of three classes: substitutional, insertional or deletional variants. These variants ordinarily are prepared by site specific mutagenesis of nucleotides in the DNA encoding a MINK3 protein, using cassette or PCR mutagenesis or other techniques well known in the art, to produce DNA encoding the variant, and thereafter expressing the DNA in recombinant cell culture as outlined above. However, variant MINK3 protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the MINK3 protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed MINK3 variants screened for the optimal combination of desired activity. Techniques for making substitution mutations at predetermined sites in DNA having a known sequence are well known, for example, M13 primer mutagenesis and PCR mutagenesis. Screening of the mutants is done using assays of MINK3 protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the MINK3 protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the MINK3 proteins as needed. Alternatively, the variant may be designed such that the biological activity of the MINK3 protein is altered. For example, glycosylation sites may be altered or removed.

In one aspect the invention provides dominant negative MINK3 proteins which inhibit at least one MINK3 protein activity, as described herein. In a preferred embodiment, the dominant negative MINK3 protein is a kinase dead MINK3 protein. In a preferred embodiment, the dominant negative kinase dead MINK3 protein variant has a mutation in an ATP-binding domain. Preferably the non-mutant ATP-binding domain of the non-variant MINK3 protein (non-variant with respect to ATP-binding domain) comprises the amino acid sequence set forth by amino acids 32-54 in SEQ ID NO:1. In a preferred embodiment, the dominant negative kinase dead MINK3 protein variant has a substitution mutation in the ATP binding domain at a position corresponding to K54 in SEQ ID NO:1.

In a preferred embodiment, the dominant negative MINK3 protein has MINK3 antisense nucleic acid activity.

Covalent modifications of MINK3 polypeptides are included within the scope of this invention. One type of covalent modification includes reacting targeted amino acid residues of a MINK3 polypeptide with an organic derivatizing agent that is capable of reacting with selected side chains or the N- or C-terminal residues of a MINK3 polypeptide. Derivatization with bifunctional agents is useful, for instance, for crosslinking MINK3 to a water-insoluble support matrix or surface for use in the method for purifying anti-MINK3 antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithio-bis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification of the MINK3 polypeptide included within the scope of this invention comprises altering the native glycosylation pattern of the polypeptide. "Altering the native glycosylation pattern" is intended for purposes herein to mean deleting one or more carbohydrate moieties found in native sequence MINK3 polypeptide, and/or adding one or more glycosylation sites that are not present in the native sequence MINK3 polypeptide.

Addition of glycosylation sites to MINK3 polypeptides may be accomplished by altering the amino acid sequence thereof. The alteration may be made, for example, by the addition of, or substitution by, one or more serine or threonine residues to the native sequence MINK3 polypeptide (for O-linked glycosylation sites). The MINK3 amino acid sequence may optionally be altered through changes at the DNA level, particularly by mutating the DNA encoding the MINK3 polypeptide at preselected bases such that codons are generated that will translate into the desired amino acids.

Another means of increasing the number of carbohydrate moieties on the MINK3 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the MINK3 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge, et al., *Anal. Biochem.*, 118:131 (1981). Enzymatic cleavage of carbohydrate moieties on polypeptides can be achieved by the use of a variety of endo- and exo-glycosidases as described by Thotakura, et al., *Meth. Enzymol.*, 138:350 (1987).

Another type of covalent modification comprises linking the MINK3 polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791, 192 or 4,179,337.

MINK3 polypeptides of the present invention may also be modified in a way to form chimeric molecules comprising a MINK3 polypeptide fused to another, heterologous polypeptide or amino acid sequence. In one embodiment, such a chimeric molecule comprises a fusion of a MINK3 polypeptide with a tag polypeptide which provides an epitope to which an anti-tag antibody can selectively bind. The epitope tag is generally placed at the amino- or carboxyl-terminus of the MINK3 polypeptide. The presence of such epitope-tagged forms of a MINK3 polypeptide can be detected using an antibody against the tag polypeptide. Also, provision of the epitope tag enables the MINK3 polypeptide to be readily purified by affinity purification using an anti-tag antibody or another type of affinity matrix that binds to the epitope tag. In an alternative embodiment, the chimeric molecule may comprise a fusion of a MINK3 polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field, et al., *Mol. Cell. Biol.*, 8:2159-2165 (1988)); the c-myc tag and the 8F9, 3C7, 6E10, G4, B7 and 9E10 antibodies thereto (Evan, et al., *Molecular and Cellular Biology*, 5:3610-3616 (1985)); and the Herpes Simplex virus glycoprotein D (gD) tag and its antibody (Paborsky, et al., *Protein Engineering*, 3(6):547-553 (1990)). Other tag polypeptides include the Flag-peptide (Hopp, et al., *BioTechnology*, 6:1204-1210 (1988)); the KT3 epitope peptide (Martin, et al., *Science*, 255:192-194 (1992)); tubulin epitope peptide (Skinner, et al., *J. Biol. Chem.*, 266:15163-15166 (1991)); and the T7 gene 10 protein peptide tag (Lutz-Freyermuth, et al., *Proc. Natl. Acad. Sci. USA*, 87:6393-6397 (1990)).

In an embodiment herein, MINK3 genes from other organisms are cloned and expressed as outlined below. Thus, probe or degenerate polymerase chain reaction (PCR) primer sequences may be used to find other related MINK3 proteins from humans or other organisms. As will be appreciated by those in the art, particularly useful probe and/or PCR primer sequences include the unique areas of the MINK3 nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant MINK3 nucleic acid can be further-used as a probe to identify and isolate other MINK3 nucleic acids. It can also be used as a "precursor" nucleic acid to make modified or variant MINK3 nucleic acids and proteins.

Using the nucleic acids of the present invention which encode a MINK3 protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the MINK3 protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the MINK3 protein; for example, transcriptional and translational regulatory nucleic acid sequences from *Bacillus* are preferably used to express the MINK3 protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

MINK3 proteins of the present invention are produced by culturing a host cell transformed with an expression vector containing nucleic acid encoding a MINK3 protein, under the appropriate conditions to induce or cause expression of the MINK3 protein. The conditions appropriate for MINK3 protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fingi, and insect and animal cells, including mammalian cells. Of particular interest are *Drosophila melanogaster* cells, *Saccharomyces cerevisiae* and other yeasts, *E. coli*, *Bacillus subtilis*, SF9 cells, C129 cells, 293 cells, *Neurospora*, BHK, CHO, COS, and HeLa cells, fibroblasts, Schwanoma cell lines, immortalized mammalian myeloid and lymphoid cell lines, and human tumor lines, including and preferably MDA-MB-231 cells.

In a preferred embodiment, the MINK3 proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for MINK3 protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenyltion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, MINK3 proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of MINK3 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the MINK3 protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis*, *E. coli*, *Streptococcus cremoris*, and *Streptococcus lividans*, among others.

The bacterial expression vectors are transformed into bacterial host cells using techniques well known in the art, such as calcium chloride treatment, electroporation, and others.

In one embodiment, MINK3 proteins are produced in insect cells. Expression vectors for the transformation of insect cells, and in particular, baculovirus-based expression vectors, are well known in the art.

In a preferred embodiment, MINK3 protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The MINK3 protein may also be made as a fusion protein, using techniques well known in the art. Thus, for example, for the creation of monoclonal antibodies, if the desired epitope is small, the MINK3 protein may be fused to a carrier protein to form an immunogen. Alternatively, the MINK3 protein may be made as a fusion protein to increase expression, or for other reasons. For example, when the MINK3 protein is a MINK3 peptide, the nucleic acid encoding the peptide may be linked to other nucleic acid for expression purposes. Similarly, MINK3 proteins of the invention can be linked to protein labels, such as green fluorescent protein (GFP), red fluorescent protein (RFP), blue fluorescent protein (BFP), yellow fluorescent protein (YFP), etc.

In one embodiment, the MINK3 nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the MINK3 protein is purified or isolated after expression. MINK3 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the MINK3 protein may be purified using a standard anti-MINK3 antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the MINK3 protein. In some instances no purification will be necessary.

Once expressed and purified if necessary, the MINK3 proteins and nucleic acids are useful in a number of applications.

The nucleotide sequences (or their complement) encoding MINK3 proteins have various applications in the art of molecular biology, including uses as hybridization probes, in chromosome and gene mapping and in the generation of anti-sense RNA and DNA. MINK3 nucleic acids are also useful for the preparation of MINK3 proteins by the recombinant techniques described herein.

Full-length native sequence MINK3 genes, or portions thereof, may be used as hybridization probes for a cDNA library to isolate other genes (for instance, those encoding naturally-occurring variants of MINK3 protein or MINK3 protein from other species) which have a desired sequence identity to the MINK3 protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the MINK3 protein gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the MINK3 protein gene of the present invention can be used to screen libraries of human cDNA, genomic DNA or mRNA to determine which members of such libraries the probe hybridizes.

Nucleotide sequences encoding a MINK3 protein can also be used to construct hybridization probes for mapping the gene which encodes that MINK3 protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly (A) tail found on virtually every eukaryotic mRNA molecule at the 3' end thereof. Oligonucleotides composed of only deoxythymidine (oligo(dT)) are linked to cellulose and the oligo(dT)-cellulose packed into small columns. When a preparation of total cellular RNA is passed through such a column, the mRNA molecules bind to the oligo(dT) by the poly (A) tails while the rest of the RNA flows through the column. The bound mRNAs are then eluted from the column and collected.

Nucleic acids which encode MINK3 protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a MINK3 protein can be used to clone genomic DNA encoding a MINK3 protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for the MINK3 protein transgene incorporation with tissue-specific enhancers. Transgenic animals that include a copy of a transgene encoding a MINK3 protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the MINK3 protein can be used to construct a MINK3 protein "knock out" animal which has a defective or altered gene encoding a MINK3 protein as a result of homologous recombination between the endogenous gene encoding a MINK3 protein and altered genomic DNA encoding a MINK3 protein introduced into an embryonic cell of the animal. For example, cDNA encoding a MINK3 protein can be used to clone genomic DNA encoding a MINK3 protein in accordance with established techniques. A portion of the genomic DNA encoding a MINK3 protein can be deleted or replaced with another gene, such as a gene encoding a selectable marker which can be used to monitor integration. Typically, several kilobases of unaltered flanking DNA (both at the 5' and 3' ends) are included in the vector (see e.g., Thomas, et al., *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li, et al., *Cell*, 69:915 (1992)). The selected cells are then injected into a blastocyst of an animal (e.g., a mouse or rat) to form aggregation chimeras (see e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the MINK3 protein.

It is understood that the models described herein can be varied. For example, "knock-in" models can be formed, or the models can be cell-based rather than animal models.

Nucleic acids encoding MINK3 polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik, et al., *Proc. Natl. Acad. Sci. USA*, 83:4143-4146 (1986)). The oligonucleotides can be modified to enhance their uptake, e.g. by substituting their negatively charged phosphodiester groups by uncharged groups.

In one aspect, the present invention provides antisense MINK3 nucleic acids. In a preferred embodiment, the antisense MINK3 nucleic acid comprises a nucleic acid sequence complementary to the nucleic acid sequence set forth by nucleotides 2804-3187 in SEQ ID NO:2. In another preferred embodiment, the present invention provides antisense MINK3 nucleic acids consisting essentially of a nucleic acid sequence complementary to the nucleic acid sequence set forth by nucleotides 2804-3187 in SEQ ID NO:2.

In a preferred embodiment, the MINK3 antisense nucleic acid will hybridize to MINK3 and MINK1 nucleic acids.

In a preferred embodiment, the MINK3 antisense nucleic acid inhibits one or more MINK3 protein activities. In another preferred embodiment, the MINK3 antisense nucleic acid inhibits more than one MINK3 protein activity. In a further preferred embodiment, the MINK3 antisense nucleic acid inhibits all MINK3 protein activities. In a preferred embodiment, the MINK3 antisense nucleic acid has an activity shared by dominant negative MINK3 protein.

In a preferred embodiment, such antisense MINK3 nucleic acids are capable of inhibiting taxol-induced death in mammalian cells. In a preferred embodiment, such antisense MINK3 nucleic acids are capable of inhibiting taxol-induced cleavage of Rb. In a preferred embodiment, such antisense MINK3 nucleic acids are capable of promoting survival in mammalian cells following exposure to taxol.

In a preferred embodiment, such antisense MINK3 nucleic acids are capable of inhibiting the transcription promoting activity of AP-1 in mammalian cells. AP-1 is well known in the art. AP-1 means activation complex-1 and refers to a complex of the known transcription factors c-JUN and c-FOS. In a preferred embodiment, such MINK3 nucleic acids are capable of inhibiting transcriptional induction by an AP-1 response element. AP-1 response elements are well known in the art.

In a preferred embodiment, such antisense MINK3 nucleic acids are capable of inhibiting growth factor-induced ERK activity in mammalian cells, preferably EGF-induced ERK activity, preferably in cancer cells. In a preferred embodiment, such antisense MINK3 nucleic acids are capable of inhibiting growth factor-induced proliferation in mammalian cells, preferably EGF-induced proliferation, preferably in cancer cells. In a preferred embodiment, such antisense MINK3 nucleic acids are capable of inhibiting growth factor-dependent proliferation in mammalian cells, preferably cancer cells.

In a preferred embodiment, such antisense MINK3 nucleic acids are capable of inhibiting aberrant cell proliferation involving aberrant activation of the ERK and/or JNK signal transduction pathways.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau, et al., *Trends in Biotechnology*, 11:205-210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu, et al., *J. Biol. Chem.*, 262:4429-4432 (1987); and Wagner, et al., *Proc. Natl. Acad. Sci. USA*, 87:3410-3414 (1990). For review of gene marking and gene therapy protocols see Anderson, et al., *Science* 256:808-813 (1992).

In a preferred embodiment, the MINK3 proteins, nucleic acids, variants, modified proteins, cells and/or transgenics containing the said nucleic acids or proteins are used in screening assays. Identification of MINK3 proteins provided herein permits the design of drug screening assays for compounds that bind or interfere with the binding to the MINK3 protein and for compounds which modulate MINK3 protein activity.

The assays described herein preferably utilize the human MINK3 protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative MINK3 proteins may be used, including deletion MINK3 proteins as outlined above.

In a preferred embodiment, the methods comprise combining a MINK3 protein and a candidate bioactive agent, and determining the binding of the candidate agent to the MINK3 protein. In other embodiments, further discussed below, binding interference or bioactivity is determined.

The term "candidate bioactive agent" or "exogenous compound" or "test compound" or "drug candidate" or "modulator" or grammatical equivalents as used herein describes any molecule, e.g., protein, small organic molecule (small molecule chemical compound), carbohydrates (including polysaccharides), polynucleotide, lipids, antisense molecules, RNAi, ribozymes, peptides, oligopeptides (e.g., from about 5 to about 25 amino acids in length, preferably from about 10 to 20 or 12 to 18 amino acids in length, preferably 12, 15, or 18 amino acids in length), cyclic peptides, etc. Small molecule chemical or organic compositions are preferred. Generally a plurality of assay mixtures are run in parallel with different agent concentrations to obtain a differential response to the various concentrations. Typically, one of these concentrations serves as a negative control, i.e., at zero concentration or below the level of detection. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

Candidate agents encompass numerous chemical classes, though typically they are organic molecules, preferably small organic compounds having a molecular weight of more than 100 and less than about 2,500 daltons, preferably less than about 2000 daltons, preferably less than about 1800 daltons, preferably less than about 1700 daltons, preferably less than about 1600 daltons, preferably less than about 1500 daltons, preferably less than about 1400 daltons, preferably less than about 1300 daltons, preferably less than about 1200 daltons, preferably less than about 1100 daltons, preferably less than about 1000 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphosphoroamidite linkages (see Eckstein, Oligonucleotides and Analogues: A Practical Approach, Oxford University Press), and peptide nucleic acid backbones and linkages (see Egholm, *J. Am. Chem. Soc.*, 114: 1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, pp. 169-176 (1995)). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In one embodiment, the screening methods described herein make use of portions of MINK3 proteins, or MINK3 protein fragments. In a preferred embodiment, MINK3 protein fragments having at least one MINK3 bioactivity as described herein are used. MINK3 bioactivity includes binding activity to Nck, modulation of phosphorylation of JNK and/or ERK, modulation of JNK and/or ERK phosphorylation, modulation of JNK and/or ERK activation, modulation of JNK and/or ERK signal transduction, inhibition of taxol-induced Rb cleavage and apoptosis, morphological change, modulation of cell proliferation, and disruption of F-actin. In some embodiments, the assays described herein utilize isolated MINK3 proteins. In other embodiments, cells comprising MINK3 proteins are used. In other embodiments, MINK3 proteins that are cell-free but not isolated, as in a cell lysate, are used.

Generally, in a preferred embodiment of the methods herein, for example for binding assays, the MINK3 protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. In some embodiments, Nck protein can be used. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the MINK3 protein is bound to the support, and a candidate bioactive agent is added to the assay. Alternatively, the candidate agent is bound to the support and the MINK3 protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the MINK3 protein may be done in a number of ways. In a preferred embodiment, the candidate bioactive agent is labeled, and binding determined directly. For example, this may be done by attaching all or a portion of the MINK3 protein to a solid support, adding a labeled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. MINK3 protein), such as an antibody, peptide, binding partner, ligand, etc. In a preferred embodiment the competitor is Nck. Under certain circumstances, there may be competitive binding as between the bioactive agent and the binding moiety, with the binding moiety displacing the bioactive agent. This assay can be used to determine candidate agents which interfere with binding between MINK3 proteins and Nck. "Interference of binding" as used herein means that native binding of the MINK3 protein differs in the presence of the candidate agent. The binding can be eliminated or can be with a reduced affinity. Therefore, in one embodiment, interference is caused by, for example, a conformation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the MINK3 protein and thus is capable of binding to, and potentially modulating, the activity of the MINK3 protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the MINK3 protein with a higher affinity. Thus, if the candidate bioactive agent is labeled, the presence of the label on the support, coupled with a lack of competitor binding, may indicate that the candidate agent is capable of binding to the MINK3 protein.

A preferred embodiment utilizes differential screening to identify drug candidates that bind to the native MINK3 protein, but cannot bind to modified MINK3 proteins. The structure of the MINK3 protein may be modeled, and used in rational drug design to synthesize agents that interact with that site. Drug candidates that affect MINK3 bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

The proteins and nucleic acids provided herein can also be used for screening purposes wherein the protein-protein interactions of the MINK3 proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields, et al., *Nature*, 340:245 (1989); Vasavada, et al., *PNAS USA*, 88:10686 (1991); Fearon, et al., *PNAS USA*, 89:7958 (1992); Dang, et al., *Mol. Cell. Biol.*, 11:954 (1991); Chien, et al., *PNAS USA*, 88:9578 (1991); and U.S. Pat. Nos. 5,283,173, 5,667,973, 5,468,614, 5,525,490, and 5,637,463. a preferred system is described in Ser. No. 09/050,863, filed Mar. 30, 1998 and 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding a MINK3 protein or a portion thereof, and the other encodes a test candidate. Only if the two expression products bind to one another will an indicator, such as a fluorescent protein, or a gene product required fro survival or growth, be expressed. Expression of the indicator indicates when a test candidate binds to the MINK3 protein and can be identified as an MINK3 protein. Using the same system and the identified MINK3 proteins the reverse can be performed. Namely, the MINK3 proteins provided herein can be used to identify new baits, or agents which interact with MINK3 proteins. Additionally, the two-hybrid system can be used wherein a test candidate is added in addition to the bait and the MINK3 protein encoding nucleic acids to determine agents which interfere with the bait, such as Nck, and the MINK3 protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Screening for agents that modulate the activity of MINK3 protein may also be done. In a preferred embodiment, methods for screening for a bioactive agent capable of modulating the activity of MINK3 protein comprise the steps of adding a candidate bioactive agent to a sample of a MINK3 protein (or cells comprising a MINK3 protein) and determining an alteration in the biological activity of the MINK3 protein. "Modulating the activity of a MINK3 protein" includes an increase in activity, a decrease in activity, or a change in the type or kind of activity present. Thus, in this embodiment, the candidate agent may bind to MINK3 protein (although this may not be necessary), and will alter at least one MINK3 biological or biochemical activity as described herein. The methods include both in vitro screening methods, as are generally outlined above, and in vivo screening of cells for alterations in the presence, distribution, activity or amount of MINK3 protein.

In a preferred embodiment, the present invention sets forth methods for screening for modulators of MINK3 activity. By "MINK3 activity" or "MINK3 protein activity" or grammatical equivalents herein is meant at least one of the MINK3 protein's biological activities, including, but not limited to, its ability to bind to Nck, modulate the phosphorylation of JNK and/or ERK, modulate JNK and/or ERK activity, modulate signal transduction via the JNK and/or ERK pathways, modulate F-actin stability, phosphorylate Gelsolin, inhibit taxol-induced RB cleavage and apoptosis, effect changes in morphology or oppose such effective changes, modulate cell proliferation, modulate growth factor-induced proliferation, modulate growth factor-induced ERK activation, modulate AP-1 induced transcription, modulate transcription induced by AP-1 response elements. By "modulate" is meant increase, decrease, or alter. In some embodiments, fragments of the MINK3 protein are preferred, particularly fragments having one or more MINK3 protein activities.

In a preferred embodiment, the activity of the MINK3 protein is decreased; in another preferred embodiment, the activity of the MINK3 protein is increased. Thus, bioactive agents that are antagonists are preferred in some embodiments, and bioactive agents that are agonists may be preferred in other embodiments. As used herein, increased or overexpressed means an increase of at least 10%, more preferably 25-50%, more preferably 50%-75%, and more preferably at least a 100% to 500% increase over the native state. As used herein, decreased or underexpressed means a decrease of at least 10%, more preferably 25-50%, more preferably 50%-75%, and more preferably at least a 100% to 500% decrease over the native state, i.e., compared to without administeration of the MINK3 proteins, nucleic acids or candidate agents as described herein.

In a preferred embodiment, the invention provides methods for screening for bioactive agents capable of modulating the activity of an MINK3 protein. The methods comprise adding a candidate bioactive agent, as defined above, to a cell comprising a MINK3 protein. Preferred cell types include almost any cell, including HeLa cells, 293 cells, MDA-MB-231 cells and Phoenix cells. The cells contain a recombinant nucleic acid that encodes an MINK3 protein. In a preferred embodiment, a library of candidate agents are tested on a plurality of cells comprising a nucleic acid encoding a MINK3 protein.

The activity assays, such as having an effect on Nck binding, cytoskeleton organization, JNK and/or ERK phosphorylation, JNK and/or ERK activation, JNK and/or ERK signal transduction, F-actin stability, cell proliferation, survival following taxol treatment, Rb cleavage following taxol treatment, and growth factor-induced ERK activation can be performed to confirm the activity of MINK3 proteins which have already been identified by their sequence identity/similarity to the sequences set forth in SEQ ID NOs:1-6 or hybridization to the sequences set forth in SEQ ID NOs:2, 4, and 6, as well as to further confirm the activity of lead compounds identified as modulators of the MINK3 proteins provided herein.

The components provided herein for the assays provided herein may also be combined to form kits. The kits can be based on the use of the protein and/or the nucleic acid encoding the MINK3 proteins. In one embodiment, other components are provided in the kit. Such components include one or more of packaging, instructions, antibodies, and labels. Additional assays such as those used in diagnostics are further described below.

Using the activity and binding assays provided herein, bioactive agents, preferably small molecule chemical compositions as described herein, that may be used as pharmacological compounds are identified. Compounds with pharmacological activity are able to enhance or interfere with the activity of the MINK3 protein. The compounds having the desired pharmacological activity may be administered in a physiologically acceptable carrier to a host, as further described below.

The present discovery relating to the role of MINK3 proteins in cell proliferation thus provides methods and compositions for inducing or preventing cell proliferation in cells.

In a preferred embodiment, the MINK3 proteins, and particularly MINK3 protein fragments, are useful in the study or treatment of conditions which are mediated by the MINK3 proteins, i.e., to diagnose, treat or prevent MINK3 associated disorders. "MINK3 associated disorders" or "disease states" include conditions involving both insufficient or excessive cell proliferation, preferably cancer. In another preferred embodiment, candidate bioactive agents, preferably small molecule chemical compositions as described herein, are useful in the study or treatment of conditions which are mediated by the MINK3 proteins, i.e. to diagnose, treat or prevent MINK3 associated disorders, including and preferably cancer.

Thus, in one embodiment, methods and compositions for the modulation of proliferation in cells or organisms are provided. In one embodiment, the methods comprise administering to a cell or individual in need thereof, a MINK3 protein in a therapeutic amount. Alternatively, an anti-MINK3 antibody that reduces or eliminates the biological activity of the endogenous MINK3 protein is administered. In another embodiment, a bioactive agent as identified by the methods provided herein is administered. Alternatively, the methods comprise administering to a cell or individual a recombinant nucleic acid encoding an MINK3 protein. As will be appreciated by those in the art, this may be accomplished in any number of ways. In a preferred embodiment, the activity of MINK3 is increased by increasing the amount of MINK3 in the cell, for example by overexpressing the endogenous MINK3 or by administering a gene encoding a MINK3 protein, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entirety.

In a preferred embodiment, MINK3 antisense nucleic acids are administered to a cell or individual. In a preferred embodiment, MINK3 antisense nucleic acid decreases the activity of MINK3 by decreasing the amount of MINK3 mRNA and/or protein in the cell or individual. In a preferred embodiment, such a MINK3 antisense nucleic acid comprises the sequence complement of the nucleic acid sequence set forth by nucleotides 2804-3187 in SEQ ID NO:2. In another preferred embodiment, such a MINK3 antisense nucleic acid consists essentially of the sequence complement of the nucleic acid sequence set forth by nucleotides 2804-3187 in SEQ ID NO:2.

It appears that MINK3 is important in cell cycle regulation. Without being bound by theory, the present invention provides methods and compositions for the determination of cell cycle disorders. In one embodiment, the invention provides methods for identifying cells containing variant MINK3 genes comprising determining all or part of the sequence of at least one endogenous MINK3 gene in a cell. As will be appreciated by those in the art, this may be done using any number of sequencing techniques. In a preferred embodiment, the invention provides methods of identifying the MINK3 genotype of an individual comprising determining all or part of the sequence of at least one MINK3 gene of the individual. This is generally done in at least one tissue of the individual, and may include the evaluation of a number of tissues or different samples of the same tissue. The method may include comparing the sequence of the sequenced MINK3 gene to a known MINK3 gene, i.e. a wild-type gene.

The sequence of all or part of the MINK3 gene can then be compared to the sequence of a known MINK3 gene to determine if any differences exist. This can be done using any number of known sequence identity programs, such as Bestfit, etc. In a preferred embodiment, the presence of a difference in the sequence between the MINK3 gene of the patient and the known MINK3 gene is indicative of a disease state or a propensity for a disease state.

In one embodiment, methods for determining cell cycle disorders comprise measuring the activity of MINK3 in a tissue from the individual or patient, which may include a measurement of the amount or specific activity of a MINK3 protein. This activity is compared to the activity of MINK3 from either an unaffected second individual or from an unaffected tissue from the first individual. When these activities are different, the first individual may be at risk for a cell cycle disorder such as cancer. In this way, for example, monitoring of various disease conditions may be done by monitoring the levels of protein or mRNA therefore, or by monitoring protein activity. Similarly, expression levels and activity levels may correlate to the prognosis.

In one aspect, the expression levels of MINK3 genes are determined in different patient samples or cells for which either diagnosis or prognosis information is desired. Gene expression monitoring is done on genes encoding MINK3 proteins. In one aspect, the expression levels of MINK3 genes are determined for different cellular states, such as normal cells, cells undergoing apoptosis, cells undergoing transformation, and cancer cells. Thus, differential MINK3 gene expression between different cell states is determined. By comparing MINK3 gene expression levels in cells in different states, information including both up- and down-regulation of MINK3 genes is obtained, which can be used in a number of ways. For example, the evaluation of a particular treatment regime may be evaluated: does a chemotherapeutic drug act to improve the long-term prognosis in a particular patient, whereby prognosis is determined based on MINK3 expression. Similarly, diagnosis may be done or confirmed by comparing patient samples. Furthermore, these gene expression levels allow screening of drug candidates with an eye to mimicking or altering a particular expression level. This may be done by making biochips comprising sets of important MINK3 genes, such as those of the present invention, which can then be used in these screens. These methods can also be done on the protein basis; that is, protein expression levels of the MINK3 proteins can be evaluated for diagnostic purposes or to screen candidate agents. In addition, the MINK3 nucleic acid sequences can be administered for gene therapy purposes, including the administration of antisense nucleic acids, or the MINK3 proteins administered as therapeutic drugs.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, *Nature Biotechnology,* 14:1675-1680 (1996), hereby expressly incorporated by reference. Other techniques include, but are not limited to, quantitative reverse transcriptase PCR, Northern analysis and RNase protection.

MINK3 sequences bound to biochips include both nucleic acid and amino acid sequences as defined herein. In a preferred embodiment, nucleic acid probes to MINK3 nucleic acids (both the nucleic acid sequences having the sequences outlined in SEQ ID NOs:2, 4, and 6 and/or the complements thereof) are made. The nucleic acid probes attached to the biochip are designed to be substantially complementary to the MINK3 protein nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix Gene-Chip™ technology.

The present invention provides novel methods and compositions for screening for compositions which modulate MINK3 bioactivities including Nck binding activity, as well as the ability to modulate cytoskeleton organization, JNK and/or ERK phosphorylation, JNK and/or ERK activation, JNK and/or ERK signal transduction, F-actin stability, cell proliferation, survival following taxol treatment, Rb cleavage following taxol treatment, and growth factor-induced ERK activation. As above, this can be done by screening for modulators of MINK3 gene expression or for modulators of MINK3 protein activity. Gene expression and protein activity may be evaluated on an individual gene and protein basis, or by evaluating the effect of drug candidates on a gene expression or protein expression profile. In a preferred embodiment, the expression profiles are used, preferably in conjunction with high throughput screening techniques to allow monitoring for expression profile genes after treatment with a candidate agent.

A variety of assays my be used to evaluate the effects of agents on MINK3 gene expression. In a preferred embodiment, assays may be run on an individual gene or protein level. That is, having identified the bioactivities of MINK3 described herein, candidate bioactive agents may be screened for the ability to modulate MINK3 gene expression and MINK3 bioactivities. "Modulation" thus includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. Thus, if a gene exhibits a 4 fold increase in tumor compared to normal tissue, a decrease of about four fold is desired; a 10 fold decrease in tumor compared to normal tissue makes a 10 fold increase in expression for a candidate agent desirable, etc. Alternatively, where the MINK3 sequence has been altered but shows the same expression profile or an altered expression profile, the protein will be detected as outlined herein.

As will be appreciated by those in the art, this may be done by evaluation at either the gene transcript or the protein level; that is, the amount of gene expression may be monitored using nucleic acid probes and the quantification of gene expression levels, or, alternatively, the level of the gene product itself can be monitored, for example through the use of antibodies to the MINK3 protein and standard immunoassays. Alternatively, binding and bioactivity assays with the protein may be done as outlined herein.

In a preferred embodiment, gene expression monitoring is done and a number of genes, i.e. an expression profile, are monitored simultaneously, although multiple protein expression monitoring can be done as well. For example, protein can be monitored through the use of antibodies to the MINK3 protein and standard immunoassays (ELISAs, etc.) or other techniques, including mass spectroscopy assays, 2D gel electrophoresis assays, etc.

In this embodiment, the MINK3 nucleic acid probes are attached to biochips as outlined herein for the detection and quantification of MINK3 sequences in a particular cell.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an MINK3 protein is detected by binding the digoxygenin with an anti-digoxygenin secondary antibody and developed with nitro blue tetrazolium and 5-bromo-4-chloro-3-indoyl phosphate.

In another preferred method, expression of MINK3 protein is performed using in situ imaging techniques employing antibodies to MINK3 proteins. In this method cells are contacted with from one to many antibodies to the MINK3 protein(s). Following washing to remove non-specific antibody binding, the presence of the antibody or antibodies is detected. In one embodiment the antibody is detected by incubating with a secondary antibody that contains a detectable label. In another method the primary antibody to the MINK3 protein(s) contains a detectable label. In another preferred embodiment each one of multiple primary antibodies contains a distinct and detectable label. This method finds particular use in simultaneous screening for a plurality of MINK3 proteins. The label may be detected in a luminometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblotting (Western blotting), immunoprecipitation, BIACORE technology, and the like.

The present invention provides additional methods and compositions for screening candidate bioactive agents for the ability to modulate MINK3 bioactivities as described herein.

For example, candidate bioactive agents may be screened for the ability to modulate transcriptional activation by the AP-1 protein complex. In one embodiment, such a method comprises the steps of combining a mammalian cell comprising AP-1 protein complex and a reporter gene fused to a transcriptional regulatory DNA sequence comprising at least one AP-1 response element, and a recombinant nucleic acid encoding a MINK3 protein, and a candidate bioactive agent, and determining the level of reporter gene expression in the presence and absence of candidate agent.

In a preferred embodiment, such a reporter gene is luciferase. In a preferred embodiment, such a candidate agent is a small molecule chemical compound. In a preferred embodiment, such a mammalian cell is a HeLa cell, a 293 cell, a Phoenix cell, an MDA-MD-231 cell, or an A549 cell.

As another example, candidate bioactive agents may be screened for the ability to modulate growth factor-induced ERK activation. In one embodiment, such a method comprises combining a mammalian cell comprising a recombinant nucleic acid encoding a MINK3 protein, and a candidate bioactive agent, and determining the level of ERK activation in the presence and absence of candidate agent.

ERK activation may be determined in several ways as will be appreciated by those in the art. In a preferred embodiment, ERK1 is immunoprecipitated from cell lysate using anti-ERK antibody, and the immunoprecipitate is used in an in vitro kinase assay with myelin basic protein (MBP) as a substrate. In vitro kinase assays are known in the art. In such an in vitro kinase assay, isotopically labeled ATP, preferably $\gamma P^{32}$-labeled, may be used as a source of phosphate for the kinase assay. Briefly, MBP is a substrate for activated ERK1. If activated ERK1 is present in the immunoprecipitate, it will catalyze the transfer of a labeled phosphate group to the substrate, MBP. The products of the in vitro kinase assay may be separated by gel electrophoresis as is known in the art. In this way, the MBP in the kinase assay mixture may be separated from labeled ATP and other constituents in the assay mixture. The amount of isotope incorporated by MBP, indicative of the amount of ERK activity in the immunoprecipitate, may then be determined using techniques known in the art.

In this way, the level of ERK activation in the presence and absence of candidate agent may be determined and compared to identify a candidate agent capable of either inhibiting ERK activation, or inducing ERK activation.

In one embodiment, candidate agents are screened for the ability to modulate ERK activation in response to growth factors. In this embodiment, ERK activation may be determined as described above. In a preferred embodiment, candidate agents are screened for the ability to modulate ERK activation in response to epidermal growth factor (EGF). In one embodiment, such a method comprises exposing mammalian cells comprising the EGF receptor to EGF and then determining ERK activation in the presence and absence of candidate agent as described above.

In another embodiment, such a method comprises combining a cell comprising ERK and MINK3 proteins, as well as comprising a reporter gene under the control of an ERK responsive transcriptional regulatory element (such as an ELK response element, as is known in the art), and a candidate agent, and determining the level of reporter gene expression in the presence and absence of candidate agent.

As will be appreciated by those in the art, the in vitro kinase assay described above may be used similarly to determine the level of JNK activation. The present invention thus provides methods for screening candidate bioactive agents for the ability to modulate JNK activation. In a preferred embodiment, the level of activation of JNK2 is determined in the presence and absence of candidate agent. In such a method, JNK2 is immunoprecipitated with anti-JNK antibody, and a glutathione-S-transferase:c-JUN fusion protein serves as substrate for JNK in an in vitro kinase assay as described above, wherein the c-JUN moiety is a substrate for JNK.

As another example, candidate bioactive agents may be screened for the ability to modulate JNK and/or ERK phosphorylation. In one embodiment, such a method comprises the steps of combining a candidate agent, and a cell comprising a recombinant nucleic acid encoding a MINK3 protein, and ERK and/or JNK proteins, and determining the level of phosphorylation of ERK and/or JNK in the presence and absence of candidate agent. As will be appreciated by those in the art, the determination of ERK and JNK phosphorylation can be done in a number of ways. For example, isotopically-labeled ATP may be added to the cells in order to serve as a source of phosphate for the phosphorylation of JNK and ERK. Following incubation, ERK and/or JNK may be immunoprecipitated using appropriate antibodies as described above, and the immunoprecipitates may be resolved by gel electrophoresis. The amount of radioactive phosphate associated with JNK or ERK (at the appropriate molecular weight) is then determined using techniques known in the art.

Alternatively, such a method may comprise adding a candidate agent to a MINK3 protein which may be isolated or cell-free as in a cell lysate, and then adding an ERK and/or JNK protein, which may be isolated or cell-free, and determining the level of phosphorylation of ERK and/or JNK.

As another example, candidate bioactive agents may be screened for the ability to modulate Rb cleavage in response to exposure to taxol. In a preferred embodiment, such a method comprises combining a mammalian cell comprising a recombinant nucleic acid encoding a MINK3 protein, and Rb, and a candidate agent, and exposing the cell to taxol, and determining the level of Rb cleavage in response to taxol in the presence and absence of candidate agent. The level of Rb cleavage may be determined by immunoprecipitating Rb or a portion thereof from cell lysate using an anti-Rb antibody. The immunoprecipitate may then be resolved using gel electrophoresis. A western blot using anti-Rb antibody may then be done to determine the molecular weight of the Rb species in immunoprecipitate. The appearance of an Rb immunoreactive band at a molecular weight lower than that of native Rb indicates Rb cleavage has occurred. The relative amounts of cleaved to native Rb determines the level of Rb cleavage in the sample.

As another example, candidate bioactive agents may be screened for the ability to modulate cell survival in response to exposure to taxol. In a preferred embodiment, such a method comprises combining a mammalian cell comprising a nucleic acid encoding a MINK3 protein, and a candidate bioactive agent, exposing the cell to taxol, and determining the level of cell survival in the presence and absence of candidate agent. The level of cell survival may be determined in many ways as will be appreciated by those in the art. For example, enzymatic assays for mitochondrial function, such as the MTT or XTT assays, may be used to determine the level of respiration in cells, an indicator of cell survival. Additionally, survival may be inferred from the absence of well known indicators of apoptosis, including genomic DNA laddering.

As another example, candidate bioactive agents may be screened for the ability to modulate proliferation in mammalian cells. In a preferred embodiment, such a method comprises combining a mammalian cell comprising a recombinant nucleic acid encoding a MINK3 protein, and a candidate agent, and determining the proliferation of the cell in the presence and absence of candidate agent. As will be appreciated by those in the art, mammalian cell proliferation may be determined in many ways. For example, cell density in a sample of mammalian cells may be determined over time by measuring the optical density of the sample, preferably at 490 nm. The density of the sample is indicative of the number of cells in the sample, which is in turn indicative of the level of proliferation in the cells of the sample. In a preferred embodiment, A549 cells are used.

As another example, candidate bioactive agents may be screened for the ability to modulate F-actin stability. In a preferred embodiment, such a method comprises combining a mammalian cell comprising a recombinant nucleic acid encoding a MINK3 protein, and a candidate agent, and determining the stability of F-actin in the presence and absence of candidate agent. As will be appreciated by those in the art, the stability of F-actin may be determined in several ways. For example, the amount of actin in a triton X-100 soluble fraction versus the amount of actin in a triton X-100 insoluble fraction may be determined using by running western blots with the fractions and using an anti-actin antibody (Fu et al., JBC 274:30729-30737). After transfection, cells may be lysed directly on a plate using 250 µl Triton X-100 lysis buffer (1% Triton X-100, 150 mM NaCl, 20 mM Tris-HCl, pH 7.4) with protease inhibitors. Cell lysates are centrifuged at 14,000 RPM for 10 min. Supernatant constitutes the Triton X-100 soluble fraction. Pellets are washed once with 500 µl Triton X-100 lysis buffer and dissolved in 500 µl of 1×SDS sample buffer. DNA is sheared by sonication. This represents the Triton X-100 insoluble fraction. Triton X-100 soluble and insoluble fractions derived from the same number of cells are resolved on SDS-PAGE and blotted with an anti-β-actin mAb to determine the content of F- and G-actin.

Alternatively, immunofluorescence using an anti-actin antibody or labeled phalloidin may be done on whole cells to visualize actin filaments in the cells.

As another example, candidate bioactive agents may be screened for the ability to modulate cell morphology. In a preferred embodiment, such a method comprises combining a mammalian cell comprising a recombinant nucleic acid encoding a MINK3 protein, and a candidate agent, and determining cell morphology in the presence and absence of candidate agent. As will be appreciated by those in the art, cell morphology may be determined in many ways. Light microscopy and a variety of cell stains known in the art may be used to visualize cells and determine morphology.

In preferred embodiments, such a method uses Phoenix cells, 293 cells, or MDA-MB-231 cells.

In a preferred embodiment, the ability of a candidate agent to modulate morphology is dependent on MEK activity. Dependence on MEK activity can be determined through the use of the known MEK inhibitor PD98059. Cell morphology can be determined as described above, in the presence and absence of candidate agent, and further in the presence and absence of the MEK inhibitor PD98059.

In one aspect, the invention is directed to methods for screening for a bioactive agent capable of modulating JNK phosphorylation and/or activation. In one aspect, the invention is directed to methods for screening for a bioactive agent capable of modulating the JNK signal transduction pathway. In a preferred embodiment, the methods comprise contacting a candidate bioactive agent to a mammalian cell comprising a recombinant MINK3 nucleic acid encoding a MINK3 protein and a JNK protein and determining JNK activity in the presence of candidate agent. In a preferred embodiment, JNK activity is determined in the presence and absence of candidate agent. The recombinant MINK3 nucleic acid is expressed in said mammalian cell and will activate JNK protein in the absence of candidate bioactive agent. In a preferred embodiment, the encoded MINK3 protein comprises an amino acid sequence having at least about 90% identity to an amino acid sequence selected from the group consisting of the amino acid sequences set forth in SEQ ID NOs:1, 3, and 5. A decrease in the activity of JNK protein in the presence of candidate bioactive agent indicates that the candidate bioactive agent is capable of modulating JNK activity.

In one aspect, the invention is directed to methods for screening for a bioactive agent capable of modulating ERK phosphorylation and/or activation. In one aspect, the invention is directed to methods for screening for a bioactive agent capable of modulating the ERK signal transduction pathway. In a preferred embodiment, the methods comprise contacting a candidate bioactive agent to a mammalian cell comprising a recombinant MINK3 nucleic acid encoding a MINK3 protein and a ERK protein and determining ERK activity in the presence of candidate agent. In a preferred embodiment, ERK activity is determined in the presence and absence of candidate agent. The recombinant MINK3 nucleic acid is expressed in said mammalian cell and will activate ERK protein in the absence of candidate bioactive agent. In a preferred embodiment, the encoded MINK3 protein comprises an amino acid sequence having at least about 90% identity to an amino acid sequence selected from the group consisting of the amino acid sequences set forth in SEQ ID NOs:1, 3, and 5. A decrease in the activity of ERK protein in the presence of candidate bioactive agent indicates that the candidate bioactive agent is capable of modulating ERK activity.

In a preferred embodiment, the methods comprise contacting a mammalian cell with a growth factor which will activate JNK and/or ERK. In a preferred embodiment, the growth factor used in epidermal growth factor (EGF).

In one embodiment, the MINK3 proteins of the present invention may be used to generate polyclonal and monoclonal antibodies to MINK3 proteins, which are useful as described herein. Similarly, the MINK3 proteins can be coupled, using standard technology, to affinity chromatography columns. These columns may then be used to purify MINK3 antibodies. In a preferred embodiment, the antibodies are generated to epitopes unique to the MINK3 protein; that is, the antibodies show little or no cross-reactivity to other proteins. These antibodies find use in a number of applications. For example, the MINK3 antibodies may be coupled to standard affinity chromatography columns and used to purify MINK3 proteins as further described below. The antibodies may also be used as blocking polypeptides, as outlined above, since they will specifically bind to the MINK3 protein.

The anti-MINK3 protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the MINK3 protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-MINK3 protein antibodies may, alternatively, be monoclonal antibodies. Monoclonal antibodies may be prepared using hybridoma methods, such as those described by Kohler, et al., *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the MINK3 protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.*, 133:3001 (1984); Brodeur, et al., *Monoclonal Antibody Production Techniques and Applications*, Marcel Dekker, Inc., New York, pp. 51-63 (1987)).

The culture medium in which the hybridoma cells are cultured can then be assayed for the presence of monoclonal antibodies directed against MINK3 protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson, et al., *Anal. Biochem.*, 107:220 (1980).

After the desired hybridoma cells are identified, the clones may be subcloned by limiting dilution procedures and grown by standard methods (Goding, Supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison, et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-MINK3 protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones, et al., *Nature*, 321:522-525 (1986); Riechmann, et al., *Nature* 332:323-329 (1988); and Presta, *Curr. Op. Struct. Biol.*, 2:593-596 (1992))

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones, et al., *Nature*, 321:522-525 (1986); Riechmann, et al., *Nature*, 332:323-327 (1988); Verhoeyen, et al., *Science*, 239:1534-1536 (1988)), by substituting rodent CDRs or CDR sequences for the corresponding sequences of a human antibody.

Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom, et al, *J. Mol. Biol.*, 227:381 (1991); Marks, et al., *J. Mol. Biol.*, 222:581 (1991)). The techniques of Cole, et al. and Boerner, et al. are also available for the preparation of human monoclonal antibodies (Cole, et al., *Monoclonal Antibodies and Cancer Therapy*, Alan R. Liss, p. 77 (1985); Boerner, et al., *J. Immunol.*, 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks, et al., *Bio/Technology*, 10:779-783 (1992); Lonberg, et al., *Nature*, 368:856-859 (1994); Morrison, *Nature*, 368:812-13 (1994); Fishwild, et al., *Nature Biotechnology*, 14:845-51 (1996); Neuberger, *Nature Biotechnology*, 14:826 (1996); Lonberg, et al., *Intern. Rev. Immunol.*, 13:65-93 (1995).

Bispecific antibodies are monoclonal, preferably human or humanized, antibodies that have binding specificities for at least two different antigens. In the present case, one of the binding specificities is for the MINK3 protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein, et al., *Nature*, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker, et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh, et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-MINK3 protein antibodies of the invention have various utilities. For example, anti-MINK3 protein antibodies may be used in diagnostic assays for an MINK3 protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: a Manual of Techniques*, CRC Press, Inc. pp. 147-158 (1987)). The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter, et al., *Nature*, 144:945 (1962); David, et al., *Biochemistry*, 13:1014 (1974); Pain, et al., *J. Immunol. Meth.*, 40:219 (1981); and Nygren, *J. Histochem. and Cytochem.*, 30:407 (1982).

Anti-MINK3 protein antibodies also are useful for the affinity purification of MINK3 protein from recombinant cell culture or natural sources. In this process, the antibodies against MINK3 protein are immobilized on a suitable support, such a Sephadex resin or filter paper, using methods well known in the art. The immobilized antibody then is contacted with a sample containing the MINK3 protein to be purified, and thereafter the support is washed with a suitable solvent that will remove substantially all the material in the sample except the MINK3 protein, which is bound to the immobilized antibody. Finally, the support is washed with another suitable solvent that will release the MINK3 protein from the antibody.

The anti-MINK3 protein antibodies may also be used in treatment. In one embodiment, the genes encoding the antibodies are provided, such that the antibodies bind to and modulate the MINK3 protein within the cell.

In one embodiment, a therapeutically effective dose of an MINK3 protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for MINK3 protein degradation, or antagonist or agonist degradation or metabolism, as well as systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the MINK3 protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1-100 wt. %.

The pharmaceutical compositions of the present invention comprise an MINK3 protein, agonist or antagonist (including antibodies and bioactive agents as described herein) in a form suitable for administration to a patient. Small molecule chemical compositions as described herein are especially preferred. In a preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

Without being bound by theory, the pharmaceutical compositions provided herein find use in the treatment and/or prohylaxis of cancer, particularly as cancer involves dysregulated cell proliferation, aberrant morphology, and aberrant migration as in metastasis. Further cancer may involve aberrant JNK and/or ERK phosphorylation, JNK and/or ERK activation, and JNK and/or ERK signal transduction.

In one embodiment provided herein, the antibodies are used for immunotherapy, thus, methods of immunotherapy are provided. By "immunotherapy" is meant treatment of MINK3 protein related disorders with an antibody raised against a MINK3 protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an MINK3 protein antigen to which antibodies are raised. As appreciated by one of ordinary skill in the art, the MINK3 protein antigen may be provided by injecting an MINK3 protein against which antibodies are desired to be raised into a recipient, or contacting the recipient with an MINK3 protein nucleic acid, capable of expressing the MINK3 protein antigen, under conditions for expression of the MINK3 protein antigen.

In a preferred embodiment, a therapeutic compound is conjugated to an antibody, preferably an MINK3 protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis, cancer MINK3 protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against MINK3 proteins, or binding of a radionuclide to a chelating agent that has been covalently attached to the antibody.

In a preferred embodiment, MINK3 protein genes are administered as DNA vaccines, either single nucleic acids or combinations of MINK3 protein genes. Naked DNA vaccines are generally known in the art; see Brower, *Nature Biotechnology*, 16:1304-1305 (1998). Methods for the use of nucleic acids as DNA vaccines are well known to one of ordinary skill in the art, and include placing an MINK3 protein gene or portion of an MINK3 protein nucleic acid under the control of a promoter for expression in a patient. The MINK3 protein gene used for DNA vaccines can encode full-length MINK3 proteins, but more preferably encodes portions of the MINK3 proteins including peptides derived from the MINK3 protein. In a preferred embodiment a patient is immunized with a DNA vaccine comprising a plurality of nucleotide sequences derived from a MINK3 protein gene. Similarly, it is possible to immunize a patient with a plurality of MINK3 protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing MINK3 proteins.

In a preferred embodiment, the DNA vaccines include a gene encoding an adjuvant molecule with the DNA vaccine. Such adjuvant molecules include cytokines that increase the immunogenic response to the MINK3 protein encoded by the DNA vaccine. Additional or alternative adjuvants are known to those of ordinary skill in the art and find use in the invention.

EXAMPLES

The following examples serve to more fully describe the manner of using the above-described invention, as well as to set forth the best modes contemplated for carrying out various aspects of the invention. It is understood that this example in no way serve to limit the true scope of this invention, but rather are presented for illustrative purposes. All references cited herein are expressly incorporated by reference in their entirety. Moreover, all sequences displayed, cited by reference or accession number in the references are incorporated by reference herein.

Example 1

A MINK3 antisense nucleic acid complementary to a MINK3 cDNA from a Jurkat cDNA library was identified in a functional screen for nucleic acids capable of inhibiting cell death following exposure of HeLa cells to taxol (data not shown). The antisense nucleic acid comprises a nucleic acid sequence complimentary to that set forth by nucleotides 2804-3187 in SEQ ID NO:2.

MINK3 antisense nucleic acid was used to clone and identify three iso forms of MINK3 (MINK3a, MINK3b, MINK3c, set forth in SEQ ID NOs:2, 4, and 6, respectively).

HeLa cells were transfected with expression vectors encoding MINK3a, MINK3b, Bcl2, or MINK3 antisense nucleic acid complementary to the nucleic acid sequence set forth by nucleotides 2804-3187 in SEQ ID NO:2. As an additional control, cells were transfected with empty vector.

Following transfection, cells were exposed to a range of taxol concentrations and a mitochondrial respiration assay (XTT) was performed on cell lysates to determine viable cells.

Both Bcl2 and MINK3 antisense nucleic acid had an inhibitory effect on taxol-induced cell death, while MINK3a and MINK3b did not appear to affect cell death (FIG. 7).

Example 2

Hela cells were transfected with expression vectors encoding either Bcl2 or GFP, or an expression vector comprising a MINK3 antisense nucleic acid complementary to the nucleic acid sequence set forth by nucleotides 2804-3187 in SEQ ID NO:2. As an additional control, Hela cells were transfected with empty vector alone.

Following transfection, cells were exposed to taxol at a concentration of 40 nm or 60 nm. Cells were collected following taxol treatment and cell lysate was obtained. Western blots were run on cell lysates using anti-RB antibody and anti-Bcl2 antibody. As a control, anti-cdk2 antibody was used.

Rb immunodetection was done on lysates from cells exposed or not exposed to taxol. In samples exposed to taxol, a faster migrating Rb-immunoreactive band ("cleaved Rb") was detected in addition to the normal Rb immunoreactive band. Cleaved Rb was not detectable in cells transfected with Bcl2 and exposed to taxol. The amount of cleaved Rb formed in response to taxol was dramatically reduced in cells transfected with MINK3 antisense nucleic acid complementary to the nucleic acid sequence set forth by nucleotides 2804-3187 in SEQ ID NO:2. GFP and empty expression vectors had no effect on the formation of cleaved Rb in response to taxol (FIG. 10).

Example 3

293 cells comprising a luciferase reporter gene fused to a regulatory sequence comprising an AP1 element were transfected with MINK3 antisense nucleic acid complementary to the nucleic acid sequence set forth by nucleotides 2804-3187 in SEQ ID NO:2, or an MEKK1 expression vector, or an empty expression vector.

Following transfection, luciferase activity was determined using a luminometer, in order to determine the level of expression of the reporter gene.

MEKK1 induced reporter gene expression, while MINK3 antisense nucleic acid inhibited the basal level of reporter gene expression (FIG. 3).

Example 4

Northern blot analysis showed that MINK3 mRNA is expressed at different levels in a number of human tissues, including spleen, thymus, prostate, testis, ovary, small intestine, colon, PBL, leukocytes, heart, brain, placenta, lung, liver, skeletal muscle, kidney and pancreas (FIG. 11).

Example 5

Northern blot analysis showed that MINK3 mRNA is expressed at different levels in a number of tumor cell lines, including HL-60, HeLa S3, K-562, MOLT-4, Raji, SW480, A549, and G361 (FIG. 12).

Example 6

Cells were cotransfected with expression vectors encoding MINK3a, MINK3b, or MEKK1. As a control, empty vector was used in place of MINK3a, MINK3b, or MEKK1 expression vectors.

Cell lysates were collected, and JNK and ERK were immunoprecipitated.

Kinase assays were done using JNK immunoprecipitate, GST-cJUN as substrate, and isotopically labeled γ-ATP.

The kinase assay mixture was resolved using gel electrophoresis, and the level of isotope incorporated into substrate was determined.

Kinase assays were also done using ERK immunoprecipitate, MBP as substrate, and isotopically labeled γ-ATP.

The kinase assay mixture was resolved using gel electrophoresis, and the level of isotope incorporated into substrate was determined.

As a control, western blots "WB" were performed on immunoprecipitates from different samples to compare the amount of JNK2 and ERK1 in each immunoprecipitate.

MINK3a, MINK3b, and MEKK1 induced JNK2 activation, as shown by the increased phosphorylation of GST-cJUN in kinase assays.

MINK3a induced ERK1 activation, as shown by the increased phosphorylation of MBP in kinase assays (FIG. 13).

Example 7

MINK3a interacts with Nck in a yeast two hybrid assay. (data not shown).

Example 8

293 cells were transfected with expression vectors encoding MINK3a and Nck.

Following transfection, cells lysates were collected, and immunoprecipitations were done.

Nck associates with MINK3a in 293 cells. (data not shown)

Example 9

Phoenix cells were transfected with expression vectors encoding GFP and either TNIK, TNIK kinase dead variant (TNIK kd), MINK3a or MINK3b.

Fluorescence microscopy was done to visualize the morphology of transfected cells.

MINK3a caused a morphological change in Phoenix cells. (data not shown)

Example 10

MDA-MB-231 cells expressing GFP, MINK3a, MINK3b, or MINK3 antisense nucleic acid complementary to the nucleic acid sequence set forth by nucleotides 2804-3187 in SEQ ID NO:2 were generated.

Light microscopy was used to visualize cell morphology of transfected cells.

MINK3a caused a morphological change in MDA-MB-231 cells.

When MINK3a expressing clone was treated with the MEK inhibitor PD98059, the cells reverted to their normal morphology, i.e. a morphology characteristic of cells not transfected with MINK3 a expression vector.

Thus, the morphological change induced by MINK3a appears to be MEK-dependent (FIGS. 14 and 15).

Example 11

MDA-MB-231 cells were transfected with expression vectors encoding either GFP, MINK3a, MINK3b, or empty expression vector.

Immunofluorescence was done on cell cultures using a fluorescently-labeled F-actin binding toxin. (data not shown)

Example 12

A549 cells were transfected with expression vector encoding either GFP, MINK3a, MINK3b, or MINK3 antisense nucleic acid complementary to the nucleic acid sequence set forth by nucleotides 2804-3187 in SEQ ID NO:2.

Following transfection, cells were grown in low serum (0.5% fetal bovine serum) or high serum (10% fetal bovine serum) for four days.

The optical density of the cultures was determined at 490 nm in order to determine the cell density and compare proliferation between cultures.

MINK3a inhibited proliferation of this tumor cell line in low serum (FIG. 8).

Example 13

Cells comprising an EGF receptor and a luciferase reporter gene fused to a regulatory DNA sequence responsive to ERK activation were transfected with expression constructs encoding MINK3a, MINK3b, TNIK, or MINK antisense nucleic acid complementary to the nucleic acid sequence set forth by nucleotides 2804-3187 in SEQ ID NO:2. As a control, cells were transfected with empty vector.

Following transfection, cells were exposed to EGF. Following exposure to EGF, luciferase activity was determined using a luminometer, in order to determine reporter gene expression.

MINK3 antisense nucleic acid inhibited the basal level of ERK-mediated transcription of the reporter gene, as well as EGF-induced ERK-mediated expression of the reporter gene (FIG. 9).

Example 14

HT-1080 cells (Human fibrosarcoma cell line) were infected with retrovirus expressing IGFP, Mink3a and Mink3aKD (a kinase dead mutant with point mutation in kinase domain.

Invasion assay was performed in BioCoat Invasion chambers pre-coated with Matrigel according to manufacturer's instructions (BD Biosciences) in the presence and the absence of 100 ng/ml HGF (hepatocyte growth factor) (see, e.g., Trusolino & Comoglio, (2002) *Nat Rev Cancer* 2(4): 289-300; Wells, (2000) *Adv. Cancer Res.* 78:31-101; Wells et al., (2002) *Acta Oncol* 41(2):124-30).

Expression of kinase dead mutant of Mink3a in HT1080 cell (Human fibrosarcoma cell line) greatly reduced its invasion potential comparing with GFP control and wild-type Mink3 (see FIG. 16). These results indicate that Mink3a is involved in regulation of cellular migration and tumor and/or cancer metastasis. Modulators of Mink3a therefore would be useful for treatment of cellular migration and metastasis.

Methods:

Antibodies and cytokines—Antibodies used in this report include: anti-HA mAb (Babco) and pAb (Santa Cruz Biotechnology); anti-FLAG mAb (Sigma) and pAb (Santa Cruz); anti-Myc mAb (Babco); anti-Traf2 pAb (Santa Cruz); anti-NCK mAb (Transduction Labs); anti-β-actin mAb (Sigma). TNFα was purchased from Calbiochem.

Plasmid construction—Full length human MINK3 was cloned into pCI (Promega) derived expression vector pYCI under the control of the CMV promoter with an HA epitope tag (AYPYDVPDYA) (SEQ ID NO:7) inserted on the N-terminus by PCR. A kinase mutant form of MINK3 was constructed using the QuikChange mutagenesis kit (Stratagene) with Oligos AGCTTGCAGCCATCAGGGTTATG-GATGTCAC (SEQ ID NO:8) and GTGACATCCATAAC-CTTGATGGCTGCAAGCT (SEQ ID NO:9) to change the highly conserved lysine 54 in the kinase domain to arginine. Full length human NCK was similarly cloned into pYCI with a FLAG epitope tag at the N-terminus. Myc-JNK2 and Myc-ERK1 were constructed in the pCR3.1 vector with a Myc epitope tag (ASMEQKLISEEDLN) (SEQ ID NO:10) inserted on the N-terminus of JNK2 and ERK1, respectively. All the truncation mutants were constructed by PCR.

Cell culture, transfection of Phoenix-A cells and immunoprecipitation—Phoenix-A cells (derivatives of 293 cells) (Coligan, et al., *Current Protocols in Immunology Supplement*), 31:10.28.1-10.28.17 (1999)) were grown in Dulbecco's modified Eagle's medium MINK3plemented with 10% fetal bovine serum. Transfection of Phoenix-A cells was performed using the standard calcium phosphate method (Coligan, et al., *Current Protocols in Immunology Supplement*), 31:10.28.1-10.28.17 (1999)). Either $4 \times 10^5$ cells in a 6-well plate or $3 \times 10^6$ cells in a 100 mm tissue culture dish were seeded 16 hours before transfection. 3 μg of DNA was used in the transfection for each well of a 6-well plate, and 10 μg DNA was used for each 100 mm dish. Media was changed 8 hours after transfection. Cells were lysed in lysis buffer (1% NP-40, 20 mM Tris-HCl, pH 8.0, 150 mM NaCl) with protease inhibitors (Boehringer Mannheim) and analyzed 24 hours after transfection. Cell lysates were cleared by centrifugation (14,000 RPM×10 min). For immunoprecipitation studies, cell lysates ($2 \times 10^6$ cells/lane) were rotated with 2-3 μg of desired antibodies and 20 μl 50% slurry of protein A Sepharose (Pharmacia) for 1.5 hrs. Immune complexes were precipitated and the pellets washed three times with lysis buffer. Washed precipitates were subjected to SDS-PAGE analysis and Western blotting. Supersignal and Supersignal West Duro substrates (Piers) were used as detection systems for the Western blotting.

In vitro kinase assays—For the JNK in vitro kinase assay, Myc-JNK2 was co-transfected into Phoenix-A cells with MINK3 mutants, Traf2 or MEKK as described above. 24 hours after transfection, cells were lysed with lysis buffer MINK3plemented with 20 mM β-glycerophosphate, 1 mM NaF, 1 mM Na$_3$VO$_4$ and protease inhibitors. Myc-JNK2 was precipitated from clarified cell lysates with an anti-Myc mAb and the pellets were washed three times with lysis buffer and two times with kinase buffer (20 mM HEPES, pH 7.4, 10 mM MnCl$_2$, 10 mM MgCl$_2$, 20 mM β-glycerophosphate, 1 mM NaF, 1 mM Na$_3$VO$_4$, 0.5 mM DTT). For the kinase reactions, immunoprecipitates were incubated with 1 μg glutathione S-transferase (GST) c-Jun (1-79) (Santa Cruz Biotechnology) in 20 μl kinase buffer MINK3plemented with 1 μM PKI peptide (Sigma), 10 μM ATP, 5 μCi γ-P$^{32}$ ATP for 20 minutes at 30° C. Kinase reactions were stopped by addition of 20 μl 2×SDS sample buffer (Norvex), heated at 95° C. for 5 minutes and then loaded onto SDS-PAGE. ERK and p38 in vitro kinase assays were conducted in a similar fashion. For ERK kinase assays, an anti-Myc mAb was used to immunoprecipitate Myc-ERK1 and Myelin Basic Protein (MBP, Sigma) was used as an exogenous substrate. For p38 kinase assays, an anti-FLAG mAb was used to immunoprecipitate FLAG-p38 and GST-ATF2 (Santa Cruz) was used as an exogenous substrate. For in vitro kinase assays on MINK3, 3 μg wild type HA-MINK3 or 3 μg kinase mutant form of HA-MINK3 was expressed in Phoenix-A cells and immunoprecipitated with an anti-HA antibody. Immune complexes were subjected to kinase assays as described above in the absence or presence of 0.5 μg Gelsolin as an exogenous substrate.

Fluorescent microscopy—Phoenix-A cells seeded in 6-well plates were co-transfected with GFP and MINK3 constructs as described above. 24 hours after transfection, cells were observed using a Nikon Eclipse TE 300 fluorescent microscope. For detection of apoptosis, Hoechst 33258 was added to transfected Phoenix-A cells (final concentration 5 μg/ml) and the cells were incubated for 30 min at 37° C. before microscopic observation.

To determine kinase activity, a putative kinase mutant form of MINK3, designated as MINK3(KM), was constructed with a conserved lysine (Lys-54) residue in the ATP binding pocket mutated to arginine. An HA epitope tag was inserted on the N-terminal portion of MINK3(WT) and MINK3(KM). Both proteins were transiently expressed in Phoenix-A cells, and the expressed proteins were subjected to immunoprecipitation and an in vitro kinase assay. A strong phosphorylated band at 150 kD was detected in the MINK3(WT) expressed lane, but not in the MINK3(KM) expressed lane. Immunoblotting with an anti-HA antibody showed equal levels of expression of both MINK3(WT) and MINK3(KM) at 150 kD. Therefore, the phosphorylated band in the in vitro kinase assay represented autophosphorylated MINK3, and the MINK3(KM) mutant was deficient in protein kinase activity.

Tissue distribution of MINK3—The expression pattern of the MINK3 message was examined by human multi-tissue Northern blot. Since MINK3 shared high homology with NIK, a probe corresponding to nucleotides 1264-2427 of MINK3 was used to rule out any potential cross-hybridization. This region shared only 40% amino acid identity with NIK. Three major bands of sizes 6.5 kb, 7.5 kb and 9.5 kb were detected. Alternative splicing in the coding region described above is unlikely to account for the size differences among the three messages, since the largest isoform is only 273 bps bigger than the smallest isoform. Alternative splicing in the untranslated region or alternative usage of polyA sites could be possible explanations. This phenomenon is not unique to MINK3. NIK and HGK also have multiple message sizes. MINK3 is ubiquitously expressed, with higher levels of message detected in heart, brain and skeletal muscle. Interestingly, heart and skeletal muscle predominantly expressed the 6.5 kb form; placenta, kidney and pancreas predominantly expressed the 7.5 kb form; brain, lung and liver expressed all three forms at a similar level. It is currently unknown whether these messages have different functional roles.

Interaction of MINK3 with NCK—The interaction of MINK3 with NCK was investigated in a similar fashion.

Following transient expression of HA-MINK3 in Phoenix-A cells, the cell lysates were immunoprecipitated with an anti-HA antibody and blotted with an anti-NCK antibody. Endogenous NCK specifically co-immunoprecipitated with HA-MINK3. To map the domains on MINK3 required for this interaction, HA-tagged MINK3 mutants were co-expressed with FLAG-tagged NCK and the HA-MINK3 mutants were immunoprecipitated with an anti-HA antibody. The immune complexes were then blotted with an anti-FLAG antibody. MINK3(WT), MINK3(N2), MINK3(C1) and MINK3(M) were all able to associate with NCK, suggesting that the intermediate domain is also sufficient for MINK3 to bind NCK. Neither the GCKH domain nor the kinase domain showed any detectable binding to NCK. Immunoblotting cell lysates with anti-HA and anti-FLAG antibodies showed equivalent levels of expression of the transfected proteins.

Activation of JNK2 by MINK3—We further examined whether MINK3 was able to activate the JNK pathway. 1 µg, 2 µg or 3 µg of MINK3 expression plasmid was co-transfected into Phoenix-A cells with Myc-JNK2. 24 hours after transfection, Myc-JNK2 was immunoprecipitated from cell lysates and its kinase activity measured using GST-cJun (1-79) as a substrate. Co-transfection of MINK3 enhanced JNK2 kinase activity in a dose dependent fashion. When 3 µg of MINK3 was transfected, JNK2 activity was enhanced 3-4 fold. A similar magnitude of JNK2 activation was observed when cells were treated for 15 minutes with 100 ng/ml of TNF. Also consistent with published result (Natoli, et al., Science, 275:200-203 (1997)), TRAF2 potently activated JNK2 activity. The expression levels of Myc-JNK2 were controlled by immunoblotting cell lysates with an anti-Myc antibody.

To determine whether MINK3 can also activate the ERK and p38 pathways, Myc-ERK1 and FLAG-p38 were co-transfected into Phoenix-A cells with different doses of MINK3. The transfected kinases were then immunoprecipitated from cell lysates and the kinase activities measured using MBP and GST-ATF2 as exogenous substrates. In contrast to JNK2, neither ERK1 nor p38 was activated by MINK3 overexpression, while co-transfection of MEKK1 potently activated both kinases. In addition, MINK3 did not activate NF-KB (data not shown).

To further investigate the mechanism of this activation, the cohort of MINK3 mutants were co-transfected into Phoenix-A cells with Myc-JNK2 and the ability of these mutants to up-regulate JNK2 kinase activity was examined by the in vitro kinase assay. MINK3(WT), MINK3(KM), MINK3(C1) and MINK3(C2) were all able to activate Myc-JNK2, while MINK3(N1), MINK3(N2), MINK3(M) were not. This result suggested that the C-terminal GCKH region is both necessary and sufficient for activation of the JNK pathway, while the kinase domain is dispensable.

NIK was cloned by its ability to interact with the adapter protein NCK. It associated with NCK SH3 domains via two PxxPxR sequences in the intermediate domain, PCPPSR (aa 574-579) (SEQ ID NO:11) and PRVPVR (aa 611-616) (SEQ ID NO:12). Both sequences were required for efficient interaction (Su, et al., EMBO J., 16:1279-1290 (1997)). Similar to NIK, MINK3 also interacted with NCK via the intermediate domain. However, PCPPSR (SEQ ID NO:11) is not conserved in MINK3. Instead, MINK3 contained two other PxxPxR sequences, PNLPPR (aa 562-567) (SEQ ID NO:13) and PPLPTR (aa 647-652) (SEQ ID NO:14), in addition to the conserved PKVPQR (aa 670-675) (SEQ ID NO:15). MINK3 likely interacted with NCK through the cooperative interaction with these three PxxPxR sequences. NCK is an adapter protein involved in many growth factor receptor mediated signal transduction pathways (McCarthy, Bioessays, 20:913-921 (1998)). It has been proposed that the NIK-NCK interaction may recruit NIK to receptor or non-receptor tyrosine kinases to regulate MEKK1 (Su, et al., EMBO J., 16:1279-1290 (1997)). MINK3 may be recruited in a similar fashion.

We claim:

1. A recombinant MINK3 polypeptide, comprising an amino acid sequence having at least 98% identity to SEQ ID NO:1, wherein the MINK3 polypeptide has kinase activity.

2. The recombinant MINK3 polypeptide of claim 1, comprising SEQ ID NO:1.

* * * * *